(12) United States Patent
Doyle et al.

(10) Patent No.: US 6,900,216 B2
(45) Date of Patent: May 31, 2005

(54) DIHYDROIMIDAZO[2,1-B]THIAZOLE AND DIHYDRO-5H-THIAZOLO[3,2-A] PYRIMIDINES AS ANTIDEPRESSANT AGENTS

(75) Inventors: Kevin James Doyle, Nottingham (GB); Frank Kerrigan, Nottingham (GB); John Paul Watts, Nottingham (GB)

(73) Assignee: Knoll GmbH, Ludwigshafen (DE)

( * ) Notice: Subject to any disclaimer, the term of this patent is extended or adjusted under 35 U.S.C. 154(b) by 0 days.

(21) Appl. No.: 10/221,459

(22) PCT Filed: Mar. 10, 2001

(86) PCT No.: PCT/EP01/02700
§ 371 (c)(1),
(2), (4) Date: Jan. 16, 2003

(87) PCT Pub. No.: WO01/68653
PCT Pub. Date: Sep. 20, 2001

(65) Prior Publication Data
US 2003/0166628 A1 Sep. 4, 2003

(30) Foreign Application Priority Data
Mar. 11, 2000 (GB) .............................................. 0005789

(51) Int. Cl.⁷ ..................... A61K 31/429; C07D 513/04
(52) U.S. Cl. .................... 514/259.2; 514/393; 544/281; 548/303.7
(58) Field of Search .............................. 514/259.2, 393; 544/281; 548/303.7

(56) References Cited

FOREIGN PATENT DOCUMENTS

| WO | WO 94/06789 | 3/1994 | .......... C07D/333/70 |
|----|-------------|--------|----------------------|
| WO | WO 97/02269 | 1/1997 | .......... C07D/513/04 |
| WO | WO 98/41528 | 9/1998 | .......... C07D/513/10 |
| WO | WO 00/71548 | 11/2000 | .......... C07D/513/04 |
| WO | WO 00/71549 | 11/2000 | .......... C07D/513/04 |

OTHER PUBLICATIONS

International Search Report mailed on Jul. 18, 2001 for International Patent Application PCT/EP 01/02700 filed on Mar. 10, 2001.

*Primary Examiner*—Richard L. Raymond
(74) *Attorney, Agent, or Firm*—Bromberg & Sunstein LLP

(57) ABSTRACT

The present invention relates to certain novel substituted dihydroimidazo[2,1-b]thiazole and dihydro-5H-thiazolo[3,2-a]pyrimidine compounds including pharmaceutically acceptable salts thereof which have an affinity for 5-HT$_{1A}$ receptors and which inhibit neuronal reuptake of 5-hydroxytryptamine and/or noradrenaline, to processes for their preparation, to pharmaceutical compositions containing them and to their use in the treatment of depression, anxiety, psychoses including schizophrenia, tardive dyskinesia, obesity, drug addiction, drug abuse, cognitive disorders, Alzheimer's disease, obsessive-compulsive behaviour, panic attacks, social phobias, eating disorders such as bulimia, anorexia, snaking and binge eating, non-insulin dependent diabetes mellitus, hyperglycaemia, hyperlipidaemia, stress, as an aid to smoking cessation and in the treatment and/or prophylaxis of seizures, neurological disorders such as epilepsy and/or in which there is neurological damage such as stroke, brain trauma, cerebral ischaemia, head injuries and haemorrhage.

29 Claims, No Drawings

DIHYDROIMIDAZO[2,1-B]THIAZOLE AND DIHYDRO-5H-THIAZOLO[3,2-A] PYRIMIDINES AS ANTIDEPRESSANT AGENTS

The present invention relates to certain novel substituted dihydroimidazo[2,1-b]thiazole and dihydro-5H-thiazolo[3,2-a]pyrimidine compounds which have affinity for 5-HT$_{1A}$ receptors and which inhibit neuronal reuptake of 5-hydroxytryptamine and/or noradrenaline, to processes for their preparation, to pharmaceutical compositions containing them and to their use in the treatment of depression, anxiety, psychoses (for example schizophrenia), tardive dyskinesia, obesity, drug addiction, drug abuse, cognitive disorders, Alzheimer's disease, obsessive-compulsive behaviour, panic attacks, social phobias, eating disorders such as bulimia, anorexia, snacking and binge eating, non-insulin dependent diabetes mellitus, hyperglycaemia, hyperlipidaemia, stress, as an aid to smoking cessation and in the treatment and/or prophylaxis of seizures, neurological disorders such as epilepsy and/or conditions in which there is neurological damage such as stroke, brain trauma, cerebral ischaemia, head injuries and haemorrhage.

WO 98/41528 discloses that compounds of Formula A

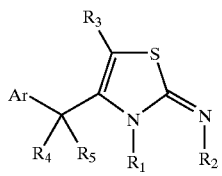

A including pharmaceutically acceptable salts thereof in the form of individual enantiomers, racemates, or other mixtures of enantiomers,
in which:
Ar is phenyl, naphthyl or benzo[b]thiophenyl, each of which may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group containing 1 to 3 carbon atoms optionally substituted by one or more halo, e) a phenoxy group optionally substituted by one or more halo or f) phenyl optionally substituted by one or more halo;
R$_1$ and R$_2$, which may be the same or different, independently are a) H, b) an alkyl group containing 1 to 6 carbon atoms, c) an alkenyl group containing 3 to 6 carbon atoms, d) a cycloalkyl group containing 3 to 7 carbon atoms, e) a cycloalkylmethyl group in which the ring contains 3 to 7 carbon atoms, f) an aryl or heteroaryl group optionally substituted by one or more substituents selected from i) halo, ii) an alkyl group containing 1 to 3 carbon atoms optionally substituted by one or more halo, iii) an alkoxy group containing 1 to 3 carbon atoms optionally substituted by one or more halo, iv) an alkylthio group containing 1 to 3 carbon atoms optionally substituted by one or more halo, g) an arylalkyl or heteroarylalkyl group in which the alkyl chain contains 1 to 3 carbon atoms and in which the aryl or heteroaryl group may optionally be substituted by one or more substituents selected from i) halo, ii) an alkyl group containing 1 to 3 carbon atoms optionally substituted by one or more halo, iii) an alkoxy group containing 1 to 3 carbon atoms optionally substituted by one or more halo, iv) an alkylthio group containing 1 to 3 carbon atoms optionally substituted by one or more halo; or R$_1$ and R$_2$ form an alkylene chain optionally substituted by one or more alkyl groups each containing 1 to 3 carbon atoms, such that, together with the atoms to which they are attached, they form a 5 or 6 membered ring,
R$_3$ is a) H, b) an aryl or heteroaryl group optionally substituted by one or more substituents selected from i) halo, ii) an alkyl group containing 1 to 3 carbon atoms optionally substituted by one or more halo, iii) an alkoxy group containing 1 to 3 carbon atoms optionally substituted by one or more halo, iv) an alkylthio group containing 1 to 3 carbon atoms optionally substituted by one or more halo, c) an arylmethyl group in which the aryl is optionally substituted by one or more substituents selected from i) halo, ii) an alkyl group containing 1 to 3 carbon atoms optionally substituted by one or more halo, iii) an alkoxy group containing 1 to 3 carbon atoms optionally substituted by one or more halo, iv) an alkylthio group containing 1 to 3 carbon atoms optionally substituted by one or more halo; or d) an alkoxyalkyl group containing 3 to 6 carbon atoms; and
R$_4$ and R$_5$, which may be the same or different, independently are an alkyl group containing 1 to 3 carbon atoms, or R$_4$ and R$_5$ together with the atom to which they are attached form a cycloalkyl ring containing 3 to 6 carbon atoms;
are useful in the treatment of depression, anxiety, Parkinson's disease, obesity, cognitive disorders, seizures, neurological disorders such as epilepsy, and as neuroprotective agents to protect against conditions such as stroke. The compounds of the present invention are not disclosed or suggested in this document.

Sharpe C. J and Shadbolt R. S. (Journal of Medicinal Chemistry, 1971, Vol 14 No.10, p977–982) disclose certain dihydroimidazo[2,1-b]thiazole compounds having antidepressant activity. However, the document also states that these compounds were generally less active and more toxic than the imidazolines also disclosed in the document. The compounds of the present invention are not disclosed or suggested in this document.

WO 97/02269 discloses that compounds of Formula B

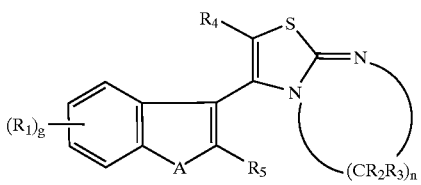

B including pharmaceutically acceptable salts thereof
in which
A is S(O)$_p$ or O;
p is 0, 1 or 2;
g is 0, 1, 2, 3, or 4;
n is 2 or 3;
R$_1$ is a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; $R_1$ being the same or different when g is 2, 3 or 4;

$R_2$, $R_3$ and $R_4$ independently are H or an alkyl group containing 1 to 3 carbon atoms optionally substituted by one or more halo; and $R_5$ is a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, m) an amino group optionally substituted by one or two alkyl groups each containing 1 to 3 carbon atoms, or n) H;

have affinity for 5-$HT_{1A}$ receptors and inhibit neuronal reuptake of 5-hydroxytryptamine and/or noradrenaline. These compounds are stated to be useful in the treatment of CNS disorders. However, these compounds exhibit activity as monoamine oxidase inhibitors and/or have affinity for other receptors, for example muscarinic receptors, and are therefore likely to cause undesired side effects. Surprisingly the present invention provides compounds with unexpectedly superior selectivity and efficacy. The compounds of the present invention are not disclosed or suggested in this document.

International applications numbers PCT/EP00/4279 and PCT/EP00/04278, both filed May 11, 2000, disclose certain substituted dihydroimidazo[2,1-b]thiazole and dihydro-5H-thiazolo[3,2-a]pyrimidine compounds which have affinity for 5-$HT_{1A}$ receptors and inhibit neuronal reuptake of 5-hydroxytryptamine and/or noradrenaline.

U.S. Pat. No. 4,160,768 discloses that 3-(2-benzo[b]furanyl)-5,6-dihydroimidazo[2,1-b]thiazole is useful as an anti-inflammatory agent. This document does not disclose or suggest the compounds of the present invention.

The present invention provides compounds of Formula I

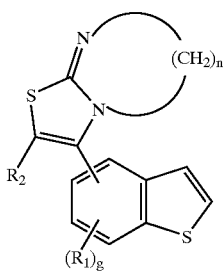

I including pharmaceutically acceptable salts thereof in which g is 0, 1, 2, 3, 4 or 5;

n is 2 or 3;

$R_1$ is a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; $R_1$ being the same or different when g is 2, 3, 4 or 5;

$R_2$ represents H, an alkyl group containing 1 to 6 carbon atoms optionally substituted by one or more halo, a hydroxyalkyl group containing 1 to 6 carbon atoms, an α-hydroxyarylmethyl group, a hydroxyalkenyl group containing 3 to 6 carbon atoms in which hydroxy is not attached directly to either carbon of the double bond, a hydroxyalkynyl group containing 3 to 6 carbon atoms in which hydroxy is not attached directly to either carbon of the triple bond, a hydroxycycloalkyl group containing 3 to 6 carbon atoms, an alkenyl group containing 2 to 8 carbon atoms, an arylalkenyl group containing 8 to 10 carbon atoms, a cycloalkyl group containing 3 to 6 carbon atoms, a $C_{3-4}$ alkynylalkoxy$C_{1-3}$alkyl group, a $C_{4-6}$ cycloalkylalkoxy$C_{1-3}$alkyl group, a $C_{1-3}$alkoxy$C_{1-3}$alkyl group, a $C_{1-3}$alkylthio$C_{1-3}$alkyl group, a $C_{1-3}$alkoxy group, a $C_{1-3}$alkylthio group, an arylthio group, a $C_{1-6}$ alkanoyl group, a $C_{3-6}$ alkoxycarbonylalkyl group, cyano, halo, a $C_{1-4}$alkyliminomethyl group, a $C_{1-4}$alkylaminoalkyl group or a hydroxyiminomethyl group; and wherein the condensed thiazole ring may be attached at the 2, 4, 5, 6 or 7-position of the benzothiophene ring with the proviso that when the condensed thiazole ring is attached at the 2-position or the 5-position of the benzothiophene ring and g is 0 then $R_2$ is not H, and with the further proviso that when the condensed thiazole ring is attached at the 2-position of the benzothiophene ring and g is other than 0 then $R_1$ is not attached at the 3-position of the benzothiophene ring.

It will be understood that the term halo, when used herein, includes fluoro, chloro, bromo and iodo. It will be understood that in alkyl groups, alkenyl groups, alkynyl groups, alkylthio groups and alkoxy groups containing more than two carbon atoms the alkyl group may be straight or branched. Aryl means phenyl optionally substituted by one or more of the following: halo, a $C_{1-3}$ alkyl group or a $C_{1-3}$ alkoxy group.

Preferred values of $R_1$ are methyl, ethyl, propyl, isopropyl, cyclopropyl, methoxy, ethoxy, isopropoxy, bromo, chloro, fluoro, iodo, trifluoromethyl, trifluoromethoxy, methylthio, methylsulphinyl, methylsulphonyl, hydroxy, formyloxy, acetoxy, hydroxymethyl, 1-hydroxyethyl, 1-hydroxy-1-methylethyl, 1-hydroxypropyl, cyano, formyl, acetyl, methoxycarbonyl, ethoxycarbonyl, carbamoyl, carbamoylmethyl, sulphamoyl, sulphamoylmethyl, amino, methylamino, dimethylamino, ethylamino or diethylamino. More preferably $R_1$ is methyl, methoxy, chloro, fluoro or hydroxy.

Preferred values of $R_2$ are H, methyl, ethyl, propyl, isopropyl, cyclopropyl, butyl, methoxy, ethoxy, bromo, chloro, fluoro, iodo, trifluoromethyl, trifluoromethoxy hydroxymethyl, 1-hydroxyethyl, 1-hydroxy-1-methylethyl; 1-hydroxypropyl, 1-hydroxy-2-methylpropyl, 1-hydroxybutyl, 1-hydroxy-3-methylbutyl, 1-hydroxypentyl, 1-hydroxypropenyl, 1-hydroxybut-3-enyl, 1-hydroxy-2-methylpropenyl, 1-hydroxy-2-methylbut-3-enyl, 1-hydroxypent-4-enyl, 3-hydroxybut-1-enyl, 1-hydroxypropynyl, 1-hydroxybut-2-ynyl, α-hydroxy-2-methoxybenzyl, methoxymethyl, ethoxymethyl, isopropoxymethyl, cyclopropylmethoxymethyl, cyclobutylmethoxymethyl, prop-2-ynyloxymethyl, methylthio, phenylthio, vinyl, allyl, prop-1-enyl, 2-methylprop-2-enyl, 1-methylvinyl, styryl, formyl, acetyl, cyano, ethoxycarbonylmethyl, N-(1-methylethyl)iminomethyl, N-methylaminomethyl and hydroxyiminomethyl. More preferably $R_2$ is H, hydroxymethyl, methyl, ethyl, isopropyl, methylthio, cyclopropyl, allyl and vinyl, such as, for example, H, hydroxymethyl, methyl, ethyl, isopropyl or methylthio. Most preferably $R_2$ is hydroxymethyl, methyl or ethyl.

In a first preferred group of compounds of Formula I:

g is 0, 1 or 2;
n is 2 or 3;
$R_1$ is halo, an alkyl group containing 1 to 3 carbon atoms, an alkoxy group containing 1 to 3 carbon atoms or hydroxy; and
$R_2$ represents H, an alkyl group containing 1 to 3 carbon atoms, a hydroxyalkyl group containing 1 to 6 carbon atoms, a $C_{1-3}$alkylthio group, a cycloalkyl group containing 3 to 6 carbon atoms, or an alkenyl group containing 2 to 8 carbon atoms. More preferably, $R_2$ represents H, an alkyl group containing 1 to 3 carbon atoms, a hydroxyalkyl group containing 1 to 6 carbon atoms or a $C_{1-3}$alkylthio group.
More preferably g is 0 or 1. More preferably n is 2.
A second preferred group of compounds of Formula I is represented by Formula II

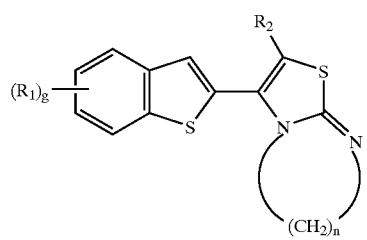

in which $R_1$, $R_2$, n and g are as initially defined.

A third preferred group of compounds of Formula I is represented by Formula III

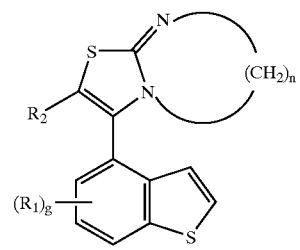

in which $R_1$, $R_2$, n and g are as initially defined.

A fourth preferred group of compounds of Formula I is represented by Formula IV

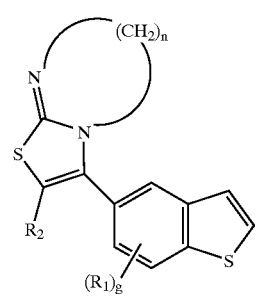

in which $R_1$, $R_2$, n and g are as initially defined.

A fifth preferred group of compounds of Formula I is represented by Formula V

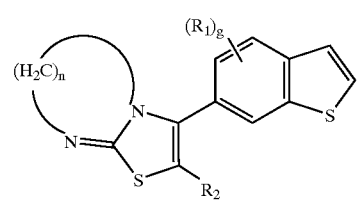

in which $R_1$, $R_2$, n and g are as initially defined.

A sixth preferred group of compounds of Formula I is represented by Formula VI

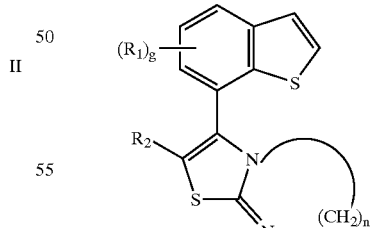

in which $R_1$, $R_2$, n and g are as initially defined.

Preferably in compounds of Formulae II, III, IV, V and VI
g is 0, 1 or 2;
n is 2 or 3;
$R_1$ is halo, an alkyl group containing 1 to 3 carbon atoms, an alkoxy group containing 1 to 3 carbon atoms or hydroxy; and $R_2$ represents H, an alkyl group containing 1 to 3 carbon atoms, a hydroxyalkyl group containing 1 to 6 carbon atoms, a $C_{1-3}$alkylthio group, a cycloalkyl group containing 3 to 6 carbon atoms, or an alkenyl group containing 2 to 8 carbon atoms.

Preferably, $R_2$ represents H, an alkyl group containing 1 to 3 carbon atoms, a hydroxyalkyl group containing 1 to 6 carbon atoms or a $C_{1-3}$alkylthio group. More preferably n is 2.

More preferably in compounds of Formula II, g is 0, 1 or 2, n is 2, $R_1$ is fluoro, chloro, hydroxy, methyl or methoxy, with the proviso that, when g is other than 0, $R_1$ is not attached at the 3-position of the benzo[b]thiophene ring; and $R_2$ represents H, methyl, ethyl, hydroxymethyl or methylthio, with the proviso that, when g is 0, $R_2$ is not H.

More preferably in compounds of Formula II, g is 0 or 1, n is 2 and $R_2$ represents H, an alkyl group containing 1 to 3 carbon atoms, a hydroxyalkyl group containing 1 to 6 carbon atoms, a $C_{1-3}$alkylthio group, a cycloalkyl group containing 3 to 6 carbon atoms, or an alkenyl group containing 2 to 8 carbon atoms. Even more preferably, $R_1$ is fluoro or methyl and/or $R_2$ represents H, an alkyl group containing 1 to 3 carbon atoms, a hydroxyalkyl group containing 1 to 6 carbon atoms or a $C_{1-3}$alkylthio group. Most preferably $R_2$ is H, methyl, ethyl, hydroxymethyl, methylthio, isopropyl, allyl or vinyl; such as, for example, H, methyl, ethyl, hydroxymethyl or methylthio.

More preferably in compounds of Formula IV, g is 0, n is 2; and $R_2$ represents an alkyl group containing 1 to 3 carbon atoms, a hydroxyalkyl group containing 1 to 6 carbon atoms, or a $C_{1-3}$alkylthio group. Most preferably $R_2$ is methyl, ethyl, isopropyl, hydroxymethyl or methylthio.

More preferably in compounds of Formula V, g is 0, n is 2, and $R_2$ represents H, an alkyl group containing 1 to 3 carbon atoms, a hydroxyalkyl group containing 1 to 6 carbon atoms, or a $C_{1-3}$alkylthio group. Most preferably $R_2$ is methyl.

More preferably in compounds of Formula VI, g is 0, n is 2, and $R_2$ represents H, an alkyl group containing 1 to 3 carbon atoms, a hydroxyalkyl group containing 1 to 6 carbon atoms, or a $C_{1-3}$alkylthio group. Most preferably $R_2$ is methyl.

Compounds of Formula I may exist as salts with pharmaceutically acceptable acids. The present invention includes all such salts. Examples of such salts include hydrochlorides, hydrobromides, sulphates, methanesulphonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

Certain compounds of Formula I may exist in different tautomeric forms or as different geometric isomers, and the present invention includes each tautomer and/or geometric isomer of compounds of Formula I and mixtures thereof.

Certain compounds of Formula I may exist in different stable conformational forms which may be separable. For example, if $R_2$ is a bulky group there may be restricted rotation about one or more single bond or bonds due to steric hindrance. Torsional asymmetry due to restricted rotation about an asymmetric single bond, for example because of steric hindrance or ring strain, may permit separation of different conformers. The present invention includes each conformational isomer of compounds of Formula I and mixtures thereof.

Certain compounds of Formula I and their salts may exist in more than one crystal form and the present invention includes each crystal form and mixtures thereof. Certain compounds of Formula I and their salts may also exist in the form of solvates, for example hydrates, and the present invention includes each solvate and mixtures thereof.

Certain compounds of Formula I contain one or more chiral centres, and exist in different optically active forms. When compounds of Formula I contain one chiral centre, the compounds exist in two enantiomeric forms and the present invention includes both enantiomers and mixtures of enantiomers. The enantiomers may be resolved by methods known to those skilled in the art, for example by formation of diastereoisomeric salts which may be separated, for example, by crystallisation; formation of diastereoisomeric derivatives or complexes which may be separated, for example, by crystallisation, gas-liquid or liquid chromatography; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesised by asymmetric synthesis using optically active reagents, substrates, catalysts or solvents, or by converting one enantiomer into the other by asymmetric transformation.

When a compound of Formula I contains more than one chiral centre it may exist in diastereoisomeric forms. The diastereoisomeric pairs may be separated by methods known to those skilled in the art, for example chromatography or crystallisation and the individual enantiomers within each pair may be separated as described above. The present invention includes each diastereoisomer of compounds of Formula I and mixtures thereof.

Specific compounds of Formula I are given in List 1.

List 1

3-(4-chlorobenzo[b]thiophen-2-yl)-5,6-dihydroimidazo[2,1-b]thiazole 3-(benzo[b]thiophen-4-yl)-5,6-dihydroimidazo[2,1-b]thiazole

[3-(benzo[b]thiophen-4-yl)-5,6-dihydroimidazo[2,1-b]thiazol-2-yl]methanol

[3-(4-chlorobenzo[b]thiophen-2-yl)-5,6-dihydroimidazo[2,1-b]thiazol-2-yl]methanol 3-(4-fluorobenzo[b]thiophen-2-yl)-5,6-dihydroimidazo[2,1-b]thiazole 3-(benzo[b]thiophen-2-yl)-2-methyl-5,6-dihydroimidazo[2,1-b]thiazole 3-(4-fluorobenzo[b]thiophen-2-yl)-2-methyl-5,6-dihydroimidazo[2,1-b]thiazole 3-(benzo[b]thiophen-4-yl)-2-methyl-5,6-dihydroimidazo[2,1-b]thiazole 3-(4-chlorobenzo[b]thiophen-2-yl)-2-methyl-5,6-dihydroimidazo[2,1-b]thiazole 3-(5-chlorobenzo[b]thiophen-2-yl)-2-ethyl-5,6-dihydroimidazo[2,1-b]thiazole 2-(5,6-dihydroimidazo[2,1-b]thiazol-3-yl)benzo[b]thiophen-4-ol 3-(benzo[b]thiophen-4-yl)-2-ethyl-5,6-dihydroimidazo[2,1-b]thiazole 3-(4-methylbenzo[b]thiophen-2-yl)-5,6-dihydroimidazo[2,1-b]thiazole

[3-(benzo[b]thiophen-2-yl)-5,6-dihydroimidazo[2,1-b]thiazol-2-yl]methanol 2-methyl-3-(4-methylbenzo[b]thiophen-2-yl)-5,6-dihydroimidazo[2,1-b]thiazole 3-(4-chlorobenzo[b]thiophen-2-yl)-2-methyl-6,7-dihydro-5H-thiazolo[3,2-a]pyrimidine 3-(4-chlorobenzo[b]thiophen-2-yl)-2-ethyl-5,6-dihydroimidazo[2,1-b]thiazole 3-(benzo[b]thiophen-2-yl)-2-(methylthio)-5,6-dihydroimidazo[2,1-b]thiazole
3-(7-chlorobenzo[b]thiophen-2-yl)-2-methyl-5,6-dihydroimidazo[2,1-b]thiazole
3-(benzo[b]thiophen-5-yl)-2-methyl-5,6-dihydroimidazo[2,1-b]thiazole
3-(benzo[b]thiophen-4-yl)-2-(methylthio)-5,6-dihydroimidazo[2,1-b]thiazole
3-(benzo[b]thiophen-7-yl)-2-methyl-5,6-dihydroimidazo[2,1-b]thiazole
3-(4,5-dichlorobenzo[b]thiophen-2-yl)-2-methyl-5,6-dihydroimidazo[2,1-b]thiazole
3-(7-methoxybenzo[b]thiophen-2-yl)-2-methyl-5,6-dihydroimidazo[2,1-b]thiazole
3-(5-fluorobenzo[b]thiophen-2-yl)-2-methyl-5,6-dihydroimidazo[2,1-b]thiazole
[3-(benzo[b]thiophen-5-yl)-5,6-dihydroimidazo[2,1-b]thiazol-2-yl]methanol
3-(benzo[b]thiophen-5-yl)-2-(1-methylethyl)-5,6-dihydroimidazo[2,1-b]thiazole
3-(benzo[b]thiophen-5-yl)-2-(methylthio)-5,6-dihydroimidazo[2,1-b]thiazole
3-(benzo[b]thiophen-5-yl)-2-ethyl-5,6-dihydroimidazo[2,1-b]thiazole
3-(benzo[b]thiophen-4-yl)-2-cyclopropyl-5,6-dihydroimidazo[2,1-b]thiazole
2-methyl-3-(2-methylbenzo[b]thiophen-4-yl)-5,6-dihydroimidazo[2,1-b]thiazole
3-(benzo[b]thiophen-4-yl)-2-(1-methylethyl)-5,6-dihydroimidazo[2,1-b]thiazole
2-allyl-3-(benzo[b]thiophen-4-yl)-5,6-dihydroimidazo[2,1-b]thiazole
3-(benzo[b]thiophen-6-yl)-2-methyl-5,6-dihydroimidazo[2,1-b]thiazole
3-(7-fluorobenzo[b]thiophen-4-yl)-2-methyl-5,6-dihydroimidazo[2,1-b]thiazole
3-(benzo[b]thiophen-4-yl)-2-vinyl-5,6-dihydroimidazo[2,1-b]thiazole
3-(benzo[b]thiophen-2-yl)-2-ethyl-5,6-dihydroimidazo[2,1-b]thiazole
3-(benzo[b]thiophen-2-yl)-2-propyl-5,6-dihydroimidazo[2,1-b]thiazole
3-(benzo[b]thiophen-2-yl)-2-(1-methylethyl)-5,6-dihydroimidazo[2,1-b]thiazole
3-(benzo[b]thiophen-2-yl)-2-cyclopropyl-5,6-dihydroimidazo[2,1-b]thiazole
3-(benzo[b]thiophen-2-yl)-2-vinyl-5,6-dihydroimidazo[2,1-b]thiazole
3-(benzo[b]thiophen-2-yl)-2-methoxymethyl-5,6-dihydroimidazo[2,1-b]thiazole
1-[3-(benzo[b]thiophen-2-yl)-5,6-dihydroimidazo[2,1-b]thiazol-2-yl]ethanol
2-[3-(benzo[b]thiophen-2-yl)-5,6-dihydroimidazo[2,1-b]thiazol-2-yl]ethanol
3-(4-chlorobenzo[b]thiophen-2-yl)-2-propyl-5,6-dihydroimidazo[2,1-b]thiazole
3-(4-chlorobenzo[b]thiophen-2-yl)-2-(1-methylethyl)-5,6-dihydroimidazo[2,1-b]thiazole
3-(4-chlorobenzo[b]thiophen-2-yl)-2-cyclopropyl-5,6-dihydroimidazo[2,1-b]thiazole
3-(4-chlorobenzo[b]thiophen-2-yl)-2-vinyl-5,6-dihydroimidazo[2,1-b]thiazole
3-(4-chlorobenzo[b]thiophen-2-yl)-2-(methylthio)-5,6-dihydroimidazo[2,1-b]thiazole
1-[3-(4-chlorobenzo[b]thiophen-2-yl)-5,6-dihydroimidazo[2,1-b]thiazol-2-yl]ethanol
2-[3-(4-chlorobenzo[b]thiophen-2-yl)-5,6-dihydroimidazo[2,1-b]thiazol-2-yl]ethanol
3-(5-chlorobenzo[b]thiophen-2-yl)-2-methyl-5,6-dihydroimidazo[2,1-b]thiazole
3-(5-chlorobenzo[b]thiophen-2-yl)-2-propyl-5,6-dihydroimidazo[2,1-b]thiazole
3-(5-chlorobenzo[b]thiophen-2-yl)-2-(1-methylethyl)-5,6-dihydroimidazo[2,1-b]thiazole
3-(5-chlorobenzo[b]thiophen-2-yl)-2-cyclopropyl-5,6-dihydroimidazo[2,1-b]thiazole
3-(5-chlorobenzo[b]thiophen-2-yl)-2-vinyl-5,6-dihydroimidazo[2,1-b]thiazole
3-(5-chlorobenzo[b]thiophen-2-yl)-2-(methylthio)-5,6-dihydroimidazo[2,1-b]thiazole
[3-(5-chlorobenzo[b]thiophen-2-yl)-5,6-dihydroimidazo[2,1-b]thiazol-2-yl]methanol
1-[3-(5-chlorobenzo[b]thiophen-2-yl)-5,6-dihydroimidazo[2,1-b]thiazol-2-yl]ethanol
2-[3-(5-chlorobenzo[b]thiophen-2-yl)-5,6-dihydroimidazo[2,1-b]thiazol-2-yl]ethanol
3-(6-chlorobenzo[b]thiophen-2-yl)-2-methyl-5,6-dihydroimidazo[2,1-b]thiazole
3-(6-chlorobenzo[b]thiophen-2-yl)-2-ethyl-5,6-dihydroimidazo[2,1-b]thiazole
3-(6-chlorobenzo[b]thiophen-2-yl)-2-propyl-5,6-dihydroimidazo[2,1-b]thiazole
3-(6-chlorobenzo[b]thiophen-2-yl)-2-(1-methylethyl)-5,6-dihydroimidazo[2,1-b]thiazole
3-(6-chlorobenzo[b]thiophen-2-yl)-2-cyclopropyl-5,6-dihydroimidazo[2,1-b]thiazole
3-(6-chlorobenzo[b]thiophen-2-yl)-2-vinyl-5,6-dihydroimidazo[2,1-b]thiazole
3-(6-chlorobenzo[b]thiophen-2-yl)-2-(methylthio)-5,6-dihydroimidazo[2,1-b]thiazole
[3-(6-chlorobenzo[b]thiophen-2-yl)-5,6-dihydroimidazo[2,1-b]thiazol-2-yl]methanol
1-[3-(6-chlorobenzo[b]thiophen-2-yl)-5,6-dihydroimidazo[2,1-b]thiazol-2-yl]ethanol
2-[3-(6-chlorobenzo[b]thiophen-2-yl)-5,6-dihydroimidazo[2,1-b]thiazol-2-yl]ethanol
3-(7-chlorobenzo[b]thiophen-2-yl)-2-ethyl-5,6-dihydroimidazo[2,1-b]thiazole
3-(7-chlorobenzo[b]thiophen-2-yl)-2-propyl-5,6-dihydroimidazo[2,1-b]thiazole
3-(7-chlorobenzo[b]thiophen-2-yl)-2-(1-methylethyl)-5,6-dihydroimidazo[2,1-b]thiazole
3-(7-chlorobenzo[b]thiophen-2-yl)-2-cyclopropyl-5,6-dihydroimidazo[2,1-b]thiazole
3-(7-chlorobenzo[b]thiophen-2-yl)-2-vinyl-5,6-dihydroimidazo[2,1-b]thiazole
3-(7-chlorobenzo[b]thiophen-2-yl)-2-(methylthio)-5,6-dihydroimidazo[2,1-b]thiazole
[3-(7-chlorobenzo[b]thiophen-2-yl)-5,6-dihydroimidazo[2,1-b]thiazol-2-yl]methanol
1-[3-(7-chlorobenzo[b]thiophen-2-yl)-5,6-dihydroimidazo[2,1-b]thiazol-2-yl]ethanol
2-[3-(7-chlorobenzo[b]thiophen-2-yl)-5,6-dihydroimidazo[2,1-b]thiazol-2-yl]ethanol
3-(4-fluorobenzo[b]thiophen-2-yl)-2-ethyl-5,6-dihydroimidazo[2,1-b]thiazole
3-(4-fluorobenzo[b]thiophen-2-yl)-2-propyl-5,6-dihydroimidazo[2,1-b]thiazole
3-(4-fluorobenzo[b]thiophen-2-yl)-2-(1-methylethyl)-5,6-dihydroimidazo[2,1-b]thiazole
3-(4-fluorobenzo[b]thiophen-2-yl)-2-cyclopropyl-5,6-dihydroimidazo[2,1-b]thiazole
3-(4-fluorobenzo[b]thiophen-2-yl)-2-vinyl-5,6-dihydroimidazo[2,1-b]thiazole
3-(4-fluorobenzo[b]thiophen-2-yl)-2-methoxymethyl-5,6-dihydroimidazo[2,1-b]thiazole 3-(4-fluorobenzo[b]thiophen-2-yl)-2-(methylthio)-5,6-dihydroimidazo[2,1-b]thiazole
1-[3-(4-fluorobenzo[b]thiophen-2-yl)-5,6-dihydroimidazo[2,1-b]thiazol-2-yl]ethanol
2-[3-(4-fluorobenzo[b]thiophen-2-yl)-5,6-dihydroimidazo[2,1-b]thiazol-2-yl]ethanol
3-(5-fluorobenzo[b]thiophen-2-yl)-2-ethyl-5,6-dihydroimidazo[2,1-b]thiazole
3-(5-fluorobenzo[b]thiophen-2-yl)-2-propyl-5,6-dihydroimidazo[2,1-b]thiazole
3-(5-fluorobenzo[b]thiophen-2-yl)-2-(1-methylethyl)-5,6-dihydroimidazo[2,1-b]thiazole
3-(5-fluorobenzo[b]thiophen-2-yl)-2-cyclopropyl-5,6-dihydroimidazo[2,1-b]thiazole
3-(5-fluorobenzo[b]thiophen-2-yl)-2-vinyl-5,6-dihydroimidazo[2,1-b]thiazole
3-(5-fluorobenzo[b]thiophen-2-yl)-2-(methylthio)-5,6-dihydroimidazo[2,1-b]thiazole
[3-(5-fluorobenzo[b]thiophen-2-yl)-5,6-dihydroimidazo[2,1-b]thiazol-2-yl]methanol
1-[3-(5-fluorobenzo[b]thiophen-2-yl)-5,6-dihydroimidazo[2,1-b]thiazol-2-yl]ethanol
2-[3-(5-fluorobenzo[b]thiophen-2-yl)-5,6-dihydroimidazo[2,1-b]thiazol-2-yl]ethanol
3-(6-fluorobenzo[b]thiophen-2-yl)-2-methyl-5,6-dihydroimidazo[2,1-b]thiazole
3-(6-fluorobenzo[b]thiophen-2-yl)-2-ethyl-5,6-dihydroimidazo[2,1-b]thiazole
3-(6-fluorobenzo[b]thiophen-2-yl)-2-propyl-5,6-dihydroimidazo[2,1-b]thiazole
3-(6-fluorobenzo[b]thiophen-2-yl)-2-(1-methylethyl)-5,6-dihydroimidazo[2,1-b]thiazole
3-(6-fluorobenzo[b]thiophen-2-yl)-2-cyclopropyl-5,6-dihydroimidazo[2,1-b]thiazole
3-(6-fluorobenzo[b]thiophen-2-yl)-2-vinyl-5,6-dihydroimidazo[2,1-b]thiazole
3-(6-fluorobenzo[b]thiophen-2-yl)-2-(methylthio)-5,6-dihydroimidazo[2,1-b]thiazole
[3-(6-fluorobenzo[b]thiophen-2-yl)-5,6-dihydroimidazo[2,1-b]thiazol-2-yl]methanol
1-[3-(6-fluorobenzo[b]thiophen-2-yl)-5,6-dihydroimidazo[2,1-b]thiazol-2-yl]ethanol
2-[3-(6-fluorobenzo[b]thiophen-2-yl)-5,6-dihydroimidazo[2,1-b]thiazol-2-yl]ethanol
3-(7-fluorobenzo[b]thiophen-2-yl)-2-methyl-5,6-dihydroimidazo[2,1-b]thiazole
3-(7-fluorobenzo[b]thiophen-2-yl)-2-ethyl-5,6-dihydroimidazo[2,1-b]thiazole
3-(7-fluorobenzo[b]thiophen-2-yl)-2-propyl-5,6-dihydroimidazo[2,1-b]thiazole
3-(7-fluorobenzo[b]thiophen-2-yl)-2-(1-methylethyl)-5,6-dihydroimidazo[2,1-b]thiazole
3-(7-fluorobenzo[b]thiophen-2-yl)-2-cyclopropyl-5,6-dihydroimidazo[2,1-b]thiazole
3-(7-fluorobenzo[b]thiophen-2-yl)-2-vinyl-5,6-dihydroimidazo[2,1-b]thiazole
3-(7-fluorobenzo[b]thiophen-2-yl)-2-(methylthio)-5,6-dihydroimidazo[2,1-b]thiazole
[3-(7-fluorobenzo[b]thiophen-2-yl)-5,6-dihydroimidazo[2,1-b]thiazol-2-yl]methanol
1-[3-(7-fluorobenzo[b]thiophen-2-yl)-5,6-dihydroimidazo[2,1-b]thiazol-2-yl]ethanol
2-[3-(7-fluorobenzo[b]thiophen-2-yl)-5,6-dihydroimidazo[2,1-b]thiazol-2-yl]ethanol
3-(4-methoxybenzo[b]thiophen-2-yl)-2-methyl-5,6-dihydroimidazo[2,1-b]thiazole
2-ethyl-3-(4-methoxybenzo[b]thiophen-2-yl)-5,6-dihydroimidazo[2,1-b]thiazole
3-(4-methoxybenzo[b]thiophen-2-yl)-2-propyl-5,6-dihydroimidazo[2,1-b]thiazole
3-(4-methoxybenzo[b]thiophen-2-yl)-2-(1-methylethyl)-5,6-dihydroimidazo[2,1-b]thiazole
2-cyclopropyl-3-(4-methoxybenzo[b]thiophen-2-yl)-5,6-dihydroimidazo[2,1-b]thiazole
3-(4-methoxybenzo[b]thiophen-2-yl)-2-vinyl-5,6-dihydroimidazo[2,1-b]thiazole
3-(4-methoxybenzo[b]thiophen-2-yl)-2-(methylthio)-5,6-dihydroimidazo[2,1-b]thiazole
[3-(4-methoxybenzo[b]thiophen-2-yl)-5,6-dihydroimidazo[2,1-b]thiazol-2-yl]methanol
1-[3-(4-methoxybenzo[b]thiophen-2-yl)-5,6-dihydroimidazo[2,1-b]thiazol-2-yl]ethanol
2-[3-(4-methoxybenzo[b]thiophen-2-yl)-5,6-dihydroimidazo[2,1-b]thiazol-2-yl]ethanol
3-(5-methoxybenzo[b]thiophen-2-yl)-2-methyl-5,6-dihydroimidazo[2,1-b]thiazole
2-ethyl-3-(5-methoxybenzo[b]thiophen-2-yl)-5,6-dihydroimidazo[2,1-b]thiazole
3-(5-methoxybenzo[b]thiophen-2-yl)-2-propyl-5,6-dihydroimidazo[2,1-b]thiazole
3-(5-methoxybenzo[b]thiophen-2-yl)-2-(1-methylethyl)-5,6-dihydroimidazo[2,1-b]thiazole
2-cyclopropyl-3-(5-methoxybenzo[b]thiophen-2-yl)-5,6-dihydroimidazo[2,1-b]thiazole
3-(5-methoxybenzo[b]thiophen-2-yl)-2-vinyl-5,6-dihydroimidazo[2,1-b]thiazole
3-(5-methoxybenzo[b]thiophen-2-yl)-2-(methylthio)-5,6-dihydroimidazo[2,1-b]thiazole
[3-(5-methoxybenzo[b]thiophen-2-yl)-5,6-dihydroimidazo[2,1-b]thiazol-2-yl]methanol
1-[3-(5-methoxybenzo[b]thiophen-2-yl)-5,6-dihydroimidazo[2,1-b]thiazol-2-yl]ethanol
2-[3-(5-methoxybenzo[b]thiophen-2-yl)-5,6-dihydroimidazo[2,1-b]thiazol-2-yl]ethanol
3-(6-methoxybenzo[b]thiophen-2-yl)-2-methyl-5,6-dihydroimidazo[2,1-b]thiazole
2-ethyl-3-(6-methoxybenzo[b]thiophen-2-yl)-5,6-dihydroimidazo[2,1-b]thiazole
3-(6-methoxybenzo[b]thiophen-2-yl)-2-propyl-5,6-dihydroimidazo[2,1-b]thiazole
3-(6-methoxybenzo[b]thiophen-2-yl)-2-(1-methylethyl)-5,6-dihydroimidazo[2,1-b]thiazole
2-cyclopropyl-3-(6-methoxybenzo[b]thiophen-2-yl)-5,6-dihydroimidazo[2,1-b]thiazole
3-(6-methoxybenzo[b]thiophen-2-yl)-2-vinyl-5,6-dihydroimidazo[2,1-b]thiazole
3-(6-methoxybenzo[b]thiophen-2-yl)-2-(methylthio)-5,6-dihydroimidazo[2,1-b]thiazole
[3-(6-methoxybenzo[b]thiophen-2-yl)-5,6-dihydroimidazo[2,1-b]thiazol-2-yl]methanol
1-[3-(6-methoxybenzo[b]thiophen-2-yl)-5,6-dihydroimidazo[2,1-b]thiazol-2-yl]ethanol
2-[3-(6-methoxybenzo[b]thiophen-2-yl)-5,6-dihydroimidazo[2,1-b]thiazol-2-yl]ethanol
2-ethyl-3-(7-methoxybenzo[b]thiophen-2-yl)-5,6-dihydroimidazo[2,1-b]thiazole
3-(7-methoxybenzo[b]thiophen-2-yl)-2-propyl-5,6-dihydroimidazo[2,1-b]thiazole
3-(7-methoxybenzo[b]thiophen-2-yl)-2-(1-methylethyl)-5,6-dihydroimidazo[2,1-b]thiazole
2-cyclopropyl-3-(7-methoxybenzo[b]thiophen-2-yl)-5,6-dihydroimidazo[2,1-b]thiazole
3-(7-methoxybenzo[b]thiophen-2-yl)-2-vinyl-5,6-dihydroimidazo[2,1-b]thiazole
3-(7-methoxybenzo[b]thiophen-2-yl)-2-(methylthio)-5,6-dihydroimidazo[2,1-b]thiazole

[3-(7-methoxybenzo[b]thiophen-2-yl)-5,6-dihydroimidazo [2,1-b]thiazol-2-yl]methanol
1-[3-(7-methoxybenzo[b]thiophen-2-yl)-5,6-dihydroimidazo[2,1-b]thiazol-2-yl]ethanol
2-[3-(7-methoxybenzo[b]thiophen-2-yl)-5,6-dihydroimidazo[2,1-b]thiazol-2-yl]ethanol
2-ethyl-3-(4-methylbenzo[b]thiophen-2-yl)-5,6-dihydroimidazo[2,1-b]thiazole
3-(4-methylbenzo[b]thiophen-2-yl)-2-propyl-5,6-dihydroimidazo[2,1-b]thiazole
3-(4-methylbenzo[b]thiophen-2-yl)-2-(1-methylethyl)-5,6-dihydroimidazo[2,1-b]thiazole
2-cyclopropyl-3-(4-methylbenzo[b]thiophen-2-yl)-5,6-dihydroimidazo[2,1-b]thiazole
3-(4-methylbenzo[b]thiophen-2-yl)-2-vinyl-5,6-dihydroimidazo[2,1-b]thiazole
3-(4-methylbenzo[b]thiophen-2-yl)-2-(methylthio)-5,6-dihydroimidazo[2,1-b]thiazole
[3-(4-methylbenzo[b]thiophen-2-yl)-5,6-dihydroimidazo[2,1-b]thiazol-2-yl]methanol
1-[3-(4-methylbenzo[b]thiophen-2-yl)-5,6-dihydroimidazo[2,1-b]thiazol-2-yl]ethanol
2-[3-(4-methylbenzo[b]thiophen-2-yl)-5,6-dihydroimidazo[2,1-b]thiazol-2-yl]ethanol
2-methyl-3-(5-methylbenzo[b]thiophen-2-yl)-5,6-dihydroimidazo[2,1-b]thiazole
2-ethyl-3-(5-methylbenzo[b]thiophen-2-yl)-5,6-dihydroimidazo[2,1-b]thiazole
3-(5-methylbenzo[b]thiophen-2-yl)-2-propyl-5,6-dihydroimidazo[2,1-b]thiazole
3-(5-methylbenzo[b]thiophen-2-yl)-2-(1-methylethyl)-5,6-dihydroimidazo[2,1-b]thiazole
2-cyclopropyl-3-(5-methylbenzo[b]thiophen-2-yl)-5,6-dihydroimidazo[2,1-b]thiazole
3-(5-methylbenzo[b]thiophen-2-yl)-2-vinyl-5,6-dihydroimidazo[2,1-b]thiazole
3-(5-methylbenzo[b]thiophen-2-yl)-2-(methylthio)-5,6-dihydroimidazo[2,1-b]thiazole
[3-(5-methylbenzo[b]thiophen-2-yl)-5,6-dihydroimidazo[2,1-b]thiazol-2-yl]methanol
1-[3-(5-methylbenzo[b]thiophen-2-yl)-5,6-dihydroimidazo[2,1-b]thiazol-2-yl]ethanol
2-[3-(5-methylbenzo[b]thiophen-2-yl)-5,6-dihydroimidazo[2,1-b]thiazol-2-yl]ethanol
2-methyl-3-(6-methylbenzo[b]thiophen-2-yl)-5,6-dihydroimidazo[2,1-b]thiazole
2-ethyl-3-(6-methylbenzo[b]thiophen-2-yl)-5,6-dihydroimidazo[2,1-b]thiazole
3-(6-methylbenzo[b]thiophen-2-yl)-2-propyl-5,6-dihydroimidazo[2,1-b]thiazole
3-(6-methylbenzo[b]thiophen-2-yl)-2-(1-methylethyl)-5,6-dihydroimidazo[2,1-b]thiazole
2-cyclopropyl-3-(6-methylbenzo[b]thiophen-2-yl)-5,6-dihydroimidazo[2,1-b]thiazole
3-(6-methylbenzo[b]thiophen-2-yl)-2-vinyl-5,6-dihydroimidazo[2,1-b]thiazole
3-(6-methylbenzo[b]thiophen-2-yl)-2-(methylthio)-5,6-dihydroimidazo[2,1-b]thiazole
[3-(6-methylbenzo[b]thiophen-2-yl)-5,6-dihydroimidazo[2,1-b]thiazol-2-yl]methanol
1-[3-(6-methylbenzo[b]thiophen-2-yl)-5,6-dihydroimidazo[2,1-b]thiazol-2-yl]ethanol
2-[3-(6-methylbenzo[b]thiophen-2-yl)-5,6-dihydroimidazo[2,1-b]thiazol-2-yl]ethanol
2-methyl-3-(7-methylbenzo[b]thiophen-2-yl)-5,6-dihydroimidazo[2,1-b]thiazole
2-ethyl-3-(7-methylbenzo[b]thiophen-2-yl)-5,6-dihydroimidazo[2,1-b]thiazole
3-(7-methylbenzo[b]thiophen-2-yl)-2-propyl-5,6-dihydroimidazo[2,1-b]thiazole
3-(7-methylbenzo[b]thiophen-2-yl)-2-(1-methylethyl)-5,6-dihydroimidazo[2,1-b]thiazole
2-cyclopropyl-3-(7-methylbenzo[b]thiophen-2-yl)-5,6-dihydroimidazo[2,1-b]thiazole
3-(7-methylbenzo[b]thiophen-2-yl)-2-vinyl-5,6-dihydroimidazo[2,1-b]thiazole
3-(7-methylbenzo[b]thiophen-2-yl)-2-(methylthio)-5,6-dihydroimidazo[2,1-b]thiazole
[3-(7-methylbenzo[b]thiophen-2-yl)-5,6-dihydroimidazo[2,1-b]thiazol-2-yl]methanol
1-[3-(7-methylbenzo[b]thiophen-2-yl)-5,6-dihydroimidazo[2,1-b]thiazol-2-yl]ethanol
2-[3-(7-methylbenzo[b]thiophen-2-yl)-5,6-dihydroimidazo[2,1-b]thiazol-2-yl]ethanol
2-methyl-3-[4-(methylthio)benzo[b]thiophen-2-yl]-5,6-dihydroimidazo[2,1-b]thiazole
2-ethyl-3-[4-(methylthio)benzo[b]thiophen-2-yl]-5,6-dihydroimidazo[2,1-b]thiazole
3-[4-(methylthio)benzo[b]thiophen-2-yl]-2-propyl-5,6-dihydroimidazo[2,1-b]thiazole
2-(1-methylethyl)-3-[4-(methylthio)benzo[b]thiophen-2-yl]-5,6-dihydroimidazo[2,1-b]thiazole
2-cyclopropyl-3-[4-(methylthio)benzo[b]thiophen-2-yl]-5,6-dihydroimidazo[2,1-b]thiazole
3-[4-(methylthio)benzo[b]thiophen-2-yl]-2-vinyl-5,6-dihydroimidazo[2,1-b]thiazole
2-(methylthio)-3-[4-(methylthio)benzo[b]thiophen-2-yl]-5,6-dihydroimidazo[2,1-b]thiazole
[3-[4-(methylthio)benzo[b]thiophen-2-yl]-5,6-dihydroimidazo[2,1-b]thiazol-2-yl]methanol
1-[3-[4-(methylthio)benzo[b]thiophen-2-yl]-5,6-dihydroimidazo[2,1-b]thiazol-2-yl]ethanol
2-[3-[4-(methylthio)benzo[b]thiophen-2-yl]-5,6-dihydroimidazo[2,1-b]thiazol-2-yl]ethanol
2-methyl-3-[5-(methylthio)benzo[b]thiophen-2-yl]-5,6-dihydroimidazo[2,1-b]thiazole
2-ethyl-3-[5-(methylthio)benzo[b]thiophen-2-yl]-5,6-dihydroimidazo[2,1-b]thiazole
3-[5-(methylthio)benzo[b]thiophen-2-yl]-2-propyl-5,6-dihydroimidazo[2,1-b]thiazole
2-(1-methylethyl)-3-[5-(methylthio)benzo[b]thiophen-2-yl]-5,6-dihydroimidazo[2,1-b]thiazole
2-cyclopropyl-3-[5-(methylthio)benzo[b]thiophen-2-yl]-5,6-dihydroimidazo[2,1-b]thiazole
3-[5-(methylthio)benzo[b]thiophen-2-yl]-2-vinyl-5,6-dihydroimidazo[2,1-b]thiazole
2-(methylthio)-3-[5-(methylthio)benzo[b]thiophen-2-yl]-5,6-dihydroimidazo[2,1-b]thiazole
[3-[5-(methylthio)benzo[b]thiophen-2-yl]-5,6-dihydroimidazo[2,1-b]thiazol-2-yl]methanol
1-[3-[5-(methylthio)benzo[b]thiophen-2-yl]-5,6-dihydroimidazo[2,1-b]thiazol-2-yl]ethanol
2-[3-[5-(methylthio)benzo[b]thiophen-2-yl]-5,6-dihydroimidazo[2,1-b]thiazol-2-yl]ethanol
2-methyl-3-[6-(methylthio)benzo[b]thiophen-2-yl]-5,6-dihydroimidazo[2,1-b]thiazole
2-ethyl-3-[6-(methylthio)benzo[b]thiophen-2-yl]-5,6-dihydroimidazo[2,1-b]thiazole
3-[6-(methylthio)benzo[b]thiophen-2-yl]-2-propyl-5,6-dihydroimidazo[2,1-b]thiazole
2-(1-methylethyl)-3-[6-(methylthio)benzo[b]thiophen-2-yl]-5,6-dihydroimidazo[2,1-b]thiazole
2-cyclopropyl-3-[6-(methylthio)benzo[b]thiophen-2-yl]-5,6-dihydroimidazo[2,1-b]thiazole
3-[6-(methylthio)benzo[b]thiophen-2-yl]-2-vinyl-5,6-dihydroimidazo[2,1-b]thiazole 2-(methylthio)-3-[6-(methylthio)benzo[b]thiophen-2-yl]-5,6-dihydroimidazo[2,1-b]thiazole
[3-[6-(methylthio)benzo[b]thiophen-2-yl]-5,6-dihydroimidazo[2,1-b]thiazol-2-yl]methanol
1-[3-[6-(methylthio)benzo[b]thiophen-2-yl]-5,6-dihydroimidazo[2,1-b]thiazol-2-yl]ethanol
2-[3-[6-(methylthio)benzo[b]thiophen-2-yl]-5,6-dihydroimidazo[2,1-b]thiazol-2-yl]ethanol
2-methyl-3-[7-(methylthio)benzo[b]thiophen-2-yl]-5,6-dihydroimidazo[2,1-b]thiazole
2-ethyl-3-[7-(methylthio)benzo[b]thiophen-2-yl]-5,6-dihydroimidazo[2,1-b]thiazole
3-[7-(methylthio)benzo[b]thiophen-2-yl]-2-propyl-5,6-dihydroimidazo[2,1-b]thiazole
2-(1-methylethyl)-3-[7-(methylthio)benzo[b]thiophen-2-yl]-5,6-dihydroimidazo[2,1-b]thiazole
2-cyclopropyl-3-[7-(methylthio)benzo[b]thiophen-2-yl]-5,6-dihydroimidazo[2,1-b]thiazole
3-[7-(methylthio)benzo[b]thiophen-2-yl]-2-vinyl-5,6-dihydroimidazo[2,1-b]thiazole
2-(methylthio)-3-[7-(methylthio)benzo[b]thiophen-2-yl]-5,6-dihydroimidazo[2,1-b]thiazole
[3-[7-(methylthio)benzo[b]thiophen-2-yl]-5,6-dihydroimidazo[2,1-b]thiazol-2-yl]methanol
1-[3-[7-(methylthio)benzo[b]thiophen-2-yl]-5,6-dihydroimidazo[2,1-b]thiazol-2-yl]ethanol
2-[3-[7-(methylthio)benzo[b]thiophen-2-yl]-5,6-dihydroimidazo[2,1-b]thiazol-2-yl]ethanol
3-(benzo[b]thiophen-4-yl)-2-propyl-5,6-dihydroimidazo[2,1-b]thiazole
1-[3-(benzo[b]thiophen-4-yl)-5,6-dihydroimidazo[2,1-b]thiazol-2-yl]ethanol
2-[3-(benzo[b]thiophen-4-yl)-5,6-dihydroimidazo[2,1-b]thiazol-2-yl]ethanol
3-(6-chlorobenzo[b]thiophen-4-yl)-2-methyl-5,6-dihydroimidazo[2,1-b]thiazole
3-(6-chlorobenzo[b]thiophen-4-yl)-2-ethyl-5,6-dihydroimidazo[2,1-b]thiazole
3-(6-chlorobenzo[b]thiophen-4-yl)-2-propyl-5,6-dihydroimidazo[2,1-b]thiazole
3-(6-chlorobenzo[b]thiophen-4-yl)-2-(1-methylethyl)-5,6-dihydroimidazo[2,1-b]thiazole
3-(6-chlorobenzo[b]thiophen-4-yl)-2-cyclopropyl-5,6-dihydroimidazo[2,1-b]thiazole
3-(6-chlorobenzo[b]thiophen-4-yl)-2-vinyl-5,6-dihydroimidazo[2,1-b]thiazole
3-(6-chlorobenzo[b]thiophen-4-yl)-2-(methylthio)-5,6-dihydroimidazo[2,1-b]thiazole
[3-(6-chlorobenzo[b]thiophen-4-yl)-5,6-dihydroimidazo[2,1-b]thiazol-2-yl]methanol
1-[3-(6-chlorobenzo[b]thiophen-4-yl)-5,6-dihydroimidazo[2,1-b]thiazol-2-yl]ethanol
2-[3-(6-chlorobenzo[b]thiophen-4-yl)-5,6-dihydroimidazo[2,1-b]thiazol-2-yl]ethanol
3-(7-chlorobenzo[b]thiophen-4-yl)-2-methyl-5,6-dihydroimidazo[2,1-b]thiazole
3-(7-chlorobenzo[b]thiophen-4-yl)-2-ethyl-5,6-dihydroimidazo[2,1-b]thiazole
3-(7-chlorobenzo[b]thiophen-4-yl)-2-propyl-5,6-dihydroimidazo[2,1-b]thiazole
3-(7-chlorobenzo[b]thiophen-4-yl)-2-(1-methylethyl)-5,6-dihydroimidazo[2,1-b]thiazole
3-(7-chlorobenzo[b]thiophen-4-yl)-2-cyclopropyl-5,6-dihydroimidazo[2,1-b]thiazole
3-(7-chlorobenzo[b]thiophen-4-yl)-2-vinyl-5,6-dihydroimidazo[2,1-b]thiazole
3-(7-chlorobenzo[b]thiophen-4-yl)-2-(methylthio)-5,6-dihydroimidazo[2,1-b]thiazole
[3-(7-chlorobenzo[b]thiophen-4-yl)-5,6-dihydroimidazo[2,1-b]thiazol-2-yl]methanol
1-[3-(7-chlorobenzo[b]thiophen-4-yl)-5,6-dihydroimidazo[2,1-b]thiazol-2-yl]ethanol
2-[3-(7-chlorobenzo[b]thiophen-4-yl)-5,6-dihydroimidazo[2,1-b]thiazol-2-yl]ethanol
3-(6-fluorobenzo[b]thiophen-4-yl)-2-methyl-5,6-dihydroimidazo[2,1-b]thiazole
3-(6-fluorobenzo[b]thiophen-4-yl)-2-ethyl-5,6-dihydroimidazo[2,1-b]thiazole
3-(6-fluorobenzo[b]thiophen-4-yl)-2-propyl-5,6-dihydroimidazo[2,1-b]thiazole
3-(6-fluorobenzo[b]thiophen-4-yl)-2-(1-methylethyl)-5,6-dihydroimidazo[2,1-b]thiazole
3-(6-fluorobenzo[b]thiophen-4-yl)-2-cyclopropyl-5,6-dihydroimidazo[2,1-b]thiazole
3-(6-fluorobenzo[b]thiophen-4-yl)-2-vinyl-5,6-dihydroimidazo[2,1-b]thiazole
3-(6-fluorobenzo[b]thiophen-4-yl)-2-(methylthio)-5,6-dihydroimidazo[2,1-b]thiazole
[3-(6-fluorobenzo[b]thiophen-4-yl)-5,6-dihydroimidazo[2,1-b]thiazol-2-yl]methanol
1-[3-(6-fluorobenzo[b]thiophen-4-yl)-5,6-dihydroimidazo[2,1-b]thiazol-2-yl]ethanol
2-[3-(6-fluorobenzo[b]thiophen-4-yl)-5,6-dihydroimidazo[2,1-b]thiazol-2-yl]ethanol
3-(7-fluorobenzo[b]thiophen-4-yl)-2-ethyl-5,6-dihydroimidazo[2,1-b]thiazole
3-(7-fluorobenzo[b]thiophen-4-yl)-2-propyl-5,6-dihydroimidazo[2,1-b]thiazole
3-(7-fluorobenzo[b]thiophen-4-yl)-2-(1-methylethyl)-5,6-dihydroimidazo[2,1-b]thiazole
3-(7-fluorobenzo[b]thiophen-4-yl)-2-cyclopropyl-5,6-dihydroimidazo[2,1-b]thiazole
3-(7-fluorobenzo[b]thiophen-4-yl)-2-vinyl-5,6-dihydroimidazo[2,1-b]thiazole
3-(7-fluorobenzo[b]thiophen-4-yl)-2-(methylthio)-5,6-dihydroimidazo[2,1-b]thiazole
[3-(7-fluorobenzo[b]thiophen-4-yl)-5,6-dihydroimidazo[2,1-b]thiazol-2-yl]methanol
1-[3-(7-fluorobenzo[b]thiophen-4-yl)-5,6-dihydroimidazo[2,1-b]thiazol-2-yl]ethanol
2-[3-(7-fluorobenzo[b]thiophen-4-yl)-5,6-dihydroimidazo[2,1-b]thiazol-2-yl]ethanol
3-(6-methoxybenzo[b]thiophen-4-yl)-2-methyl-5,6-dihydroimidazo[2,1-b]thiazole
2-ethyl-3-(6-methoxybenzo[b]thiophen-4-yl)-5,6-dihydroimidazo[2,1-b]thiazole
3-(6-methoxybenzo[b]thiophen-4-yl)-2-propyl-5,6-dihydroimidazo[2,1-b]thiazole
3-(6-methoxybenzo[b]thiophen-4-yl)-2-(1-methylethyl)-5,6-dihydroimidazo[2,1-b]thiazole
2-cyclopropyl-3-(6-methoxybenzo[b]thiophen-4-yl)-5,6-dihydroimidazo[2,1-b]thiazole
3-(6-methoxybenzo[b]thiophen-4-yl)-2-vinyl-5,6-dihydroimidazo[2,1-b]thiazole
3-(6-methoxybenzo[b]thiophen-4-yl)-2-(methylthio)-5,6-dihydroimidazo[2,1-b]thiazole
[3-(6-methoxybenzo[b]thiophen-4-yl)-5,6-dihydroimidazo[2,1-b]thiazol-2-yl]methanol
1-[3-(6-methoxybenzo[b]thiophen-4-yl)-5,6-dihydroimidazo[2,1-b]thiazol-2-yl]ethanol
2-[3-(6-methoxybenzo[b]thiophen-4-yl)-5,6-dihydroimidazo[2,1-b]thiazol-2-yl]ethanol
3-(7-methoxybenzo[b]thiophen-4-yl)-2-methyl-5,6-dihydroimidazo[2,1-b]thiazole
2-ethyl-3-(7-methoxybenzo[b]thiophen-4-yl)-5,6-dihydroimidazo[2,1-b]thiazole 3-(7-methoxybenzo[b]thiophen-4-yl)-2-propyl-5,6-dihydroimidazo[2,1-b]thiazole
3-(7-methoxybenzo[b]thiophen-4-yl)-2-(1-methylethyl)-5,6-dihydroimidazo[2,1-b]thiazole
2-cyclopropyl-3-(7-methoxybenzo[b]thiophen-4-yl)-5,6-dihydroimidazo[2,1-b]thiazole
3-(7-methoxybenzo[b]thiophen-4-yl)-2-vinyl-5,6-dihydroimidazo[2,1-b]thiazole
3-(7-methoxybenzo[b]thiophen-4-yl)-2-(methylthio)-5,6-dihydroimidazo[2,1-b]thiazole
[3-(7-methoxybenzo[b]thiophen-4-yl)-5,6-dihydroimidazo[2,1-b]thiazol-2-yl]methanol
1-[3-(7-methoxybenzo[b]thiophen-4-yl)-5,6-dihydroimidazo[2,1-b]thiazol-2-yl]ethanol
2-[3-(7-methoxybenzo[b]thiophen-4-yl)-5,6-dihydroimidazo[2,1-b]thiazol-2-yl]ethanol
2-ethyl-3-(2-methylbenzo[b]thiophen-4-yl)-5,6-dihydroimidazo[2,1-b]thiazole
3-(2-methylbenzo[b]thiophen-4-yl)-2-propyl-5,6-dihydroimidazo[2,1-b]thiazole
3-(2-methylbenzo[b]thiophen-4-yl)-2-(1-methylethyl)-5,6-dihydroimidazo[2,1-b]thiazole
2-cyclopropyl-3-(2-methylbenzo[b]thiophen-4-yl)-5,6-dihydroimidazo[2,1-b]thiazole
3-(2-methylbenzo[b]thiophen-4-yl)-2-vinyl-5,6-dihydroimidazo[2,1-b]thiazole
3-(2-methylbenzo[b]thiophen-4-yl)-2-(methylthio)-5,6-dihydroimidazo[2,1-b]thiazole
[3-(2-methylbenzo[b]thiophen-4-yl)-5,6-dihydroimidazo[2,1-b]thiazol-2-yl]methanol
1-[3-(2-methylbenzo[b]thiophen-4-yl)-5,6-dihydroimidazo[2,1-b]thiazol-2-yl]ethanol
2-[3-(2-methylbenzo[b]thiophen-4-yl)-5,6-dihydroimidazo[2,1-b]thiazol-2-yl]ethanol
2-methyl-3-(3-methylbenzo[b]thiophen-4-yl)-5,6-dihydroimidazo[2,1-b]thiazole
2-ethyl-3-(3-methylbenzo[b]thiophen-4-yl)-5,6-dihydroimidazo[2,1-b]thiazole
3-(3-methylbenzo[b]thiophen-4-yl)-2-propyl-5,6-dihydroimidazo[2,1-b]thiazole
3-(3-methylbenzo[b]thiophen-4-yl)-2-(1-methylethyl)-5,6-dihydroimidazo[2,1-b]thiazole
2-cyclopropyl-3-(3-methylbenzo[b]thiophen-4-yl)-5,6-dihydroimidazo[2,1-b]thiazole
3-(3-methylbenzo[b]thiophen-4-yl)-2-vinyl-5,6-dihydroimidazo[2,1-b]thiazole
3-(3-methylbenzo[b]thiophen-4-yl)-2-(methylthio)-5,6-dihydroimidazo[2,1-b]thiazole
[3-(3-methylbenzo[b]thiophen-4-yl)-5,6-dihydroimidazo[2,1-b]thiazol-2-yl]methanol
1-[3-(3-methylbenzo[b]thiophen-4-yl)-5,6-dihydroimidazo[2,1-b]thiazol-2-yl]ethanol
2-[3-(3-methylbenzo[b]thiophen-4-yl)-5,6-dihydroimidazo[2,1-b]thiazol-2-yl]ethanol
2-methyl-3-(6-methylbenzo[b]thiophen-4-yl)-5,6-dihydroimidazo[2,1-b]thiazole
2-ethyl-3-(6-methylbenzo[b]thiophen-4-yl)-5,6-dihydroimidazo[2,1-b]thiazole
3-(6-methylbenzo[b]thiophen-4-yl)-2-propyl-5,6-dihydroimidazo[2,1-b]thiazole
3-(6-methylbenzo[b]thiophen-4-yl)-2-(1-methylethyl)-5,6-dihydroimidazo[2,1-b]thiazole
2-cyclopropyl-3-(6-methylbenzo[b]thiophen-4-yl)-5,6-dihydroimidazo[2,1-b]thiazole
3-(6-methylbenzo[b]thiophen-4-yl)-2-vinyl-5,6-dihydroimidazo[2,1-b]thiazole
3-(6-methylbenzo[b]thiophen-4-yl)-2-(methylthio)-5,6-dihydroimidazo[2,1-b]thiazole
[3-(6-methylbenzo[b]thiophen-4-yl)-5,6-dihydroimidazo[2,1-b]thiazol-2-yl]methanol
1-[3-(6-methylbenzo[b]thiophen-4-yl)-5,6-dihydroimidazo[2,1-b]thiazol-2-yl]ethanol
2-[3-(6-methylbenzo[b]thiophen-4-yl)-5,6-dihydroimidazo[2,1-b]thiazol-2-yl]ethanol
2-methyl-3-(7-methylbenzo[b]thiophen-4-yl)-5,6-dihydroimidazo[2,1-b]thiazole
2-ethyl-3-(7-methylbenzo[b]thiophen-4-yl)-5,6-dihydroimidazo[2,1-b]thiazole
3-(7-methylbenzo[b]thiophen-4-yl)-2-propyl-5,6-dihydroimidazo[2,1-b]thiazole
3-(7-methylbenzo[b]thiophen-4-yl)-2-(1-methylethyl)-5,6-dihydroimidazo[2,1-b]thiazole
2-cyclopropyl-3-(7-methylbenzo[b]thiophen-4-yl)-5,6-dihydroimidazo[2,1-b]thiazole
3-(7-methylbenzo[b]thiophen-4-yl)-2-vinyl-5,6-dihydroimidazo[2,1-b]thiazole
3-(7-methylbenzo[b]thiophen-4-yl)-2-(methylthio)-5,6-dihydroimidazo[2,1-b]thiazole
[3-(7-methylbenzo[b]thiophen-4-yl)-5,6-dihydroimidazo[2,1-b]thiazol-2-yl]methanol
1-[3-(7-methylbenzo[b]thiophen-4-yl)-5,6-dihydroimidazo[2,1-b]thiazol-2-yl]ethanol
2-[3-(7-methylbenzo[b]thiophen-4-yl)-5,6-dihydroimidazo[2,1-b]thiazol-2-yl]ethanol
2-methyl-3-[6-(methylthio)benzo[b]thiophen-4-yl]-5,6-dihydroimidazo[2,1-b]thiazole
2-ethyl-3-[6-(methylthio)benzo[b]thiophen-4-yl]-5,6-dihydroimidazo[2,1-b]thiazole
3-[6-(methylthio)benzo[b]thiophen-4-yl]-2-propyl-5,6-dihydroimidazo[2,1-b]thiazole
2-(1-methylethyl)-3-[6-(methylthio)benzo[b]thiophen-4-yl]-5,6-dihydroimidazo[2,1-b]thiazole
2-cyclopropyl-3-[6-(methylthio)benzo[b]thiophen-4-yl]-5,6-dihydroimidazo[2,1-b]thiazole
3-[6-(methylthio)benzo[b]thiophen-4-yl]-2-vinyl-5,6-dihydroimidazo[2,1-b]thiazole
2-(methylthio)-3-[6-(methylthio)benzo[b]thiophen-4-yl]-5,6-dihydroimidazo[2,1-b]thiazole
[3-[6-(methylthio)benzo[b]thiophen-4-yl]-5,6-dihydroimidazo[2,1-b]thiazol-2-yl]methanol
1-[3-[6-(methylthio)benzo[b]thiophen-4-yl]-5,6-dihydroimidazo[2,1-b]thiazol-2-yl]ethanol
2-[3-[6-(methylthio)benzo[b]thiophen-4-yl]-5,6-dihydroimidazo[2,1-b]thiazol-2-yl]ethanol
2-methyl-3-[7-(methylthio)benzo[b]thiophen-4-yl]-5,6-dihydroimidazo[2,1-b]thiazole
2-ethyl-3-[7-(methylthio)benzo[b]thiophen-4-yl]-5,6-dihydroimidazo[2,1-b]thiazole
3-[7-(methylthio)benzo[b]thiophen-4-yl]-2-propyl-5,6-dihydroimidazo[2,1-b]thiazole
2-(1-methylethyl)-3-[7-(methylthio)benzo[b]thiophen-4-yl]-5,6-dihydroimidazo[2,1-b]thiazole
2-cyclopropyl-3-[7-(methylthio)benzo[b]thiophen-4-yl]-5,6-dihydroimidazo[2,1-b]thiazole
3-[7-(methylthio)benzo[b]thiophen-4-yl]-2-vinyl-5,6-dihydroimidazo[2,1-b]thiazole
2-(methylthio)-3-[7-(methylthio)benzo[b]thiophen-4-yl]-5,6-dihydroimidazo[2,1-b]thiazole
[3-[7-(methylthio)benzo[b]thiophen-4-yl]-5,6-dihydroimidazo[2,1-b]thiazol-2-yl]methanol
1-[3-[7-(methylthio)benzo[b]thiophen-4-yl]-5,6-dihydroimidazo[2,1-b]thiazol-2-yl]ethanol
2-[3-[7-(methylthio)benzo[b]thiophen-4-yl]-5,6-dihydroimidazo[2,1-b]thiazol-2-yl]ethanol
3-(benzo[b]thiophen-5-yl)-2-propyl-5,6-dihydroimidazo[2,1-b]thiazole 3-(benzo[b]thiophen-5-yl)-2-cyclopropyl-5,6-dihydroimidazo[2,1-b]thiazole
3-(benzo[b]thiophen-5-yl)-2-vinyl-5,6-dihydroimidazo[2,1-b]thiazole
1-[3-(benzo[b]thiophen-5-yl)-5,6-dihydroimidazo[2,1-b]thiazol-2-yl]ethanol
2-[3-(benzo[b]thiophen-5-yl)-5,6-dihydroimidazo[2,1-b]thiazol-2-yl]ethanol
3-(7-chlorobenzo[b]thiophen-5-yl)-2-methyl-5,6-dihydroimidazo[2,1-b]thiazole
3-(7-chlorobenzo[b]thiophen-5-yl)-2-ethyl-5,6-dihydroimidazo[2,1-b]thiazole
3-(7-chlorobenzo[b]thiophen-5-yl)-2-propyl-5,6-dihydroimidazo[2,1-b]thiazole
3-(7-chlorobenzo[b]thiophen-5-yl)-2-(1-methylethyl)-5,6-dihydroimidazo[2,1-b]thiazole
3-(7-chlorobenzo[b]thiophen-5-yl)-2-cyclopropyl-5,6-dihydroimidazo[2,1-b]thiazole
3-(7-chlorobenzo[b]thiophen-5-yl)-2-vinyl-5,6-dihydroimidazo[2,1-b]thiazole
3-(7-chlorobenzo[b]thiophen-5-yl)-2-(methylthio)-5,6-dihydroimidazo[2,1-b]thiazole
[3-(7-chlorobenzo[b]thiophen-5-yl)-5,6-dihydroimidazo[2,1-b]thiazol-2-yl]methanol
1-[3-(7-chlorobenzo[b]thiophen-5-yl)-5,6-dihydroimidazo[2,1-b]thiazol-2-yl]ethanol
2-[3-(7-chlorobenzo[b]thiophen-5-yl)-5,6-dihydroimidazo[2,1-b]thiazol-2-yl]ethanol
3-(7-fluorobenzo[b]thiophen-5-yl)-2-methyl-5,6-dihydroimidazo[2,1-b]thiazole
3-(7-fluorobenzo[b]thiophen-5-yl)-2-ethyl-5,6-dihydroimidazo[2,1-b]thiazole
3-(7-fluorobenzo[b]thiophen-5-yl)-2-propyl-5,6-dihydroimidazo[2,1-b]thiazole
3-(7-fluorobenzo[b]thiophen-5-yl)-2-(1-methylethyl)-5,6-dihydroimidazo[2,1-b]thiazole
3-(7-fluorobenzo[b]thiophen-5-yl)-2-cyclopropyl-5,6-dihydroimidazo[2,1-b]thiazole
3-(7-fluorobenzo[b]thiophen-5-yl)-2-vinyl-5,6-dihydroimidazo[2,1-b]thiazole
3-(7-fluorobenzo[b]thiophen-5-yl)-2-(methylthio)-5,6-dihydroimidazo[2,1-b]thiazole
[3-(7-fluorobenzo[b]thiophen-5-yl)-5,6-dihydroimidazo[2,1-b]thiazol-2-yl]methanol
1-[3-(7-fluorobenzo[b]thiophen-5-yl)-5,6-dihydroimidazo[2,1-b]thiazol-2-yl]ethanol
2-[3-(7-fluorobenzo[b]thiophen-5-yl)-5,6-dihydroimidazo[2,1-b]thiazol-2-yl]ethanol
3-(7-methoxybenzo[b]thiophen-5-yl)-2-methyl-5,6-dihydroimidazo[2,1-b]thiazole
2-ethyl-3-(7-methoxybenzo[b]thiophen-5-yl)-5,6-dihydroimidazo[2,1-b]thiazole
3-(7-methoxybenzo[b]thiophen-5-yl)-2-propyl-5,6-dihydroimidazo[2,1-b]thiazole
3-(7-methoxybenzo[b]thiophen-5-yl)-2-(1-methylethyl)-5,6-dihydroimidazo[2,1-b]thiazole
2-cyclopropyl-3-(7-methoxybenzo[b]thiophen-5-yl)-5,6-dihydroimidazo[2,1-b]thiazole
3-(7-methoxybenzo[b]thiophen-5-yl)-2-vinyl-5,6-dihydroimidazo[2,1-b]thiazole
3-(7-methoxybenzo[b]thiophen-5-yl)-2-(methylthio)-5,6-dihydroimidazo[2,1-b]thiazole
[3-(7-methoxybenzo[b]thiophen-5-yl)-5,6-dihydroimidazo[2,1-b]thiazol-2-yl]methanol
1-[3-(7-methoxybenzo[b]thiophen-5-yl)-5,6-dihydroimidazo[2,1-b]thiazol-2-yl]ethanol
2-[3-(7-methoxybenzo[b]thiophen-5-yl)-5,6-dihydroimidazo[2,1-b]thiazol-2-yl]ethanol
2-methyl-3-(2-methylbenzo[b]thiophen-5-yl)-5,6-dihydroimidazo[2,1-b]thiazole
2-ethyl-3-(2-methylbenzo[b]thiophen-5-yl)-5,6-dihydroimidazo[2,1-b]thiazole
3-(2-methylbenzo[b]thiophen-5-yl)-2-propyl-5,6-dihydroimidazo[2,1-b]thiazole
3-(2-methylbenzo[b]thiophen-5-yl)-2-(1-methylethyl)-5,6-dihydroimidazo[2,1-b]thiazole
2-cyclopropyl-3-(2-methylbenzo[b]thiophen-5-yl)-5,6-dihydroimidazo[2,1-b]thiazole
3-(2-methylbenzo[b]thiophen-5-yl)-2-vinyl-5,6-dihydroimidazo[2,1-b]thiazole
3-(2-methylbenzo[b]thiophen-5-yl)-2-(methylthio)-5,6-dihydroimidazo[2,1-b]thiazole
[3-(2-methylbenzo[b]thiophen-5-yl)-5,6-dihydroimidazo[2,1-b]thiazol-2-yl]methanol
1-[3-(2-methylbenzo[b]thiophen-5-yl)-5,6-dihydroimidazo[2,1-b]thiazol-2-yl]ethanol
2-[3-(2-methylbenzo[b]thiophen-5-yl)-5,6-dihydroimidazo[2,1-b]thiazol-2-yl]ethanol
2-methyl-3-(3-methylbenzo[b]thiophen-5-yl)-5,6-dihydroimidazo[2,1-b]thiazole
2-ethyl-3-(3-methylbenzo[b]thiophen-5-yl)-5,6-dihydroimidazo[2,1-b]thiazole
3-(3-methylbenzo[b]thiophen-5-yl)-2-propyl-5,6-dihydroimidazo[2,1-b]thiazole
3-(3-methylbenzo[b]thiophen-5-yl)-2-(1-methylethyl)-5,6-dihydroimidazo[2,1-b]thiazole
2-cyclopropyl-3-(3-methylbenzo[b]thiophen-5-yl)-5,6-dihydroimidazo[2,1-b]thiazole
3-(3-methylbenzo[b]thiophen-5-yl)-2-vinyl-5,6-dihydroimidazo[2,1-b]thiazole
3-(3-methylbenzo[b]thiophen-5-yl)-2-(methylthio)-5,6-dihydroimidazo[2,1-b]thiazole
[3-(3-methylbenzo[b]thiophen-5-yl)-5,6-dihydroimidazo[2,1-b]thiazol-2-yl]methanol
1-[3-(3-methylbenzo[b]thiophen-5-yl)-5,6-dihydroimidazo[2,1-b]thiazol-2-yl]ethanol
2-[3-(3-methylbenzo[b]thiophen-5-yl)-5,6-dihydroimidazo[2,1-b]thiazol-2-yl]ethanol
2-methyl-3-(7-methylbenzo[b]thiophen-5-yl)-5,6-dihydroimidazo[2,1-b]thiazole
2-ethyl-3-(7-methylbenzo[b]thiophen-5-yl)-5,6-dihydroimidazo[2,1-b]thiazole
3-(7-methylbenzo[b]thiophen-5-yl)-2-propyl-5,6-dihydroimidazo[2,1-b]thiazole
3-(7-methylbenzo[b]thiophen-5-yl)-2-(1-methylethyl)-5,6-dihydroimidazo[2,1-b]thiazole
2-cyclopropyl-3-(7-methylbenzo[b]thiophen-5-yl)-5,6-dihydroimidazo[2,1-b]thiazole
3-(7-methylbenzo[b]thiophen-5-yl)-2-vinyl-5,6-dihydroimidazo[2,1-b]thiazole
3-(7-methylbenzo[b]thiophen-5-yl)-2-(methylthio)-5,6-dihydroimidazo[2,1-b]thiazole
[3-(7-methylbenzo[b]thiophen-5-yl)-5,6-dihydroimidazo[2,1-b]thiazol-2-yl]methanol
1-[3-(7-methylbenzo[b]thiophen-5-yl)-5,6-dihydroimidazo[2,1-b]thiazol-2-yl]ethanol
2-[3-(7-methylbenzo[b]thiophen-5-yl)-5,6-dihydroimidazo[2,1-b]thiazol-2-yl]ethanol
2-methyl-3-[7-(methylthio)benzo[b]thiophen-5-yl]-5,6-dihydroimidazo[2,1-b]thiazole
2-ethyl-3-[7-(methylthio)benzo[b]thiophen-5-yl]-5,6-dihydroimidazo[2,1-b]thiazole
3-[7-(methylthio)benzo[b]thiophen-5-yl]-2-propyl-5,6-dihydroimidazo[2,1-b]thiazole
2-(1-methylethyl)-3-[7-(methylthio)benzo[b]thiophen-5-yl]-5,6-dihydroimidazo[2,1-b]thiazole 2-cyclopropyl-3-[7-(methylthio)benzo[b]thiophen-5-yl]-5,6-dihydroimidazo[2,1-b]thiazole
3-[7-(methylthio)benzo[b]thiophen-5-yl]-2-vinyl-5,6-dihydroimidazo[2,1-b]thiazole
2-(methylthio)-3-[7-(methylthio)benzo[b]thiophen-5-yl]-5,6-dihydroimidazo[2,1-b]thiazole
[3-[7-(methylthio)benzo[b]thiophen-5-yl]-5,6-dihydroimidazo[2,1-b]thiazol-2-yl]methanol
1-[3-[7-(methylthio)benzo[b]thiophen-5-yl]-5,6-dihydroimidazo[2,1-b]thiazol-2-yl]ethanol
2-[3-[7-(methylthio)benzo[b]thiophen-5-yl]-5,6-dihydroimidazo[2,1-b]thiazol-2-yl]ethanol
3-(benzo[b]thiophen-6-yl)-2-ethyl-5,6-dihydroimidazo[2,1-b]thiazole
3-(benzo[b]thiophen-6-yl)-2-propyl-5,6-dihydroimidazo[2,1-b]thiazole
3-(benzo[b]thiophen-6-yl)-2-(1-methylethyl)-5,6-dihydroimidazo[2,1-b]thiazole
3-(benzo[b]thiophen-6-yl)-2-cyclopropyl-5,6-dihydroimidazo[2,1-b]thiazole
3-(benzo[b]thiophen-6-yl)-2-vinyl-5,6-dihydroimidazo[2,1-b]thiazole
3-(benzo[b]thiophen-6-yl)-2-(methylthio)-5,6-dihydroimidazo[2,1-b]thiazole
[3-(benzo[b]thiophen-6-yl)-5,6-dihydroimidazo[2,1-b]thiazol-2-yl]methanol
1-[3-(benzo[b]thiophen-6-yl)-5,6-dihydroimidazo[2,1-b]thiazol-2-yl]ethanol
2-[3-(benzo[b]thiophen-6-yl)-5,6-dihydroimidazo[2,1-b]thiazol-2-yl]ethanol
3-(4-chlorobenzo[b]thiophen-6-yl)-2-methyl-5,6-dihydroimidazo[2,1-b]thiazole
3-(4-chlorobenzo[b]thiophen-6-yl)-2-ethyl-5,6-dihydroimidazo[2,1-b]thiazole
3-(4-chlorobenzo[b]thiophen-6-yl)-2-propyl-5,6-dihydroimidazo[2,1-b]thiazole
3-(4-chlorobenzo[b]thiophen-6-yl)-2-(1-methylethyl)-5,6-dihydroimidazo[2,1-b]thiazole
3-(4-chlorobenzo[b]thiophen-6-yl)-2-cyclopropyl-5,6-dihydroimidazo[2,1-b]thiazole
3-(4-chlorobenzo[b]thiophen-6-yl)-2-vinyl-5,6-dihydroimidazo[2,1-b]thiazole
3-(4-chlorobenzo[b]thiophen-6-yl)-2-(methylthio)-5,6-dihydroimidazo[2,1-b]thiazole
[3-(4-chlorobenzo[b]thiophen-6-yl)-5,6-dihydroimidazo[2,1-b]thiazol-2-yl]methanol
1-[3-(4-chlorobenzo[b]thiophen-6-yl)-5,6-dihydroimidazo[2,1-b]thiazol-2-yl]ethanol
2-[3-(4-chlorobenzo[b]thiophen-6-yl)-5,6-dihydroimidazo[2,1-b]thiazol-2-yl]ethanol
3-(4-fluorobenzo[b]thiophen-6-yl)-2-methyl-5,6-dihydroimidazo[2,1-b]thiazole
3-(4-fluorobenzo[b]thiophen-6-yl)-2-ethyl-5,6-dihydroimidazo[2,1-b]thiazole
3-(4-fluorobenzo[b]thiophen-6-yl)-2-propyl-5,6-dihydroimidazo[2,1-b]thiazole
3-(4-fluorobenzo[b]thiophen-6-yl)-2-(1-methylethyl)-5,6-dihydroimidazo[2,1-b]thiazole
3-(4-fluorobenzo[b]thiophen-6-yl)-2-cyclopropyl-5,6-dihydroimidazo[2,1-b]thiazole
3-(4-fluorobenzo[b]thiophen-6-yl)-2-vinyl-5,6-dihydroimidazo[2,1-b]thiazole
3-(4-fluorobenzo[b]thiophen-6-yl)-2-(methyhio)-5,6-dihydroimidazo[2,1-b]thiazole
[3-(4-fluorobenzo[b]thiophen-6-yl)-5,6-dihydroimidazo[2,1-b]thiazol-2-yl]methanol
1-[3-(4-fluorobenzo[b]thiophen-6-yl)-5,6-dihydroimidazo[2,1-b]thiazol-2-yl]ethanol
2-[3-(4-fluorobenzo[b]thiophen-6-yl)-5,6-dihydroimidazo[2,1-b]thiazol-2-yl]ethanol
3-(4-methoxybenzo[b]thiophen-6-yl)-2-methyl-5,6-dihydroimidazo[2,1-b]thiazole
2-ethyl-3-(4-methoxybenzo[b]thiophen-6-yl)-5,6-dihydroimidazo[2,1-b]thiazole
3-(4-methoxybenzo[b]thiophen-6-yl)-2-propyl-5,6-dihydroimidazo[2,1-b]thiazole
3-(4-methoxybenzo[b]thiophen-6-yl)-2-(1-methylethyl)-5,6-dihydroimidazo[2,1-b]thiazole
2-cyclopropyl-3-(4-methoxybenzo[b]thiophen-6-yl)-5,6-dihydroimidazo[2,1-b]thiazole
3-(4-methoxybenzo[b]thiophen-6-yl)-2-vinyl-5,6-dihydroimidazo[2,1-b]thiazole
3-(4-methoxybenzo[b]thiophen-6-yl)-2-(methylthio)-5,6-dihydroimidazo[2,1-b]thiazole
[3-(4-methoxybenzo[b]thiophen-6-yl)-5,6-dihydroimidazo[2,1-b]thiazol-2-yl]methanol
1-[3-(4-methoxybenzo[b]thiophen-6-yl)-5,6-dihydroimidazo[2,1-b]thiazol-2-yl]ethanol
2-[3-(4-methoxybenzo[b]thiophen-6-yl)-5,6-dihydroimidazo[2,1-b]thiazol-2-yl]ethanol
2-methyl-3-(2-methylbenzo[b]thiophen-6-yl)-5,6-dihydroimidazo[2,1-b]thiazole
2-ethyl-3-(2-methylbenzo[b]thiophen-6-yl)-5,6-dihydroimidazo[2,1-b]thiazole
3-(2-methylbenzo[b]thiophen-6-yl)-2-propyl-5,6-dihydroimidazo[2,1-b]thiazole
3-(2-methylbenzo[b]thiophen-6-yl)-2-(1-methylethyl)-5,6-dihydroimidazo[2,1-b]thiazole
2-cyclopropyl-3-(2-methylbenzo[b]thiophen-6-yl)-5,6-dihydroimidazo[2,1-b]thiazole
3-(2-methylbenzo[b]thiophen-6-yl)-2-vinyl-5,6-dihydroimidazo[2,1-b]thiazole
3-(2-methylbenzo[b]thiophen-6-yl)-2-(methylthio)-5,6-dihydroimidazo[2,1-b]thiazole
[3-(2-methylbenzo[b]thiophen-6-yl)-5,6-dihydroimidazo[2,1-b]thiazol-2-yl]methanol
1-[3-(2-methylbenzo[b]thiophen-6-yl)-5,6-dihydroimidazo[2,1-b]thiazol-2-yl]ethanol
2-[3-(2-methylbenzo[b]thiophen-6-yl)-5,6-dihydroimidazo[2,1-b]thiazol-2-yl]ethanol
2-methyl-3-(3-methylbenzo[b]thiophen-6-yl)-5,6-dihydroimidazo[2,1-b]thiazole
2-ethyl-3-(3-methylbenzo[b]thiophen-6-yl)-5,6-dihydroimidazo[2,1-b]thiazole
3-(3-methylbenzo[b]thiophen-6-yl)-2-propyl-5,6-dihydroimidazo[2,1-b]thiazole
3-(3-methylbenzo[b]thiophen-6-yl)-2-(1-methylethyl)-5,6-dihydroimidazo[2,1-b]thiazole
2-cyclopropyl-3-(3-methylbenzo[b]thiophen-6-yl)-5,6-dihydroimidazo[2,1-b]thiazole
3-(3-methylbenzo[b]thiophen-6-yl)-2-vinyl-5,6-dihydroimidazo[2,1-b]thiazole
3-(3-methylbenzo[b]thiophen-6-yl)-2-(methylthio)-5,6-dihydroimidazo[2,1-b]thiazole
[3-(3-methylbenzo[b]thiophen-6-yl)-5,6-dihydroimidazo[2,1-b]thiazol-2-yl]methanol
1-[3-(3-methylbenzo[b]thiophen-6-yl)-5,6-dihydroimidazo[2,1-b]thiazol-2-yl]ethanol
2-[3-(3-methylbenzo[b]thiophen-6-yl)-5,6-dihydroimidazo[2,1-b]thiazol-2-yl]ethanol
2-methyl-3-(4-methylbenzo[b]thiophen-6-yl)-5,6-dihydroimidazo[2,1-b]thiazole
2-ethyl-3-(4-methylbenzo[b]thiophen-6-yl)-5,6-dihydroimidazo[2,1-b]thiazole
3-(4-methylbenzo[b]thiophen-6-yl)-2-propyl-5,6-dihydroimidazo[2,1-b]thiazole 3-(4-methylbenzo[b]thiophen-6-yl)-2-(1-methylethyl)-5,6-dihydroimidazo[2,1-b]thiazole
2-cyclopropyl-3-(4-methylbenzo[b]thiophen-6-yl)-5,6-dihydroimidazo[2,1-b]thiazole
3-(4-methylbenzo[b]thiophen-6-yl)-2-vinyl-5,6-dihydroimidazo[2,1-b]thiazole
3-(4-methylbenzo[b]thiophen-6-yl)-2-(methylthio)-5,6-dihydroimidazo[2,1-b]thiazole
[3-(4-methylbenzo[b]thiophen-6-yl)-5,6-dihydroimidazo[2,1-b]thiazol-2-yl]methanol
1-[3-(4-methylbenzo[b]thiophen-6-yl)-5,6-dihydroimidazo[2,1-b]thiazol-2-yl]ethanol
2-[3-(4-methylbenzo[b]thiophen-6-yl)-5,6-dihydroimidazo[2,1-b]thiazol-2-yl]ethanol
2-methyl-3-[4-(methylthio)benzo[b]thiophen-6-yl]-5,6-dihydroimidazo[2,1-b]thiazole
2-ethyl-3-[4-(methylthio)benzo[b]thiophen-6-yl]-5,6-dihydroimidazo[2,1-b]thiazole
3-[4-(methylthio)benzo[b]thiophen-6-yl]-2-propyl-5,6-dihydroimidazo[2,1-b]thiazole
2-(1-methylethyl)-3-[4-(methylthio)benzo[b]thiophen-6-yl]-5,6-dihydroimidazo[2,1-b]thiazole
2-cyclopropyl-3-[4-(methylthio)benzo[b]thiophen-6-yl]-5,6-dihydroimidazo[2,1-b]thiazole
3-[4-(methylthio)benzo[b]thiophen-6-yl]-2-vinyl-5,6-dihydroimidazo[2,1-b]thiazole
2-(methylthio)-3-[4-(methylthio)benzo[b]thiophen-6-yl]-5,6-dihydroimidazo[2,1-b]thiazole
[3-[4-(methylthio)benzo[b]thiophen-6-yl]-5,6-dihydroimidazo[2,1-b]thiazol-2-yl]methanol
1-[3-[4-(methylthio)benzo[b]thiophen-6-yl]-5,6-dihydroimidazo[2,1-b]thiazol-2-yl]ethanol
2-[3-[4-(methylthio)benzo[b]thiophen-6-yl]-5,6-dihydroimidazo[2,1-b]thiazol-2-yl]ethanol
3-(benzo[b]thiophen-7-yl)-2-ethyl-5,6-dihydroimidazo[2,1-b]thiazole
3-(benzo[b]thiophen-7-yl)-2-propyl-5,6-dihydroimidazo[2,1-b]thiazole
3-(benzo[b]thiophen-7-yl)-2-(1-methylethyl)-5,6-dihydroimidazo[2,1-b]thiazole
3-(benzo[b]thiophen-7-yl)-2-cyclopropyl-5,6-dihydroimidazo[2,1-b]thiazole
3-(benzo[b]thiophen-7-yl)-2-vinyl-5,6-dihydroimidazo[2,1-b]thiazole
3-(benzo[b]thiophen-7-yl)-2-(methylthio)-5,6-dihydroimidazo[2,1-b]thiazole
[3-(benzo[b]thiophen-7-yl)-5,6-dihydroimidazo[2,1-b]thiazol-2-yl]methanol
1-[3-(benzo[b]thiophen-7-yl)-5,6-dihydroimidazo[2,1-b]thiazol-2-yl]ethanol
2-[3-(benzo[b]thiophen-7-yl)-5,6-dihydroimidazo[2,1-b]thiazol-2-yl]ethanol
3-(4-chlorobenzo[b]thiophen-7-yl)-2-methyl-5,6-dihydroimidazo[2,1-b]thiazole
3-(4-chlorobenzo[b]thiophen-7-yl)-2-ethyl-5,6-dihydroimidazo[2,1-b]thiazole
3-(4-chlorobenzo[b]thiophen-7-yl)-2-propyl-5,6-dihydroimidazo[2,1-b]thiazole
3-(4-chlorobenzo[b]thiophen-7-yl)-2-(1-methylethyl)-5,6-dihydroimidazo[2,1-b]thiazole
3-(4-chlorobenzo[b]thiophen-7-yl)-2-cyclopropyl-5,6-dihydroimidazo[2,1-b]thiazole
3-(4-chlorobenzo[b]thiophen-7-yl)-2-vinyl-5,6-dihydroimidazo[2,1-b]thiazole
3-(4-chlorobenzo[b]thiophen-7-yl)-2-(methylthio)-5,6-dihydroimidazo[2,1-b]thiazole
[3-(4-chlorobenzo[b]thiophen-7-yl)-5,6-dihydroimidazo[2,1-b]thiazol-2-yl]methanol
1-[3-(4-chlorobenzo[b]thiophen-7-yl)-5,6-dihydroimidazo[2,1-b]thiazol-2-yl]ethanol
2-[3-(4-chlorobenzo[b]thiophen-7-yl)-5,6-dihydroimidazo[2,1-b]thiazol-2-yl]ethanol
3-(5-chlorobenzo[b]thiophen-7-yl)-2-methyl-5,6-dihydroimidazo[2,1-b]thiazole
3-(5-chlorobenzo[b]thiophen-7-yl)-2-ethyl-5,6-dihydroimidazo[2,1-b]thiazole
3-(5-chlorobenzo[b]thiophen-7-yl)-2-propyl-5,6-dihydroimidazo[2,1-b]thiazole
3-(5-chlorobenzo[b]thiophen-7-yl)-2-(1-methylethyl)-5,6-dihydroimidazo[2,1-b]thiazole
3-(5-chlorobenzo[b]thiophen-7-yl)-2-cyclopropyl-5,6-dihydroimidazo[2,1-b]thiazole
3-(5-chlorobenzo[b]thiophen-7-yl)-2-vinyl-5,6-dihydroimidazo[2,1-b]thiazole
3-(5-chlorobenzo[b]thiophen-7-yl)-2-(methylthio)-516-dihydroimidazo[2,1-b]thiazole
[3-(5-chlorobenzo[b]thiophen-7-yl)-5,6-dihydroimidazo[2,1-b]thiazol-2-yl]methanol
1-[3-(5-chlorobenzo[b]thiophen-7-yl)-5,6-dihydroimidazo[2,1-b]thiazol-2-yl]ethanol
2-[3-(5-chlorobenzo[b]thiophen-7-yl)-5,6-dihydroimidazo[2,1-b]thiazol-2-yl]ethanol
3-(4-fluorobenzo[b]thiophen-7-yl)-2-methyl-5,6-dihydroimidazo[2,1-b]thiazole
3-(4-fluorobenzo[b]thiophen-7-yl)-2-ethyl-5,6-dihydroimidazo[2,1-b]thiazole
3-(4-fluorobenzo[b]thiophen-7-yl)-2-propyl-5,6-dihydroimidazo[2,1-b]thiazole
3-(4-fluorobenzo[b]thiophen-7-yl)-2-(1-methylethyl)-5,6-dihydroimidazo[2,1-b]thiazole
3-(4-fluorobenzo[b]thiophen-7-yl)-2-cyclopropyl-5,6-dihydroimidazo[2,1-b]thiazole
3-(4-fluorobenzo[b]thiophen-7-yl)-2-vinyl-5,6-dihydroimidazo[2,1-b]thiazole
3-(4-fluorobenzo[b]thiophen-7-yl)-2-(methylthio)-5,6-dihydroimidazo[2,1-b]thiazole
[3-(4-fluorobenzo[b]thiophen-7-yl)-5,6-dihydroimidazo[2,1-b]thiazol-2-yl]methanol
1-[3-(4-fluorobenzo[b]thiophen-7-yl)-5,6-dihydroimidazo[2,1-b]thiazol-2-yl]ethanol
2-[3-(4-fluorobenzo[b]thiophen-7-yl)-5,6-dihydroimidazo[2,1-b]thiazol-2-yl]ethanol
3-(5-fluorobenzo[b]thiophen-7-yl)-2-methyl-5,6-dihydroimidazo[2,1-b]thiazole
3-(5-fluorobenzo[b]thiophen-7-yl)-2-ethyl-5,6-dihydroimidazo[2,1-b]thiazole
3-(5-fluorobenzo[b]thiophen-7-yl)-2-propyl-5,6-dihydroimidazo[2,1-b]thiazole
3-(5-fluorobenzo[b]thiophen-7-yl)-2-(1-methylethyl)-5,6-dihydroimidazo[2,1-b]thiazole
3-(5-fluorobenzo[b]thiophen-7-yl)-2-cyclopropyl-5,6-dihydroimidazo[2,1-b]thiazole
3-(5-fluorobenzo[b]thiophen-7-yl)-2-vinyl-5,6-dihydroimidazo[2,1-b]thiazole
3-(5-fluorobenzo[b]thiophen-7-yl)-2-(methylthio)-5,6-dihydroimidazo[2,1-b]thiazole
[3-(5-fluorobenzo[b]thiophen-7-yl)-5,6-dihydroimidazo[2,1-b]thiazol-2-yl]methanol
1-[3-(5-fluorobenzo[b]thiophen-7-yl)-5,6-dihydroimidazo[2,1-b]thiazol-2-yl]ethanol
2-[3-(5-fluorobenzo[b]thiophen-7-yl)-5,6-dihydroimidazo[2,1-b]thiazol-2-yl]ethanol
3-(5-methoxybenzo[b]thiophen-7-yl)-2-methyl-5,6-dihydroimidazo[2,1-b]thiazole
2-ethyl-3-(5-methoxybenzo[b]thiophen-7-yl)-5,6-dihydroimidazo[2,1-b]thiazole 3-(5-methoxybenzo[b]thiophen-7-yl)-2-propyl-5,6-dihydroimidazo[2,1-b]thiazole
3-(5-methoxybenzo[b]thiophen-7-yl)-2-(1-methylethyl)-5,6-dihydroimidazo[2,1-b]thiazole
2-cyclopropyl-3-(5-methoxybenzo[b]thiophen-7-yl)-5,6-dihydroimidazo[2,1-b]thiazole
3-(5-methoxybenzo[b]thiophen-7-yl)-2-vinyl-5,6-dihydroimidazo[2,1-b]thiazole
3-(5-methoxybenzo[b]thiophen-7-yl)-2-(methylthio)-5,6-dihydroimidazo[2,1-b]thiazole
[3-(5-methoxybenzo[b]thiophen-7-yl)-5,6-dihydroimidazo[2,1-b]thiazol-2-yl]methanol
1-[3-(5-methoxybenzo[b]thiophen-7-yl)-5,6-dihydroimidazo[2,1-b]thiazol-2-yl]ethanol
2-[3-(5-methoxybenzo[b]thiophen-7-yl)-5,6-dihydroimidazo[2,1-b]thiazol-2-yl]ethanol
2-methyl-3-(2-methylbenzo[b]thiophen-7-yl)-5,6-dihydroimidazo[2,1-b]thiazole
2-ethyl-3-(2-methylbenzo[b]thiophen-7-yl)-5,6-dihydroimidazo[2,1-b]thiazole
3-(2-methylbenzo[b]thiophen-7-yl)-2-propyl-5,6-dihydroimidazo[2,1-b]thiazole
3-(2-methylbenzo[b]thiophen-7-yl)-2-(1-methylethyl)-5,6-dihydroimidazo[2,1-b]thiazole
2-cyclopropyl-3-(2-methylbenzo[b]thiophen-7-yl)-5,6-dihydroimidazo[2,1-b]thiazole
3-(2-methylbenzo[b]thiophen-7-yl)-2-vinyl-5,6-dihydroimidazo[2,1-b]thiazole
3-(2-methylbenzo[b]thiophen-7-yl)-2-(methylthio)-5,6-dihydroimidazo[2,1-b]thiazole
[3-(2-methylbenzo[b]thiophen-7-yl)-5,6-dihydroimidazo[2,1-b]thiazol-2-yl]methanol
1-[3-(2-methylbenzo[b]thiophen-7-yl)-5,6-dihydroimidazo[2,1-b]thiazol-2-yl]ethanol
2-[3-(2-methylbenzo[b]thiophen-7-yl)-5,6-dihydroimidazo[2,1-b]thiazol-2-yl]ethanol
2-methyl-3-(3-methylbenzo[b]thiophen-7-yl)-5,6-dihydroimidazo[2,1-b]thiazole
2-ethyl-3-(3-methylbenzo[b]thiophen-7-yl)-5,6-dihydroimidazo[2,1-b]thiazole
3-(3-methylbenzo[b]thiophen-7-yl)-2-propyl-5,6-dihydroimidazo[2,1-b]thiazole
3-(3-methylbenzo[b]thiophen-7-yl)-2-(1-methylethyl)-5,6-dihydroimidazo[2,1-b]thiazole
2-cyclopropyl-3-(3-methylbenzo[b]thiophen-7-yl)-5,6-dihydroimidazo[2,1-b]thiazole
3-(3-methylbenzo[b]thiophen-7-yl)-2-vinyl-5,6-dihydroimidazo[2,1-b]thiazole
3-(3-methylbenzo[b]thiophen-7-yl)-2-(methylthio)-5,6-dihydroimidazo[2,1-b]thiazole
[3-(3-methylbenzo[b]thiophen-7-yl)-5,6-dihydroimidazo[2,1-b]thiazol-2-yl]methanol
1-[3-(3-methylbenzo[b]thiophen-7-yl)-5,6-dihydroimidazo[2,1-b]thiazol-2-yl]ethanol
2-[3-(3-methylbenzo[b]thiophen-7-yl)-5,6-dihydroimidazo[2,1-b]thiazol-2-yl]ethanol
2-methyl-3-(4-methylbenzo[b]thiophen-7-yl)-5,6-dihydroimidazo[2,1-b]thiazole
2-ethyl-3-(4-methylbenzo[b]thiophen-7-yl)-5,6-dihydroimidazo[2,1-b]thiazole
3-(4-methylbenzo[b]thiophen-7-yl)-2-propyl-5,6-dihydroimidazo[2,1-b]thiazole
3-(4-methylbenzo[b]thiophen-7-yl)-2-(1-methylethyl)-5,6-dihydroimidazo[2,1-b]thiazole
2-cyclopropyl-3-(4-methylbenzo[b]thiophen-7-yl)-5,6-dihydroimidazo[2,1-b]thiazole
3-(4-methylbenzo[b]thiophen-7-yl)-2-vinyl-5,6-dihydroimidazo[2,1-b]thiazole
3-(4-methylbenzo[b]thiophen-7-yl)-2-(methylthio)-5,6-dihydroimidazo[2,1-b]thiazole
[3-(4-methylbenzo[b]thiophen-7-yl)-5,6-dihydroimidazo[2,1-b]thiazol-2-yl]methanol
1-[3-(4-methylbenzo[b]thiophen-7-yl)-5,6-dihydroimidazo[2,1-b]thiazol-2-yl]ethanol
2-[3-(4-methylbenzo[b]thiophen-7-yl)-5,6-dihydroimidazo[2,1-b]thiazol-2-yl]ethanol
2-methyl-3-(5-methylbenzo[b]thiophen-7-yl)-5,6-dihydroimidazo[2,1-b]thiazole
2-ethyl-3-(5-methylbenzo[b]thiophen-7-yl)-5,6-dihydroimidazo[2,1-b]thiazole
3-(5-methylbenzo[b]thiophen-7-yl)-2-propyl-5,6-dihydroimidazo[2,1-b]thiazole
3-(5-methylbenzo[b]thiophen-7-yl)-2-(1-methylethyl)-5,6-dihydroimidazo[2,1-b]thiazole
2-cyclopropyl-3-(5-methylbenzo[b]thiophen-7-yl)-5,6-dihydroimidazo[2,1-b]thiazole
3-(5-methylbenzo[b]thiophen-7-yl)-2-vinyl-5,6-dihydroimidazo[2,1-b]thiazole
3-(15-methylbenzo[b]thiophen-7-yl)-2-(methylthio)-5,6-dihydroimidazo[2,1-b]thiazole
[3-(5-methylbenzo[b]thiophen-7-yl)-5,6-dihydroimidazo[2,1-b]thiazol-2-yl]methanol
1-[3-(5-methylbenzo[b]thiophen-7-yl)-5,6-dihydroimidazo[2,1-b]thiazol-2-yl]ethanol
2-[3-(5-methylbenzo[b]thiophen-7-yl)-5,6-dihydroimidazo[2,1-b]thiazol-2-yl]ethanol
2-methyl-3-[4-(methylthio)benzo[b]thiophen-7-yl]-5,6-dihydroimidazo[2,1-b]thiazole
2-ethyl-3-[4-(methylthio)benzo[b]thiophen-7-yl]-5,6-dihydroimidazo[2,1-b]thiazole
3-[4-(methylthio)benzo[b]thiophen-7-yl]-2-propyl-5,6-dihydroimidazo[2,1-b]thiazole
2-(1-methylethyl)-3-[4-(methylthio)benzo[b]thiophen-7-yl]-5,6-dihydroimidazo[2,1-b]thiazole
2-cyclopropyl-3-[4-(methylthio)benzo[b]thiophen-7-yl]-5,6-dihydroimidazo[2,1-b]thiazole
3-[4-(methylthio)benzo[b]thiophen-7-yl]-2-vinyl-5,6-dihydroimidazo[2,1-b]thiazole
2-(methylthio)-3-[4-(methylthio)benzo[b]thiophen-7-yl]-5,6-dihydroimidazo[2,1-b]thiazole
[3-[4-(methylthio)benzo[b]thiophen-7-yl]-5,6-dihydroimidazo[2,1-b]thiazol-2-yl]methanol
1-[3-[4-(methylthio)benzo[b]thiophen-7-yl]-5,6-dihydroimidazo[2,1-b]thiazol-2-yl]ethanol
2-[3-[4-(methylthio)benzo[b]thiophen-7-yl]-5,6-dihydroimidazo[2,1-b]thiazol-2-yl]ethanol
2-methyl-3-[5-(methylthio)benzo[b]thiophen-7-yl]-5,6-dihydroimidazo[2,1-b]thiazole
2-ethyl-3-[5-(methylthio)benzo[b]thiophen-7-yl]-5,6-dihydroimidazo[2,1-b]thiazole
3-[5-(methylthio)benzo[b]thiophen-7-yl]-2-propyl-5,6-dihydroimidazo[2,1-b]thiazole
2-(1-methylethyl)-3-[5-(methylthio)benzo[b]thiophen-7-yl]-5,6-dihydroimidazo[2,1-b]thiazole
2-cyclopropyl-3-[5-(methylthio)benzo[b]thiophen-7-yl]-5,6-dihydroimidazo[2,1-b]thiazole
3-[5-(methylthio)benzo[b]thiophen-7-yl]-2-vinyl-5,6-dihydroimidazo[2,1-b]thiazole
2-(methylthio)-3-[5-(methylthio)benzo[b]thiophen-7-yl]-5,6-dihydroimidazo[2,1-b]thiazole
[3-[5-(methylthio)benzo[b]thiophen-7-yl]-5,6-dihydroimidazo[2,1-b]thiazol-2-yl]methanol
1-[3-[5-(methylthio)benzo[b]thiophen-7-yl]-5,6-dihydroimidazo[2,1-b]thiazol-2-yl]ethanol
2-[3-[5-(methylthio)benzo[b]thiophen-7-yl]-5,6-dihydroimidazo[2,1-b]thiazol-2-yl]ethanol including pharmaceutically acceptable salts thereof and individual enantiomers, racemates or other mixtures of enantiomers.

The present invention also includes pharmaceutical compositions comprising a therapeutically effective amount of a compound of Formula I or a salt thereof together with a pharmaceutically acceptable diluent or carrier.

As used hereinafter, the term "active compound" denotes a compound of Formula I or a salt thereof. In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1–99% by weight of active compound. The compositions of the invention are generally prepared in unit dosage form. Preferably the unit dosage of active ingredient is 1–500 mg. The excipients used in the preparation of these compositions are the excipients known in the pharmacist's art.

Compositions for oral administration are the preferred compositions of the invention and these are the known pharmaceutical forms for such administration, for example tablets, capsules, syrups and aqueous or oil suspensions. The excipients used in the preparation of these compositions are the excipients known in the pharmacist's art. Tablets may be prepared by mixing the active compound with an inert diluent such as calcium phosphate in the presence of disintegrating agents, for example maize starch, and lubricating agents, for example magnesium stearate, and tableting the mixture by known methods. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The tablets and capsules may conveniently each contain 1 to 500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

Preferably the compositions of the invention are administered orally in the known pharmaceutical forms for such administration. Dosage forms suitable for oral administration may comprise tablets, pills, capsules, caplets, multiparticulates including: granules, beads, pellets and microencapsulated particles; powders, elixirs, syrups, suspensions and solutions.

Solid oral dosage forms, for example tablets, may be prepared by mixing the pharmaceutical composition of the present invention with one or more of the following ingredients or mixtures thereof:

inert diluents, for example calcium carbonate, calcium sulphate, compressible sugar, confectioner's sugar, dextrates, dextrin, dextrose, dibasic calcium phosphate dihydrate, glyceryl palmitostearate, hydrogenated vegetable oil, kaolin, lactose, magnesium carbonate, magnesium oxide, maltodextrin, mannitol, microcrystalline cellulose, polymethacrylates, potassium chloride, powdered cellulose, pregelatinized starch, sodium chloride, sorbitol, starch, sucrose, sugar spheres, talc and tribasic calcium phosphate;

disintegrating agents, for example alginic acid, carboxymethylcellulose calcium, carboxymethylcellulose sodium, colloidal silicon dioxide, croscarmellose sodium, crospovidone, guar gum, magnesium aluminium silicate, methylcellulose, microcrystalline cellulose, polacrilin potassium, powdered cellulose, pregelatinized starch, sodium alginate, sodium starch glycolate, starch including maize starch and agar;

lubricating agents, for example calcium stearate, glyceryl monostearate, glyceryl palmitostearate, hydrogenated castor oil, hydrogenated vegetable oil, light mineral oil, magnesium stearate, mineral oil, polyethylene glycol, sodium benzoate, sodium lauryl sulphate, sodium stearyl fumarate, stearic acid, talc and zinc stearate;

binders, for example acacia, alginic acid, carbomer, carboxymethylcellulose sodium, dextrin, ethylcellulose, gelatin, guar gum, hydrogenated vegetable oil, hydroxyethyl cellulose, hydroxypropyl cellulose, hydroxypropyl methylcellulose, liquid glucose, magnesium aluminium silicate, maltodextrin, methylcellulose, polymethacrylates, povidone, pregelatinized starch, sodium alginate, starch including maize starch, zein, sugars (such as sucrose, molasses and lactose), and natural and synthetic gums (such as extract of Irish moss, polyethylene glycol, waxes, microcrystalline cellulose and polyvinylpyrrolidone);

colouring agents, for example conventional pharmaceutically acceptable dyes;

sweetening and flavouring agents;

preservatives;

one or more pharmaceutically acceptable couple or couples (such as those comprising an acid and a carbonate or bicarbonate salt), which effervesces to aid dissolution when the solid dosage form is added to water; and other optional ingredients known in the art to permit production of oral dosage forms by known methods such as tableting.

Solid oral dosage forms may be formulated in a manner known to those skilled in the art so as to give a sustained release of the active compound. Film coated, solid oral dosage forms comprising compositions of the present invention may be advantageous, depending on the nature of the active compound. Various materials, for example shellac and/or sugar, may be present as coatings, or to otherwise modify the physical form of the oral dosage form. For example tablets or pills may, if desired, be provided with enteric coatings by known methods, for example by the use of cellulose acetate phthalate and/or hydroxy propyl methylcellulose phthalate.

Capsules and/or caplets (for example hard or soft gelatin capsules) comprising the active compound (with or without added excipients such as a fatty oil), may be prepared by conventional means and, if desired, provided with enteric coatings in a known manner. The contents of the capsule and/or caplet may be formulated using known methods to give sustained release of the active compound.

Liquid oral dosage forms comprising compositions of the present invention may be an elixir, suspension and/or syrup (for example, aqueous suspensions containing the active compound in an aqueous medium in the presence of a non-toxic suspending agent [such as sodium carboxymethylcellulose] and/or oily suspensions containing the active compound in a suitable vegetable oil [such as arachis oil and/or sunflower oil]). Liquid oral dosage forms may also comprise one or more sweetening agent, flavouring agent, preservatives and/or mixtures thereof.

The active compound may be formulated into granules with or without additional excipients. The granules may be ingested directly by the patient or they may be added to a suitable liquid carrier (for example water) before ingestion. The granules may contain disintegrants (for example a pharmaceutically acceptable effervescent couple formed from an acid and a carbonate or bicarbonate salt) to facilitate dispersion in the liquid medium.

Preferably each of the above oral dosage forms may contain from about 1 mg to about 1000 mg, more preferably from about 5 mg to about 500 mg (for example 10 mg, 50 mg, 100 mg, 200 mg, or 400 mg) of the active compound.

Compositions of the invention suitable for rectal administration are the known pharmaceutical forms for such administration, for example, suppositories with hard fat, semi-synthetic glyceride, cocoa butter and/or polyethylene glycol bases.

Pharmaceutical compositions may also be administered parenterally (for example subcutaneously, intramuscularly, intradermally and/or intravenously [such as by injection and/or infusion] in the known pharmaceutical dosage forms for parenteral administration (for example sterile suspensions in aqueous and/or oily media and/or sterile solutions in suitable solvents, preferably isotonic with the blood of the intended patient). Parenteral dosage forms may be sterilised (for example by micro-filtration and/or using suitable sterilising agents [such as ethylene oxide]). Optionally one or more of the following pharmaceutically acceptable adjuvants suitable for parenteral administration may be added to parenteral dosage forms: local anaesthethetics, preservatives, buffering agents and/or mixtures thereof. Parenteral dosage forms may be stored in suitable sterile sealed containers (for example ampoules and/or vials) until use. To enhance stability during storage the parenteral dosage form may be frozen after filling the container and fluid (for example water) may be removed under reduced pressure.

Pharmaceutical compositions may be administered nasally in known pharmaceutical forms for such administration (for example sprays, aerosols, nebulised solutions and/or powders). Metered dose systems known to those skilled in the art (for example aerosols and/or inhalers) may be used.

Pharmaceutical compositions may be administered to the buccal cavity (for example sub-lingually) in known pharmaceutical forms for such administration (for example slow dissolving tablets, chewing gums, troches, lozenges, pastilles, gels, pastes, mouthwashes, rinses and/or powders).

Compositions for topical administration may comprise a matrix in which the pharmacologically active compounds of the present invention are dispersed so that the compounds are held in contact with the skin in order to administer the compounds transdermally. A suitable transdermal composition may be prepared by mixing the pharmaceutically active compound with a topical vehicle, such as a mineral oil, petrolatum and/or a wax, for example paraffin wax or beeswax, together with a potential transdermal accelerant such as dimethyl sulphoxide or propylene glycol. Alternatively the active compounds may be dispersed in a pharmaceutically acceptable cream or ointment base. The amount of active compound contained in a topical formulation should be such that a therapeutically effective amount of the compound is delivered during the period of time for which the topical formulation is intended to be on the skin.

The compounds of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as a suspension or solution in a pharmaceutically acceptable oil of the compound to be infused for example in the form of a very sparingly water-soluble derivative such as a dodecanoate salt or (b) solid in the form of an implanted support, for example of a synthetic resin or waxy material, for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The present invention also comprises a compound of Formula I for use as a medicament.

The pharmaceutical compositions containing a therapeutically effective amount of a compound of Formula I may be used to treat depression, anxiety, psychoses (for example schizophrenia), tardive dyskinesia, obesity, drug addiction, drug abuse, cognitive disorders, Alzheimer's disease, obsessive-compulsive behaviour, panic attacks, social phobias, eating disorders such as bulimia, anorexia, snacking and binge eating, non-insulin dependent diabetes mellitus, hyperglycaemia, hyperlipidaemia, stress in mammals particularly humans, as an aid to smoking cessation in human beings and in the treatment and/or prophylaxis of seizures, neurological disorders such as epilepsy and/or conditions in which there is neurological damage such as stroke, brain trauma, cerebral ischaemia, head injuries and haemorrhage. Whilst the precise amount of active compound administered in such treatment will depend on a number of factors, for example the age of the patient, the severity of the condition and the past medical history, and always lies within the sound discretion of the administering physician, the amount of active compound administered per day is in the range 1 to 1000 mg preferably 5 to 500 mg given in single or divided doses at one or more times during the day.

In yet another aspect, the present invention provides the use of a compound of Formula I in the manufacture of a medicament for use in the treatment of depression, anxiety, psychoses (for example schizophrenia), tardive dyskinesia, obesity, drug addiction, drug abuse, cognitive disorders, Alzheimer's disease, obsessive-compulsive behaviour, panic attacks, social phobias, eating disorders such as bulimia, anorexia, snacking and binge eating, non-insulin dependent diabetes mellitus, hyperglycaemia, hyperlipidaemia, stress, as an aid to smoking cessation and in the treatment and/or prophylaxis of seizures, neurological disorders such as epilepsy and/or conditions in which there is neurological damage such as stroke, brain trauma, cerebral ischaemia, head injuries and haemorrhage.

The present invention also provides a method of treating depression, anxiety, psychoses (for example schizophrenia), tardive dyskinesia, obesity, drug addiction, drug abuse, cognitive disorders, Alzheimer's disease, obsessive-compulsive behaviour, panic attacks, social phobias, eating disorders such as bulimia, anorexia, snacking and binge eating, non-insulin dependent diabetes mellitus, hyperglycaemia, hyperlipidaemia, stress and seizures, neurological disorders such as epilepsy and/or conditions in which there is neurological damage such as stroke, brain trauma, cerebral ischaemia, head injuries and haemorrhage which comprises the administration of a therapeutically effective amount of a compound of Formula I to a patient in need thereof.

The present invention also provides a method of reducing the craving to smoke in human beings which comprises the administration of a therapeutically effective amount of a compound of Formula I to a patient in need thereof. The present invention also provides a method of reducing weight gain after smoking cessation in human beings which comprises the administration of a therapeutically effective amount of a compound of Formula I to a patient in need thereof.

In addition the compounds of the present invention may be useful in the treatment or prevention of metabolic diseases and conditions arising therefrom, for example non exercise activity thermogenesis and increased metabolic rate, sexual dysfunction, sleep apnoea, premenstrual syndrome, urinary incontinence, hyperactivity disorders, hiatial hernia and reflux esophagitis, pain, especially neuropathic pain, weight gain associated with drug treatment, chronic fatigue syndrome, osteoarthritis and gout, cancers associated with weight gain, menstrual dysfunction, gallstones, orthostatic hypotension and pulmonary hypertension.

The compounds of the present invention may be useful in preventing cardiovascular disease, and in reducing platelet adhesiveness, in aiding weight loss after pregnancy and in aiding weight loss after smoking cessation.

Processes for the preparation of compounds of Formula I will now be described. The processes may be performed on an individual basis, or by multiple parallel synthesis, also known as High Speed Analoguing. The processes are preferably carried out at atmospheric pressure.

Compounds of Formula I may be prepared by methods analogous to those disclosed in WO 97/02269. Additionally compounds of Formula I may be prepared by methods described below.

Compounds of Formula I may be prepared by dehydrating a compound of Formula VII

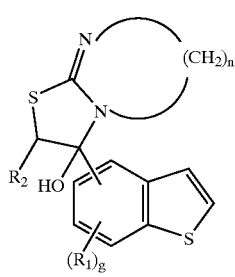

VII in which $R_1$, $R_2$, g and n are as hereinbefore defined, optionally in the presence of an acid, for example acetic or sulphuric acid, and optionally in the presence of a second dehydrating agent, for example acetic anhydride, at a temperature in the range 0–200° C.; preferably in the range 20–150° C.

Compounds of Formula VII may be prepared by reacting a compound of Formula VIII

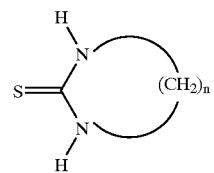

VIII in which n is as hereinbefore defined, with a compound of Formula IX

IX in which Z is a leaving group, for example a halo such as bromo, and $R_1$, $R_2$ and g are as hereinbefore defined, at a temperature in the range 0–200° C., in the presence of a solvent, for example ethanol and optionally in the presence of an acid, for example acetic acid; preferably by heating at a temperature in the range 20° C. to the boiling point of the solvent used.

Compounds of Formula I may also be prepared directly by reacting a compound of Formula VII with a compound of Formula IX at a temperature in the range of 0–200° C., optionally in the presence of an acid, for example acetic acid, and optionally in the presence of a solvent, for example ethanol, without isolation of the intermediate of Formula VII; preferably by heating at a temperature in the range 20–150° C.

Compounds of Formula I may also be prepared directly by reacting a compound of Formula VII with a compound, analogous to a compound of Formula IX but in which Z is not a leaving group but H, in the presence of a solvent, for example acetic acid, and an acid, for example sulphuric or hydrochloric acid, and optionally in the presence of a second dehydrating agent, for example acetic anhydride, at a temperature in the range 0–200° C.; preferably in the range 20–150° C.

Compounds of Formula I in which $R_2$ represents halo may be prepared by reacting a compound of Formula X

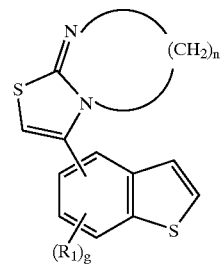

X in which $R_1$, n and g are as hereinbefore defined, with a halogenating agent for example bromine, phenyltrimethylammonium tribromide or benzyltrimethylammonium tetrachloroiodate at a temperature in the range −50–200° C. optionally in the presence of a solvent, for example dichloromethane, tetrahydrofuran or acetone.

Compounds of Formula I in which $R_2$ represents a group of Formula —CH(OH)$R_x$ in which $R_x$ is a $C_{1-5}$ alkyl group, an alkenyl group containing 2–5 carbon atoms, an alkynyl group containing 2–5 carbon atoms or an aryl group may be prepared by reacting a compound of Formula XI

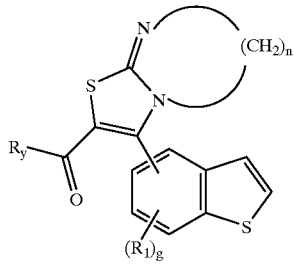

XI in which $R_1$, n and g are as hereinbefore defined and $R_y$ is H with an organometallic reagent, for example a compound of formula $R_xMgX$ or $R_xLi$ in which $R_x$ is as hereinbefore defined and X is halo, for example bromo, in the presence of a solvent, for example tetrahydrofuran or ether, at a temperature in the range of −50° C. to the boiling point of the solvent used.

Compounds of Formula I in which $R_2$ represents a group of Formula —CH(OH)$R_y$ in which $R_y$ is a $C_{1-5}$ alkyl group, an alkenyl group containing 2–5 carbon atoms, an alkynyl group containing 2–5 carbon atoms or an aryl group may be prepared by reacting a compound of Formula XI in which $R_1$, n and g are as hereinbefore defined and $R_y$ is a $C_{1-5}$ alkyl group, an alkenyl group containing 2–5 carbon atoms, an alkynyl group containing 2–5 carbon atoms or an aryl group with a reducing agent, for example sodium borohydride, in the presence of a solvent, for example ethanol, at a temperature in the range of 0° C. to the boiling point of the solvent used.

Compounds of Formula I in which $R_2$ is hydroxymethyl may be prepared by reacting a compound of Formula XI in which $R_1$, n and g are as hereinbefore defined and $R_y$ is H with a reducing agent, for example sodium borohydride, in a solvent, for example methanol, at a temperature in the range of −50° C. to the boiling point of the solvent used.

Compounds of Formula I in which $R_2$ represents a group of Formula —CH$_2R_x$ in which $R_x$ is H or a $C_{1-5}$ alkyl group may be prepared by reacting a compound of Formula XI in which $R_1$, n and g are as hereinbefore defined and $R_y$ is H or a $C_{1-5}$ alkyl group with a reducing agent, for example borane-dimethylamine complex, in the presence of a Lewis acid catalyst, for example aluminium chloride, and a solvent, for example dichloromethane, at a temperature in the range of −50° C. to the boiling point of the solvent used.

Compounds of Formula I in which $R_2$ is hydroxyiminomethyl may be prepared by reacting a compound of Formula XI in which $R_1$, n and g are as hereinbefore defined and $R_y$ is H with hydroxylamine or a salt thereof optionally in the presence of a solvent, for example an alcohol, e.g. ethanol, at a temperature in the range of 0–250° C.

Compounds of Formula I in which $R_2$ is cyano may be prepared by reacting a compound of Formula XI in which $R_1$, n and g are as hereinbefore defined and $R_y$ is H with hydroxylamine or a salt thereof in the presence of formic acid at a temperature in the range of 0–250° C.

Compounds of Formula I in which $R_2$ represents a $C_{1-4}$alkyliminomethylene group may be prepared by reacting a compound of Formula XI in which $R_1$, n and g are as hereinbefore defined and $R_y$ represents hydrogen with an amine of formula $R_aNH_2$ wherein $R_a$ represents a $C_{1-4}$ alkyl group optionally in the presence of a solvent, for example an alcohol e.g. ethanol, optionally in the presence of an acid catalyst for example, acetic acid, at a temperature in the range 0–250° C.

Compounds of Formula I in which $R_2$ represents a $C_{1-4}$alkylaminomethylene group may be prepared by reacting a compound of Formula I in which $R_2$ represents a $C_{1-4}$alkyliminomethylene group with a reducing agent, for example sodium borohydride, in the presence of a solvent, for example an alcohol e.g. ethanol, at a temperature in the range 0° C. to the boiling point of the solvent used.

Compounds of Formula I in which $R_2$ represents a $C_{1-4}$alkylaminomethylene group may be prepared directly from a compound of Formula XI in which $R_1$, n and g are as hereinbefore defined and $R_y$ represents hydrogen by reaction with an amine of formula $R_aNH_2$ wherein $R_a$ represents a $C_{1-4}$ alkyl group and a reducing agent, for example sodium triacetoxyborohydride, in the presence of a solvent, for example tetrahydrofuran, at a temperature in the range 0° C. to the boiling point of the solvent used.

Compounds of Formula I in which $R_2$ represents a group of formula —C(OH)$R_xR_y$ in which $R_x$ and $R_y$ are each independently a $C_{1-5}$ alkyl group may be prepared by reacting a compound of Formula XI in which $R_y$ is a $C_{1-5}$ alkyl group with an organometallic reagent, for example a compound of formula $R_xMgX$ or $R_xLi$ in which $R_x$ is as hereinbefore defined and X is halo, for example bromo, in the presence of a solvent, for example tetrahydrofuran or ether, at a temperature in the range of −50° C. to the boiling point of the solvent used.

Compounds of Formula I in which $R_2$ represents a group of formula —C(OH)$R_xR_y$ in which $R_x$ and $R_y$ are the same $C_{1-2}$ alkyl group may be prepared by reacting a compound of Formula XI, as hereinbefore defined except that $R_y$ is OR$_z$ in which $R_z$ is a $C_{1-6}$alkyl group, with an organometallic reagent, for example a compound of formula $R_xMgX$ or $R_xLi$ in which $R_x$ is as hereinbefore defined and X is halo, for example bromo, in the presence of a solvent, for example tetrahydrofuran or ether, at a temperature in the range of −50° C. to the boiling point of the solvent used.

Compounds of Formula I in which $R_2$ represents a $C_{2-6}$ alkenyl group in which the double bond is attached to the carbon alpha to the thiazole ring or a styryl group may be prepared by reacting compounds of Formula XI, in which $R_y$ represents hydrogen or a $C_{1-4}$ alkyl group, with a phosphonium salt of formula $R_zPh_3P^+Br^-$ or a phosphonate of formula $R_zPO(OEt)_2$ in which $R_z$ represents a $C_{1-5}$ alkyl group or a benzyl group in the presence of a base, for example n-butyllithium or sodium hydride, in a solvent, for example an ether, e.g. tetrahydrofuran, at a temperature in the range −78° C. to the boiling point of the solvent used.

Compounds of Formula I in which $R_2$ represents a $C_{2-6}$ alkanoyl group may be prepared by reacting a compound of Formula I in which $R_2$ represents halo, for example bromo or chloro, or a compound of Formula X, with a metallating agent for example a compound of formula $R_bMgX$ or $R_bLi$ in which $R_b$ is a $C_{1-6}$ alkyl group and X is halo, for example bromo or chloro, in the presence of a solvent, for example an ether, e.g. diethyl ether or tetrahydrofuran, at a temperature in the range −78° C. to the boiling point of the solvent used, and then reacting the product obtained with an acylating agent for example a compound of Formula $R_cCON(CH_3)OCH_3$ in which $R_c$ represents a $C_{1-5}$ alkyl group in a solvent, for example an ether e.g. tetrahydrofuran, at a temperature in the range 0° C. to the boiling point of the solvent used. Compounds of Formula XI may be prepared in a similar manner.

Compounds of Formula I in which $R_2$ represents a $C_{1-3}$alkoxy$C_{1-3}$ alkyl group may be prepared by reacting a compound of Formula I in which $R_2$ represents a hydroxy$C_{1-3}$ alkyl group with a $C_{1-3}$ alkylating agent, for example a $C_{1-3}$ alkyl halide e.g. a $C_{1-3}$ alkyl iodide, in the presence of a base, for example sodium hydride, in a solvent, for example N,N-dimethylformamide, at a temperature in the range of −50 to 150° C.

Compounds of Formula I in which $R_2$ represents a $C_{4-6}$cycloalkylalkoxy$C_{1-3}$alkyl group may be prepared by reacting a compound of Formula I in which $R_2$ represents a hydroxy$C_{1-3}$ alkyl group with a $C_{4-6}$ cycloalkylalkylating agent, for example a $C_{4-6}$ cycloalkylalkyl halide e.g. a $C_{4-6}$ cycloalkylalkyl iodide in the presence of a base, for example sodium hydride, in a solvent, for example N,N-dimethylformamide, at a temperature in the range of −50 to 150° C.

Compounds of Formula I in which $R_2$ represents a $C_{3-4}$alkynylalkoxy$C_{1-3}$alkyl group may be prepared by reacting a compound of Formula I in which $R_2$ represents a hydroxy$C_{1-3}$ alkyl group with a $C_{3-4}$ alkynylalkylating agent, for example a $C_{3-4}$ alkynylalkyl halide e.g. a $C_{3-4}$ alkynylalkyl iodide in the presence of a base, for example sodium hydride, in a solvent, for example N,N-dimethylformamide, at a temperature in the range of −50 to 150° C.

Compounds of Formula I in which $R_2$ represents a $C_{1-3}$alkylthio$C_{1-3}$alkyl group may be prepared by reacting a compound of Formula I in which $R_2$ represents a mercapto$C_{1-3}$ alkyl group with a $C_{1-3}$ alkylating agent, for example a $C_{1-3}$ alkyl halide e.g. a $C_{1-3}$ alkyl iodide in the presence of a base, for example sodium hydride or sodium hydroxide, in a solvent, for example N,N-dimethylformamide, at a temperature in the range of −50 to 150° C.

Compounds of Formula I in which $R_2$ represents a $C_{1-3}$ alkylthio group or an arylthio group and $R_1$, n and g are as previously defined may be prepared by reacting a compound of Formula I in which $R_2$ represents halo, or a compound of Formula X, with a metallating agent, for example a compound of formula RMgX or RLi in which R is a $C_{1-6}$ alkyl group and X is halo, for example chloro, bromo or iodo, in a solvent, for example an ether or a mixture of ethers, eg tetrahydrofuran or diethyl ether, at a temperature in the range of −100° C. to the boiling point of the solvent used to give an intermediate complex, which is reacted with a disulphide of formula $R_dS$—$SR_d$ in which $R_d$ is a $C_{1-3}$ alkyl group or an aryl group, at a temperature in the range of −100° C. to the boiling point of the solvent used.

Compounds of Formula I in which $R_2$ represents a $C_{1-3}$ alkoxy group and $R_1$, n and g are as previously defined may be prepared by reacting a compound of Formula I in which $R_2$ represents halo, for example bromo or iodo, with an $C_{1-3}$ alkoxide salt, for example a sodium or potassium salt, optionally in the presence of a solvent, for example a $C_{1-3}$ alcohol or dimethylformamide, optionally in the presence of a catalyst, for example a copper (I) salt, at a temperature in the range of 0–350° C.

Compounds of Formula VIII are commercially available.

Compounds of Formula IX in which Z is halo may be prepared by reaction of a compound of Formula XII

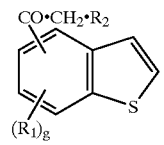

XII in which $R_1$, $R_2$ and g are as hereinbefore defined, with a halogenating agent, for example a brominating agent such as phenyltrimethylammonium tribromide, sodium bromate or copper(II) bromide, at a temperature in the range 0–200° C. in the presence of a solvent, for example tetrahydrofuran; preferably at a temperature in the range 20–150° C.

Compounds of Formula XII may be prepared by the reaction of a compound of Formula XIII

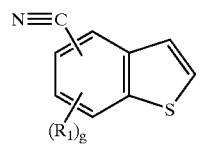

XIII in which $R_1$ and g are as hereinbefore defined with an organometallic reagent, for example a compound of formula $R_2CH_2MgX$ in which $R_2$ is as hereinbefore defined and X is halo, for example bromo, in the presence of a solvent, for example tetrahydrofuran or ether, at a temperature in the range of −50° C. to the boiling point of the solvent used, followed by hydrolysis of the intermediate imine salt optionally in the presence of an acid catalyst, for example hydrochloric acid.

Compounds of Formula XII may also be prepared by other methods known to those skilled in the art and as specified in the individual Examples described herein.

Compounds of Formula XII in which the cyano-group is attached at the 4-position of the benzo[b]thiophene may be prepared by the reaction of a compound of Formula XIV

XIV in which $R_1$ and g are as hereinbefore defined with an oxidising agent such as 2,3-dichloro-5,6-dicyano-1,4-benzoquinone, in the presence of a solvent, for example toluene, at a temperature in the range of 0° C. to the boiling point of the solvent used.

Compounds of Formula XIV may be prepared by the reaction of a compound of Formula XV

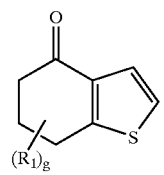

XV in which $R_1$ and g are as hereinbefore defined with a source of cyanide, for example trimethylsilyl cyanide, optionally in the presence of an acid, for example a Lewis acid such as boron trifluoride etherate, and optionally in the presence a solvent, for example toluene, at a temperature in the range of 0–250° C., followed by reaction with a reagent capable of generating a double bond, for example phosphorous oxychloride, or an acid, such as 4-toluenesulphonic acid, optionally in the presence of a solvent, for example toluene, at a temperature in the range of 0–250° C.

The methods described above to prepare compounds of Formula XIII in which $R_1$ and g are as hereinbefore defined and in which the cyano-group is attached at the 4-position of benzo[b]thiophene may be used to prepare compounds of Formula XII in which the cyano-group is attached at the 5-, 6- or 7-position by starting from the appropriate dihydrobenzo[b]thiophenone having the Formula XVI, XVII or XVIII

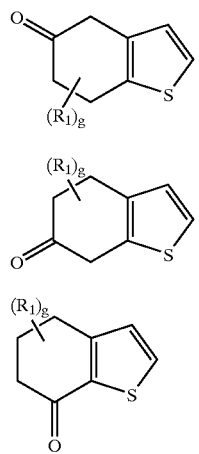

XVI

XVII

XVIII in which $R_1$ and g are as hereinbefore defined.

Compounds of Formula XV, XVI, XVII or XVIII are commercially available or may be prepared by methods known to those skilled in the art.

The ability of compounds of Formula I to interact with 5-hydroxytryptamine (5-HT) receptors has been demonstrated for the products of Examples 1 to 39 by the following test which determines the ability of the compounds to inhibit tritiated ligand binding to 5-HT receptors in vitro and in particular to $5\text{-HT}_{1A}$ receptors.

Hippocampal tissue from the brains of male Sprague-Dawley rats (Charles River; weight range 150–250 g) was homogenised in ice-cold 50 mM Tris-HCl buffer (pH 7.7 when measured at 25° C., 1:40 w/v) and centrifuged at 40,000 g at 4° C. for 10 minutes. The pellet was rehomogenised in the same buffer, incubated at 37° C. for 10 minutes and centrifuged at 40,000 g at 4° C. for 10 minutes. The final pellet was resuspended in 50 mM Tris-HCl buffer (pH 7.7) containing 4 mM $CaCl_2$, 0.1% L-ascorbic acid and 10 µM pargyline hydrochloride (equivalent to 6.25 mg wet weight of tissue/ml) and used immediately in the binding assay.

Membranes (400 µl; equivalent to 2.5 mg wet weight of tissue/tube) were incubated with 50 µl of [$^3$H]8-hydroxy-2-(dipropylamino)tetralin ([$^3$H]8-OH-DPAT) at a single concentration of 1 nM and 50 µl of distilled water (total binding) or 50 µl of test compound (at a single concentration of $10^{-6}$ M or at 10 concentrations ranging from $10^{-11}$–$10^{-3}$ M) or 50 µl of 5-HT (10 µM, non-specific binding) at 25° C. for 30 minutes. The incubation was terminated by rapid filtration under vacuum through Skatron 11734 filters using a Skatron Cell Harvester. Filters were washed with ice-cold 50 mM Tris-HCl buffer, pH 7.7 (at 25° C., wash setting 9,9,0). The scored filter paper discs were punched out into vials, scintillation fluid added and radioactivity determined by liquid scintillation counting.

The ability of compounds of Formula I to interact with 5-hydroxytryptamine (5-HT) reuptake sites has been demonstrated for the products of Examples 1 to 39 by the following test which determines the ability of compounds to displace the standard ligand, [$^3$H]citalopram, from 5-HT reuptake sites in vitro.

Frontal cortical tissue from the brains of male Charles River rats weighing 150–250 g was homogenised in ice-cold 50 mM Tris-HCl, pH 7.4 (when measured at 25° C.) containing 120 mM sodium chloride and 5 mM potassium chloride (Tris buffer; 1:30 w/v) and centrifuged at 40,000 g for 10 minutes. The supernatant was discarded and the pellet rehomogenised in Tris buffer, 1:60 w/v, and centrifuged at 40,000 g for 10 minutes. This step was repeated a further time. The final pellet was resuspended in 50 mM Tris-HCl, pH 7.4 containing 120 mM sodium chloride and 5 mM potassium chloride (equivalent to 3.125 mg wet weight of tissue/ml) and used immediately in the binding assay. All centrifugations were performed at 4° C.

Membranes (400 µl; equivalent to 1.25 mg wet weight of tissue/tube) were incubated with 50 µl [$^3$H]citalopram at a single concentration of 1.3 nM and 50 µl of distilled water (total binding) or 50 µl of test compound (at a single concentration of $10^{-6}$ M or at 10 concentrations ranging from $10^{-11}$–$10^{-3}$ M) or 50 µl of paroxetine (0.5 µM; non-specific binding) for 1 h at 27° C. Membrane bound radioactivity was recovered by filtration under vacuum through Skatron 11734 filters presoaked in 0.5% PEI using a Skatron Cell Harvester. Filters were then washed in ice-cold 50 mM Tris-HCl buffer, pH 7.4 (at 25° C., wash setting 9,9,0). The scored filter paper discs were punched out into vials, scintillation fluid added and radioactivity determined by liquid scintillation counting.

The ability of compounds of Formula I to interact with noradrenaline (NA) reuptake sites has been demonstrated for the products of Examples 1 to 39 by the following test which determines the ability of compounds to displace the standard ligand, [$^3$H]nisoxetine, from noradrenaline reuptake sites in vitro.

Frontal cortical tissue from the brains of male Charles River rats weighing 150–250 g was homogenised in ice-cold 50 mM Tris-HCl, pH 7.4 (at 25° C.) containing 120 mM sodium chloride and 5 mM potassium chloride (Tris buffer; 1:60 w/v) using a Kinematic polytron (speed setting 6 for 10 seconds) and centrifuged at 40,000 g for 10 minutes. The supernatant was discarded and the pellet rehomogenised in Tris buffer, 1:60 w/v, and centrifuged at 40,000 g for 10 minutes. This step was repeated twice more so that, in total, the brain tissue was homogenised and centrifuged four times. The final pellet was resuspended in 50 mM Tris-HCl, pH 7.4 containing 300 mM sodium chloride and 5 mM potassium chloride (equivalent to 18.75 mg wet weight of tissue/ml) and used immediately in the binding assay. All centrifugations were performed at 4° C.

Membranes (400 µl; equivalent to 7.5 mg wet weight of tissue/tube) were incubated with 50 µl [$^3$H]nisoxetine at a single concentration of 0.6 nM and 50 µl of distilled water (total binding) or 50 µl⁻ of test compound (at a single concentration $10^{-6}$M or at 10 concentrations ranging from $10^{-11}$–$10^{-3}$ M) or 50 µl of mazindol (1 µM; non-specific binding) for 4 h at 4° C. Membrane bound radioactivity was recovered by filtration under vacuum through Skatron 11734 filters using a Skatron cell harvester. Filters were rapidly washed with ice-cold 50 mM Tris-HCl, pH 7.4 containing 120 mM sodium chloride and 5 mM potassium chloride (wash setting 9,9,0). The scored filter paper discs were punched out into vials, scintillation fluid added and radioactivity determined by liquid scintillation counting.

The ability of compounds of Formula I to interact with muscarinic receptors has been demonstrated for the products of Examples 1–39 by the following test which determines the ability of compounds to displace the standard ligand, [3H]N-methylscopolamine, from muscarinic receptors in vitro.

Frontal cortical tissue from the brains of male Charles River rats weighing 150–250 g was homogenised in ice-cold 20 mM HEPES buffer, pH 7.5 (measured at 25° C.) containing 100 mM sodium chloride and 10 mM magnesium chloride (1:10 w/v) using a Polytron PT3100 (speed setting 21,700 rpm, 3×5 seconds) and centrifuged at 49,500 g for 30 minutes at 4° C. The supernatant was discarded and the pellet rehomogenised in 20 mM HEPES buffer, pH 7.5 containing 100 mM sodium chloride and 10 mM magnesium chloride (equivalent to 12.5 mg wet weight of tissue/ml). Membranes were stored at −80° C. until required.

Membranes were thawed, diluted 1:10 in ice-cold 20 mM HEPES buffer, pH 7.5 containing 100 mM sodium chloride and 10 mM magnesium chloride and homogenised using a Polytron PT3100 as above. Diluted membranes (200 μl; equivalent to 0.25 mg wet weight of tissue/tube) were incubated with 200 μl of 20 mM HEPES buffer, pH 7.5 containing 100 mM sodium chloride and 10 mM magnesium chloride and 50 μl [3H]N-methylscopolamine at a single concentration of 0.15 nM and 50 μl distilled water (total binding) or 50 μl test compound (at a single concentration of $10^{-6}$ M or at 10 concentrations ranging from $10^{-11}$–$10^{-3}$ M) or 50 μl atropine sulphate (1 μM; non-specific binding) for 30 min at 30° C. Membrane bound radioactivity was recovered by filtration under vacuum through Skatron 11734 filters using a Skatron cell harvester. Filters were rapidly washed with ice-cold 20 mM HEPES buffer, pH 7.5 (wash 1,2 at setting 5,5). The scored filter paper discs were punched out into vials, scintillation fluid added and radioactivity determined by liquid scintillation counting.

For each of these tests measuring the ability of compounds of Formula I to displace standard ligands from 5-HT$_{1A}$ receptors and 5-hydroxytryptamine (5-HT) and noradrenaline (NA) reuptake sites and muscarinic receptors in vitro, the percentage displacement of specific binding of tritiated ligand by $10^{-6}$ M test compound was calculated in the following way.

Firstly, specific binding of tritiated ligand in the absence (A) and presence (B) of test compound was determined:
In the absence of compound:

$A(dpm)$=Total binding $(dpm)$−Non-specific binding $(dpm)$

In the presence of compound ($10^{-6}$ M):

$B(dpm)$=Binding at $10^{-6}$M $(dpm)$−Non-specific binding $(dpm)$

The specific binding of tritiated ligand in the presence (B) of compound was then converted to a percentage of specific binding of tritiated ligand in the absence (A) of compound:

% Specific binding at $10^{-6}$ M=$B(dpm)/A(dpm)$×100

The percentage displacement of specific binding of tritiated ligand by the test compound ($10^{-6}$ M) was then obtained by subtraction of the percentage specific binding in the presence of compound from the percentage specific binding in the absence of compound, which is taken as the maximum binding and so equals 100%:

% Displacement at $10^{-6}$ M=100−% Specific binding at $10^{-6}$ M.

In some cases, displacement curves were then produced for compounds which displaced ≧50% of specific binding of the tritiated ligand at $10^{-6}$ M using a range of concentrations of the compound. The $K_i$ was then calculated by simultaneous fitting using equations derived from the Feldman equations by robust non-linear regression to data from three experiments simultaneously (De Lean et al., 1978; Munson and Rodbard, 1980; Feldman, 1992).

Munson P J and Rodbard D. Ligand: a versatile computerised approach for characterisation of ligand binding systems. Anal Biochem 1980; 107: 220.

Feldman HA. Mathematical theory of complex ligand binding systems at equilibrium: some methods for parameter fitting. Anal Biochem 1992: 48, 317.

De Lean A, Munson P J and Rodbard D. Simultaneous analysis of families of sigmoidal curves: application to bioassay, radioligand assay, and physiological dose-response curves. Am J Physiol 1978: 235 (2), E97-E102.

The results obtained in the above tests for 5-HT$_{1A}$ binding and 5-HT and NA uptake and muscarinic binding for the final products of Examples 1–39 hereinafter are given in Table 1 below. $K_i$s are in nM. % Figures are for % displacement at $10^{-6}$ M for a single determination.

TABLE 1

| Example No. | 5-HT$_{1A}$ | 5-HT uptake | NA uptake | Muscarinic |
|---|---|---|---|---|
| 1 | 60% | 97% | 103% | 7% |
| 2 | 86 | 45 | 9.1 | 20% |
| 3 | 20.4 | 175 | 2.9 | −3% |
| 4 | 2.2 | 36 | 25 | 0% |
| 5 | 55% | 95% | 100% | 42% |
| 6 | 9.7 | 44.4 | 21 | −2% |
| 7 | 11.7 | 127 | 9.5 | 17% |
| 8 | 14.3 | 275 | 6.1 | 0% |
| 9 | 15 | 387 | 5.9 | 13% |
| 10 | 5.9 | 29.3 | 69.5 | 12% |
| 11 | 80% | 97% | 92% | 44% |
| 12 | 52 | 16 | 5.8 | 22% |
| 13 | 15.5 | 84 | 3.6 | 371 |
| 14 | 64% | 96% | 87% | 9% |
| 15 | 97% | 75% | 18 | −15% |
| 16 | 97% | 93% | 83% | 0% |
| 17 | 82% | 84% | 84% | 29% |
| 18 | 96% | 96% | 29.5 | 12% |
| 19 | 134 | 39 | 5.3 | 2% |
| 20 | 98% | 73% | 47% | 16% |
| 21 | 31 | 92 | 5.5 | 9% |
| 22 | 88% | 85 | 1.5 | 439 |
| 23 | 20 | 229 | 4.0 | −5% |
| 24 | 76% | 97% | 39% | −10% |
| 25 | 92% | 169 | 5.4 | 249 |
| 26 | 90% | 64% | −3% | −11% |
| 27 | 88% | 85% | 72% | −1% |
| 28 | 38.5 | 148 | 5.4 | −8% |
| 29 | 83 | 4.1 | 3.7 | 798 |
| 30 | 66% | 95% | 101% | 12% |
| 31 | 102 | 35 | 4.3 | 26% |
| 32 | 93 | 223 | 3.5 | 331 |
| 33 | 99% | 62% | 84% | 38% |
| 34 | 45 | 53 | 2 | 76 |
| 35 | 151 | 83 | 5.5 | 492 |
| 36 | 40 | 89 | 1.7 | 66 |
| 37 | 2.1 | 213 | 7.4 | 9% |
| 38 | 29 | 61 | 1.2 | 12% |
| 39 | 85% | 70% | 100% | NT |

NT = Not tested

Especially preferred compounds of the present invention show reduced affinity for muscarinic receptors compared to Example 1 of WO97/02269 which has a $K_i$ of 130 nM. Muscarinic affinity may cause undesired side-effects, for example dry mouth, blurred vision, sweating, palpitations, constipation and aggravation of narrow angle glaucoma (Blackwell, B. Adverse effects of antidepressant drugs. Part 1 Monoamine oxidase inhibitors and tricyclics. Drugs 21, 202–219, 1981). It is desirable for compounds to have minimal affinity for muscarinic receptors.

The ability of compounds of the invention to inhibit monoamine oxidase A activity is demonstrable by the following test.

The assay was performed using the following general procedure in which the tissue source was human placenta:

| Enzyme | Substrate | Incubation | Reaction product | Method of detection |
|---|---|---|---|---|
| MAO-A(h) | Kynuramine (0.15 mM) | 30 min/ 30° C. | 4-OHquinoline | Spectrophotometry |

The compounds were tested at 1 and 10 micromolar in duplicate.

Ref: Weyler, W. and Salach, J. I. (1985) Purification and properties of mitochondrial monoamine oxidase type A from human placenta. J. Biol. Chem., 260: 13199–13207.

Especially preferred compounds of the present invention have significantly reduced $MAO_A$ inhibitory activity compared to compounds exemplified in WO97/02269.

The combination of inhibition of monoamine oxidase activity and 5-HT reuptake inhibition may cause serotonin syndrome (Sternbach, H. Serotonin syndrome. Am. J. Psychiatry 148, 705–713, 1991) which is highly undesirable.

Acute Feeding Studies

Animals and Environment

Experiments were performed on male Sprague-Dawley rats (300–450 g at the start of the experiment) which were obtained from Charles River (Margate). Animals were individually-housed in polypropylene cages with metal grid floors at a temperature of 21±1° C. and 55% humidity. Polypropylene trays were placed below each cage. Animals were maintained on a reverse phase light-dark cycle. Lights were off from 09.30 h to 17.30 h during which time the room was illuminated by red light. Animals had free access to a powdered rat diet and tap water at all times. The diet was contained in glass feeding jars (10 cm diameter; 8 cm deep) with aluminium lids. Each lid had a hole (3 cm diameter) cut in it to allow access to the food. Animals were accustomed to these conditions for at least two weeks before experimentation.

Test Procedure

On the day prior to testing, the animals were randomly allocated to treatment groups containing 6–8 rats, weighed and their food intakes over a 6 h period were measured. These baseline readings were taken to ensure that the body weights and food intakes of the different groups of rats were not significantly different before drug treatment. On the test day, animals were given vehicle or one of three doses of the test drug. All drugs were dosed orally at the onset of the dark phase since rats consume most of their food during this period. Feeding jars were weighed (to the nearest 0.1 g) at the time of drug administration and 1, 2, 4, 6 and 24 h after dosing. At each reading, the trays below the cages were examined for spilt food which was then returned to the feeding jar. However, spillage of food from the feeding jars was generally negligible.

All drug doses are expressed as the free base. Drugs were dissolved in deionised water or suspended in 0.4% cellosize using a sonic bath.

Data Analysis

Variations in body weight were accounted for by expressing the results as g/kg rat weight (treatment group means±s.e.mean). $ED_{50}$ values (the dose of a drug required to reduce food intake to 50% of the control values) were calculated from a logistic sigmoid curve using a dedicated computer program. Statistical comparisons between mean group intakes were made using analysis of variance and Dunnett's test (two-tailed).

Especially preferred compounds of the present invention have superior activity in acute feeding studies compared to compounds exemplified in WO97/02269.

The compounds of the present invention are particularly useful in treating obesity and related co-morbid conditions, for example, diabetes, hyperglycaemia and hyperlipidaemia.

It is known that monoamine reuptake inhibitors which are used to treat obesity are often associated with cardiovascular side effects, for example, increased heart rate and increased blood pressure. The compounds of the present invention reduce the cardiovascular side effects which might be expected to occur from the administration of a monoamine reuptake inhibitor particularly a noradrenaline reuptake inhibitor. Whilst not wishing to be bound by theory it is likely that the combination of $5\text{-}HT_{1A}$ agonism in the compounds of the present invention reduces the cardiovascular side effects which might have arisen from their monoamine reuptake inhibition particularly their noradrenaline reuptake inhibition.

In another aspect the present invention provides a method of reducing the cardiovascular side effects of an anti-obesity drug comprising incorporating into the compound $5\text{-}HT_{1A}$ agonism.

In another aspect the present invention provides the use of a compound which is a $5\text{-}HT_{1A}$ agonist and which is a monoamine reuptake inhibitor particularly a noradrenaline reuptake inhibitor in the treatment of obesity and related co-morbid conditions without causing cardiovascular side effects.

The beneficial properties of especially preferred compounds of the present invention in reducing cardiovascular side-effects were demonstrated in rat telemetry studies in which heart rate, blood pressure, body temperature and locomotor activity are recorded continuously over time. Suitable methods are described in:

Brockway, B P, Mills, P A & Azar, S H (1991) A new method for continuous chronic measurement of blood pressure, heart rate and activity in the rat via radio-telemetry. Clinical and Experimental Hypertension—Theory and Practice A13(5), 885–895 and Guiol, C, Ledoussal, C & Surgé, J-M (1992) A radiotelemetry system for chronic measurement of blood pressure and heart rate in the unrestrained rat. Validation of method. Journal of Pharmacological and Toxicological Methods 28, 99–105.

The $5\text{-}HT_{1A}$ agonism of especially preferred compounds of the present invention was determined by electrophysiology by methods known to those skilled in the art.

The invention is illustrated by the following Examples which are given by way of example only. The final product of each of these Examples was characterised by one or more of the following procedures: high performance liquid chromatography; elemental analysis, nuclear magnetic resonance spectroscopy, mass spectroscopy and infrared spectroscopy.

EXAMPLES

Example 1

Method A

A mixture of 4-chlorobenzo[b]thiophene-2-carboxylic acid (2 g prepared in a manner similar to that described in

*J. Chem. Res.* (S), 1978, 10), copper powder (0.82 g) and quinoline (20 ml) was stirred under nitrogen at 180° C. for 2 hours then cooled to ambient temperature and acidified by the addition of 2M hydrochloric acid (50 ml). The product was extracted into ether (50 ml), the extract was dried ($MgSO_4$) and the solvent was removed in vacuo. The residue was purified by flash chromatography over silica using a 5:1 mixture of petroleum ether (b.p. 60–80° C.) and ethyl acetate as eluant. Appropriate fractions were combined and the solvents removed in vacuo to give 4-chlorobenzo[b]thiophene (1.49 g) as a pale yellow oil which was used without further purification.

Bromoacetyl bromide (16.14 g) was added dropwise at 0° C. under nitrogen to a stirred mixture of anhydrous aluminium chloride (21.36 g) and dichloromethane (200 ml), then the mixture was stirred at 0° C. for 30 minutes. A solution of 4-chloro-benzo[b]thiophene (13.46 g; prepared in a manner similar to that described above) in dichloromethane (100 ml) was added dropwise, and the mixture was stirred at 0° C. for 2 hours then it was poured onto ice-water (500 ml). The product was extracted into dichloromethane (2×250 ml) and the combined extracts were washed with water (200 ml), saturated aqueous sodium hydrogencarbonate solution (2×200 ml) and saturated aqueous sodium chloride solution (200 ml), then dried ($Na_2SO_4$). The solvent was removed in vacuo to leave a brown oil, which was purified by flash chromatography over silica using a 10:1 mixture of petroleum ether (b.p. 60–80° C.) and ethyl acetate as eluant. Appropriate fractions were combined and the solvents removed in vacuo to give 2-bromo-1-(4-chlorobenzo[b]thiophen-2-yl]ethan-1-one (2.8 g) as a colourless solid which was used without further purification.

A mixture of 2-bromo-1-(4-chlorobenzo[b]thiophen-2-yl] ethan-1-one (2.5 g), 2-imidazolidinethione (0.88 g), acetic acid (25 ml) and ethanol (50 ml) was heated under reflux for 90 minutes, then cooled to 0° C. The resulting solid was collected by filtration and dried in vacuo at 60° C. for 2 hours to give 3-(4-chlorobenzo[b]thiophen-2-yl)-5,6-dihydroimidazo[-2,1-b]thiazole hydrobromide (2.15 g) as colourless solid, m.p. 261–263° C.

Method B

Methylmagnesium chloride (3M solution in tetrahydrofuran; 5.7 ml) was added under nitrogen to a stirred solution of 4-chloro-N-methoxy-N-methylbenzo[b]thiophene-2-carboxamide (4 g; prepared in a manner similar to that described in Example 18) in tetrahydrofuran (120 ml) then the mixture was allowed to stand at ambient temperature for 30 minutes, heated under reflux for 30 minutes and allowed to stand at ambient temperature for 30 minutes. Further methylmagnesium chloride (3M solution in tetrahydrofuran; 2.0 ml) was added and the mixture was allowed to stand at ambient temperature for 2 hours. Further methylmagnesium chloride (3M solution in tetrahydrofuran; 2.0 ml) was added and the mixture was allowed to stand at ambient temperature for 30 minutes. Water (200 ml) and 5M hydrochloric acid (15 ml) were added and the product was extracted into dichloromethane (3×80 ml). The combined extracts were dried ($MgSO_4$) and the solvents were removed in vacuo. The residue was purified by column chromatography over silica using dichloromethane as eluant. Appropriate fractions were combined and the solvents removed in vacuo to leave 1-(4-chloro-benzo[b]thiophen-2-yl]ethan-1-one (1.8 g) as an off-white solid, m.p. 113–115° C.

A mixture of 1-(4-chlorobenzo[b]thiophen-2-yl]ethan-1-one (1.67 g), phenyltrimethylammonium tribromide (2.98 g) and tetrahydrofuran (40 ml) was stirred under nitrogen at ambient temperature for 22.5 hours then it was filtered and diluted with water (150 ml). The product was extracted into dichloromethane (3×30 ml), the combined extracts were dried ($MgSO_4$) and the solvents were removed in vacuo. The residue was purified by flash chromatography over silica using dichloromethane as eluant. Appropriate fractions were combined and the solvents removed in vacuo to leave 2-bromo-1-(4-chlorobenzo[b]thiophen-2-yl]ethan-1-one (1.65 g) as an off-white solid, m.p. 116–118° C.

A mixture of 2-bromo-1-(4-chlorobenzo[b]thiophen-2-yl] ethan-1-one (0.42 g), 2-imidazolidinethione (0.11 g) and ethanol (9 ml) was heated under reflux for 20 minutes. Acetic acid (4 ml) was added and the mixture was heated under reflux for 17 hours then cooled in ice-water. The resulting solid was collected by filtration and dried in vacuo at 60° C. to give 3-(4-chlorobenzo[b]thiophen-2-yl)-5,6-dihydroimidazo[2,1-b]thiazole hydrobromide (0.37 g) as a white solid, m.p. 273–274° C.

Example 2

To a suspension of magnesium turnings (0.41 g) in tetrahydrofuran (5 ml) under nitrogen were added 1 ml of a solution of 4-bromobenzo[b]thiophene (3.45 g, prepared in a manner similar to that described in *Bull. Soc. Chim. Fr.*, 1966, 11, 3667) in tetrahydrofuran (15 ml) and a crystal of iodine. The mixture was stirred at 50–60° C. and once the reaction had initiated the rest of the bromobenzo[b] thiophene solution was added dropwise at 50–60° C. over 10 minutes. The mixture was stirred for a further 0.5 hour at 50–60° C. then cooled to 0° C. A solution of 2-chloro-N-methoxy-N-methylacetamide (2.2 g) in tetrahydrofuran (20 ml) was added dropwise at 0–5° C. over 15 minutes and the mixture was stirred at 0–5° C. for 1 hour. Saturated aqueous ammonium chloride solution (25 ml) was added, the mixture was stirred at ambient temperature for 10 minutes, then the aqueous layer was separated and shaken with ethyl acetate (50 ml). The combined organic phases were dried ($MgSO_4$) and the solvents were removed in vacuo. The residue was purified by flash chromatography over silica using a 19:1 mixture of petroleum ether (b.p. 60–80° C.) and ethyl acetate as eluant. Appropriate fractions were combined and the solvents removed in vacuo to give 1-(benzo[b]thiophen-4-yl)-2-chloroethan-1-one (1.15 g) as a pale yellow oil which was used without further purification.

A mixture of 1-(benzo[b]thiophen-4-yl)-2-chloroethan-1-one (1.15 g), 2-imidazolidinethione (0.57 g), ethanol (10 ml) and acetic acid (6 ml) was heated under reflux for 18 hours then cooled to ambient temperature. The solvents were removed in vacuo and the residue was triturated with ether (30 ml). The resulting solid was collected by filtration, washed with ether (30 ml) and dried in vacuo at 40° C. to give 3-(benzo[b]thiophen-4-yl)-5,6-dihydroimidazo[2,1-b] thiazole hydrochloride (1.73 g) as a cream solid, m.p. 246–249° C.

Example 3

Bromine (0.16 ml) was added dropwise at 0–5° C. over 5 minutes to a stirred solution of 3-(benzo[b]thiophen-4-yl)-5,6-dihydroimidazo[2,1-b]thiazole (0.8 g; prepared by basification of 1 g of the hydrochloride salt described in Example 2) in dichloromethane (50 ml), then the mixture was stirred at 0° C. for 10 minutes and at ambient temperature for 1.5 hours. The resulting solid was collected by filtration, washed with dichloromethane (30 ml) and dried in vacuo at 60° C. to give 3-(benzo[b]thiophen-4-yl)-2-bromo-5,6-dihydroimidazo[2,1-b]thiazole hydrobromide (1.28 g) as a pale yellow solid which was used without further purification.

3-(Benzo[b]thiophen-4-yl)-2-bromo-5,6-dihydroimidazo[2,1-b]thiazole hydrobromide (1.2 g) was added in portions under nitrogen at 5–10° C. over 5 minutes to a stirred solution of ethylmagnesium chloride (2.0 M solution in ether; 4.5 ml) in tetrahydrofuran (20 ml), then the mixture was stirred at 5–15° C. for 2 hours. Dimethylformamide (1.3 ml) was added at 5–10° C. over 5 minutes, then the mixture was stirred at ambient temperature for 3 hours, cooled to 15° C. and quenched by the cautious addition of saturated aqueous ammonium chloride solution (10 ml) and water (10 ml). Ethyl acetate (20 ml) was added and the mixture was stirred at ambient temperature for 18 hours. The product was extracted into ethyl acetate (2×50 ml) and the combined extracts were washed with saturated aqueous sodium chloride solution (50 ml), dried (MgSO$_4$), and the solvents were removed in vacuo. The residue was triturated with propan-2-ol (5 ml) and the resulting solid was collected by filtration, washed with propan-2-ol (5 ml) and dried in vacuo at 60° C. to give 3-(benzo[b]thiophen-4-yl)-5,6-dihydroimidazo[2,1-b]thiazole-2-carboxaldehyde (0.37 g) as a brown solid which was used without further purification.

Sodium borohydride (0.05 g) was added in portions over 2 minutes to a stirred suspension of 3-(benzo[b]thiophen-4-yl)-5,6-dihydroimidazo[2,1-b]thiazole-2-carboxaldehyde (0.36 g) in methanol (10 ml), then the mixture was stirred at ambient temperature for 1.5 hours. The solvent was removed in vacuo then water (20 ml) and ethyl acetate (30 ml) were added and the mixture was stirred at ambient temperature for 2 hours. The aqueous phase was separated and washed with ethyl acetate (30 ml), then the combined ethyl acetate solutions were dried (MgSO$_4$) and the solvent was removed in vacuo at 60° C. to give [3-(benzo[b]thiophen-4-yl)-5,6-dihydroimidazo[2,1-b]thiazol-2-yl]methanol (0.315 g) as a cream solid, m.p. 145–149° C.

Example 4

This Example was performed in a similar manner to Example 3. 3-(4-Chlorobenzo[b]thiophen-2-yl)-5,6-dihydroimidazo[2,1-b]-thiazole hydrobromide (1.5 g, see Example 1) was basified to give 3-(4-chlorobenzo[b]thiophen-2-yl)-5,6-dihydroimidazo[2,1-b]thiazole which was brominated to give 2-bromo-3-(4-chlorobenzo[b]thiophen-2-yl)-5,6-dihydroimidazo[2,1-b]thiazole hydrobromide (1.13 g) as a pale yellow solid, m.p. 227–229° C. This was reacted with ethylmagnesium chloride (2.0 M solution in ether; 3.75 ml) in tetrahydrofuran (20 ml) followed by dimethylformamide (0.83 ml) to give 3-(4-chlorobenzo[b]thiophen-2-yl)-5,6-dihydroimidazo[2,1-b]thiazole-2-carboxaldehyde. (0.65 g) as a red-brown solid after flash chromatography. This aldehyde was reduced with sodium borohydride (0.13 g) to give [3-(4-chlorobenzo[b]thiophen-2-yl)-5,6-dihydroimidazo[2,1-b]thiazol-2-yl]methanol (0.22 g) as a yellow solid, m.p. 170–172° C.

Example 5

4-Fluorobenzo[b]thiophene was prepared starting from methyl thioglycolate and 2,6-difluorobenzaldehyde and then following a similar procedure to that given for 4-bromobenzo[b]thiophene in Example 9.

A solution of bromine (9.2 ml) in dichloromethane (200 ml) was added dropwise under nitrogen at –5° C. over 30 minutes to a stirred mixture of 4-fluorobenzo[b]thiophene (24.7 g), sodium acetate (20 g) and dichloromethane (200 ml). The mixture was stirred at ambient temperature for 24 hours, then it was filtered and the solvent was removed in vacuo. The residue was dissolved in dichloromethane (50 ml), water (200 ml) and zinc dust (34.3 g) were added, then the mixture was stirred and heated under reflux for 10 hours, cooled to ambient temperature and filtered through Celite. The Celite was washed with ethyl acetate (200 ml) then the combined organic solutions were washed with saturated aqueous sodium chloride solution (100 ml), dried (MgSO$_4$) and the solvents were removed in vacuo. The residue was purified by distillation in vacuo to give 3-bromo-4-fluorobenzo[b]thiophene (12.5 g) as a pale yellow oil, b.p. 70–85° C. @ 0.53 mbar.

A solution of 3-bromo-4-fluorobenzo[b]thiophene (0.76 g) in tetrahydrofuran (5 ml) was added dropwise under nitrogen at –60–-50° C. over 10 minutes to a stirred solution of n-butyllithium (2.5M solution in hexanes; 1.71 ml) in ether (40 ml), then the mixture was stirred at –50° C. for 30 minutes. A solution of 2-chloro-N-methoxy-N-methylacetamide (0.39 g) in tetrahydrofuran (10 ml) was added dropwise over 10 minutes, the mixture was stirred at –50° C. for 30 minutes and at 0° C. for 1 hour, then it was quenched by the addition of saturated aqueous ammonium chloride solution (30 ml). The organic layer was separated, washed with saturated aqueous sodium chloride solution (30 ml), dried (MgSO$_4$) and the solvent was removed in vacuo. The residue was purified by flash chromatography over silica using a 10:1 mixture of petroleum ether (b.p. 60–80° C.) and ethyl acetate as eluant. Appropriate fractions were combined and the solvents removed in vacuo to give 2-chloro-1-(4-fluorobenzo[b]thiophen-2-yl)ethan-1-one (0.1 g) as a colourless solid which was used without further purification.

A mixture of 2-chloro-1-(4-fluorobenzo[b]thiophen-2-yl]ethan-1-one (0.16 g; prepared in a manner similar to that described above), 2-imidazolidinethione (0.071 g), acetic acid (10 ml) and ethanol (5 ml) was heated under reflux for 2 hours then cooled to ambient temperature. The solvents were removed in vacuo and the residue was triturated with ether (10 ml). The resulting solid was collected by filtration and dried in vacuo at 60° C. for 2 hours to give 3-(4-fluorobenzo[b]thiophen-2-yl)-5,6-dihydroimidazo[2,1-b]thiazole hydrochloride (0.19 g) as pale pink solid, m.p. 220–224° C.

Example 6

Potassium carbonate (249.6 g) was added in portions at 0° C. over 7 minutes to a solution of N,O-dimethylhydroxylamine hydrochloride (100 g) in water (1000 ml), then toluene (1000 ml) was added and the mixture was stirred until the internal temperature reached 2° C. Propionyl chloride (86 ml) was added dropwise over 20 minutes, then the mixture was stirred at 0° C. for 30 minutes and at ambient temperature for 2 hours. The organic layer was separated, washed with water (500 ml) and saturated aqueous sodium chloride solution (500 ml), then the combined aqueous phases were shaken with ether (2×300 ml). The combined ether solutions were washed with water (500 ml) and saturated aqueous sodium chloride solution (500 ml), then the ether and toluene extracts were combined, dried (Na$_2$SO$_4$) and the solvents were removed in vacuo to give N-methoxy-N-methylpropionamide (73.0 g) as a pale yellow oil which was used without further purification.

n-Butyllithium (1.6 M solution in hexanes; 28.9 ml) was added dropwise under nitrogen at 0° C. to a stirred solution of benzo[b]thiophene (6.21 g) in ether (90 ml), then the mixture was stirred 0° C. for 15 minutes and cooled to –70° C. A solution of N-methoxy-N-methylpropionamide (5.42 g) in ether (40 ml) was added over 10 minutes, then the mixture was allowed to warm to ambient temperature and was stirred at ambient temperature for 3.5 hours. The mixture was poured into saturated aqueous ammonium chloride solution (200 ml) and ethyl acetate (100 ml) and water (50 ml) were added. The organic phase was separated, washed with saturated aqueous sodium chloride solution (150 ml), dried (Na$_2$SO$_4$) and the solvents were removed in vacua. The residue was triturated with petroleum ether (b.p. 40–60° C.) (25 ml) and the resulting solid was collected by filtration and dried in vacuo to give 1-(benzo[b]thiophen-2-yl)propan-1-one (7.05 g) as a colourless solid, m.p. 79–81° C.

Phenyltrimethylammonium tribromide (7.52 g) was added in portions under nitrogen at 0° C. to a stirred solution of 1-(benzo[b]thiophen-2-yl)propan-1-one (3.80 g) in tetrahydrofuran (80 ml), then the mixture was stirred at ambient temperature for 2 hours. Further phenyltrimethylammonium tribromide (0.15 g) was added, the mixture was stirred at ambient temperature for 2 hours, then it was filtered and the solvent was removed in vacuo. The residue was dissolved in ethanol (100 ml), 2-imidazolidinethione (2.04 g) was added and the mixture was heated under reflux for 10 minutes. Acetic acid (50 ml) was added, the mixture was heated under reflux for 16 hours, then it was allowed to cool to ambient temperature and the solvents were removed in vacua. The residue was triturated with ethanol (20 ml) and the resulting solid was collected by filtration, dried in vacuo at 100° C. for 3 hours, then recrystallised from ethanol to give 3-(benzo[b]thiophen-2-yl)-2-methyl-5,6-dihydroimidazo[2,1-b]thiazole hydrobromide (3.47 g) as a colourless solid, m.p. 257–259° C. (decomposes).

Example 7

A solution of 3-bromo-4-fluorobenzo[b]thiophene (3.0 g) in tetrahydrofuran (10 ml) was added dropwise under nitrogen at −60—70° C. over 10 minutes to a stirred solution of n-butyllithium (2.5M solution in hexanes; 6.75 ml) in ether (30 ml), then the mixture was stirred at −70° C. for 30 minutes. A solution of N-methoxy-N-methylpropionamide (1.31 g) in tetrahydrofuran (10 ml) was added dropwise at −70° C. over 10 minutes, then the mixture was stirred at −70° C. for 5 hours and allowed to stand at ambient temperature for 12 hours. The mixture was quenched by the addition of saturated aqueous ammonium chloride solution (40 ml), then the organic layer was separated, washed with saturated aqueous sodium chloride solution (40 ml), dried (MgSO$_4$) and the solvents were removed in vacuo. The residue was purified by flash chromatography over silica using a 10:1 mixture of petroleum ether (b.p. 60–80° C.) and ethyl acetate as eluant. Appropriate fractions were combined and the solvents removed in vacuo to give 1-(4-fluorobenzo[b]thiophen-2-yl)propan-1-one (0.54 g) as a colourless solid which was used without further purification.

Phenyltrimethylammonium tribromide (0.98 g) was added in portions under nitrogen at 0° C. over 10 minutes to a stirred solution of 1-(4-fluorobenzo[b]thiophen-2-yl)propan-1-one (0.54 g) in tetrahydrofuran (15 ml) then the mixture was stirred at 0° C. for 5 hours. Further phenyltrimethylammonium tribromide (0.49 g) was added, and the mixture was stirred at 0° C. for 3 hours then allowed to stand at ambient temperature for 12 hours. Further phenyltrimethylammonium tribromide (0.49 g) was added, the mixture was stirred at ambient temperature for 3 hours, then it was filtered through a bed of silica. The solvent was removed in vacuo to give 2-bromo-1-(4-fluorobenzo[b]thiophen-2-yl)propan-1-one (0.67 g) as a colourless solid which was used without further purification.

A mixture of 2-bromo-1-(4-fluorobenzo[b]thiophen-2-yl)propan-1-one (0.67 g), 2-imidazolidinethione (0.24 g), acetic acid (10 ml) and ethanol (5 ml) was heated under reflux for 2 hours then cooled to 20° C. The mixture was concentrated in vacuo and the resulting solid was collected by filtration, washed with ethanol (5 ml) and dried in vacuo at 60° C. for 2 hours to give 3-(4-fluorobenzo[b]thiophen-2-yl)-2-methyl-5,6-dihydroimidazo[2,1-b]thiazole hydrobromide (0.82 g) as beige solid, m.p. 224–226° C.

Example 8

Approximately 3 ml of a solution of 4-bromobenzo[b]thiophene (1.85 g; prepared in a manner similar to that described in *Bull. Soc. Chim. Fr.*, 1966, 111, 3667–3674) in tetrahydrofuran (20 ml) was added under nitrogen to a mixture of magnesium turnings (0.22 g) and tetrahydrofuran (2 ml). Two crystals of iodine were added and heat was applied to initiate the reaction. The remainder of the 4-bromobenzo[b]thiophene solution was added at reflux temperature over 20 minutes, the mixture was heated under reflux for 10 minutes, then it was cooled to ambient temperature. A solution of N-methoxy-N-methylpropionamide (1.01 g) in tetrahydrofuran (10 ml) was added, the mixture was heated under reflux for 30 minutes, then it was cooled to ambient temperature and quenched by the addition of 2M hydrochloric acid (25 ml). The mixture was allowed to stand at ambient temperature for 18 hours, then the tetrahydrofuran was removed in vacuo, the residue was diluted with water (50 ml) and the product was extracted into ethyl acetate (50 ml). The extract was washed with saturated aqueous sodium chloride solution (2×50 ml), dried (Na$_2$SO$_4$), and the solvents were removed in vacuo. The residue was purified by flash chromatography over silica using a 97:3 mixture of petroleum ether (b.p. 40–60° C.) and ethyl acetate as eluant. Appropriate fractions were combined and the solvents removed in vacuo to give 1-(benzo[b]thiophen-4-yl)propan-1-one (0.615 g) as a colourless oil which was used without further purification.

Phenyltrimethylammonium tribromide (1.198 g) was added in portions under nitrogen over 10 minutes to a stirred solution of 1-(benzo[b]thiophen-4-yl)propan-1-one (0.60 g) in tetrahydrofuran (20 ml), then the mixture was stirred at ambient temperature for 1 hour. Further phenyltrimethylammonium tribromide (0.10 g) was added, the mixture was stirred at ambient temperature for 30 minutes, then it was filtered and the solvent was removed in vacuo. The residue was dissolved in ethanol (20 ml), 2-imidazolidinethione (0.327 g) was added and the mixture was heated under reflux for 10 minutes. Acetic acid (10 ml) was added, the mixture was heated under reflux for 65 hours, then the solvents were removed in vacuo. The residue was triturated with ethanol (5 ml) and the resulting solid was collected by filtration and recrystallised from ethanol to give 3-(benzo[b]thiophen-4-yl)-2-methyl-5,6-dihydroimidazo[2,1-b]thiazole hydrobromide (0.52 g) as a colourless solid, m.p. 255–258° C.

Example 9

Method A n-Butyllithium (2.5 M solution in hexanes; 91 ml) was added dropwise under nitrogen at 0° C. to a stirred solution of diisopropylamine (35 ml) in tetrahydrofuran (450 ml), then the mixture was cooled to −75° C., 3-bromofluorobenzene (25 ml) was added over 10 minutes and the mixture was stirred at −75° C. for 1 hour. Dimethylformamide (19.3 ml) was added dropwise at −70° C. over 5 minutes, the mixture was stirred for 10 minutes, then acetic acid (20 ml) and water (700 ml) were added. The mixture was allowed to warm to 10° C. and the product was extracted into ether (500+300 ml). The combined extracts were washed with water (2×500 ml), 0.2M hydrochloric acid (500 ml) and saturated aqueous sodium chloride solution (2×250 ml), then they were dried ($Na_2SO_4$) and the solvents were removed in vacuo to give 2-bromo-6-fluorobenzaldehyde (40.18 g) as an off-white solid, m.p. 35–37° C.

Methyl thioglycolate (42.35 g) was added under nitrogen at 80° C. to a solution of triethylamine (109 ml) in dimethylformamide (290 ml), the mixture was stirred at 100° C. for 15 minutes, then a solution of 2-bromo-6-fluorobenzaldehyde (81.35 g; prepared in a manner similar to that described above) in dimethylformamide (70 ml) was added. The mixture was stirred at 130° C. for 5 hours, then it was cooled to ambient temperature and poured into ice-water (3000 ml). The resulting solid was collected by filtration, washed with water (2×250 ml) and dried in air to give methyl 4-bromobenzo[b]thiophene-2-carboxylate (101 g) as a yellow solid which was used without further purification.

A mixture of methyl 4-bromobenzo[b]thiophene-2-carboxylate (101 g), sodium hydroxide (63 g), methanol (1200 ml) and water (600 ml) was stirred at ambient temperature for 16 hours, the methanol was removed in vacuo, and the resulting suspension was cooled to 0° C. and acidified by dropwise addition of concentrated hydrochloric acid. The mixture was stirred for 20 minutes and the resulting solid was collected by filtration, washed with water (3×250 ml) and dried in vacuo at 110–120° C. to give 4-bromobenzo[b]thiophene-2-carboxylic acid (62 g) as a cream solid which was used without further purification.

A mixture of 4-bromobenzo[b]thiophene-2-carboxylic acid (21.05 g), copper powder (7.0 g) and quinoline (170 ml) was stirred at 180–190° C. for 1 hour, allowed to cool to ambient temperature and poured into 2M hydrochloric acid (900 ml). Ethyl acetate (500 ml) was added, the mixture was stirred for 15 minutes, then it was filtered through Celite. The aqueous phase was separated and shaken with ethyl acetate (200 ml), then the combined ethyl acetate solutions were washed with water (500 ml) and saturated aqueous sodium chloride solution (500 ml), dried ($Na_2SO_4$), and the solvents were removed in vacuo. The residue was purified by flash chromatography over silica using petroleum ether (b.p. 60–80° C.) as eluant. Appropriate fractions were combined and the solvents removed in vacuo to give 4-bromobenzo[b]thiophene (9.55 g) as a colourless oil which was used without further purification.

Approximately 5 ml of a solution of 4-bromobenzo[b]thiophene (9.55 g) in tetrahydrofuran (100 ml) was added under nitrogen to magnesium turnings (1.5 g). Two crystals of iodine were added and heat was applied to initiate the reaction. The remainder of the 4-bromobenzo[b]thiophene solution was added at reflux temperature over 20 minutes, then the mixture was heated under reflux for 15 minutes. A solution of N-methoxy-N-methylpropionamide (6.0 g) in tetrahydrofuran (50 ml) was added, the mixture was heated under reflux for 40 minutes, then it was allowed to cool to ambient temperature and quenched by the addition of 2M hydrochloric acid (125 ml). The mixture was stirred at ambient temperature for 1 hour, then the product was extracted into ethyl acetate (300 ml). The extract was washed with water (3×200 ml) and saturated aqueous sodium chloride solution (200 ml), dried ($Na_2SO_4$), and the solvents were removed in vacuo. The residue was purified by flash chromatography over silica using petroleum ether (b.p. 60–80° C.) followed by a 97:3 mixture of petroleum ether (b.p. 60–80° C.) and ethyl acetate as eluant. Appropriate fractions were combined and the solvents removed in vacuo to give 1-(benzo[b]thiophen-4-yl)propan-1-one (5.5 g) as a colourless oil which was used without further purification.

Phenyltrimethylammonium tribromide (18.9 g) was added in portions under nitrogen at 0° C. over 10 minutes to a stirred solution of 1-(benzo[b]thiophen-4-yl)propan-1-one (9.55 g; prepared in a manner similar to that described above) in tetrahydrofuran (170 ml), the mixture was stirred at ambient temperature for 3 hours, then it was filtered and the solvent was removed in vacuo. The residue was dissolved in ethanol (200 ml), 2-imidazolidinethione (5.10 g) was added, and the mixture was heated under reflux for 10 minutes. Acetic acid (100 ml) was added, the mixture was heated under reflux for 23 hours, then it was allowed to cool to ambient temperature and the solvents were removed in vacuo. The residue was triturated with a 1:1 mixture of ethanol and ether (50 ml) and the resulting solid was collected by filtration, washed with ether (30 ml) and dried in vacuo at 90° C. to give 3-(benzo[b]thiophen-4-yl)-2-methyl-5,6-dihydroimidazo[2,1-b]thiazole hydrobromide (15.5 g) as a colourless solid which was used without further purification.

A solution of sodium hydrogencarbonate (17.84 g) in water (300 ml) was added at 0° C. to a suspension of 3-(benzo[b]thiophen-4-yl)-2-methyl-5,6-dihydroimidazo[2,1-b]thiazole hydrobromide (15.0 g) in dichloromethane (300 ml), the mixture was stirred vigorously for 25 minutes, then the organic phase was separated, dried ($Na_2SO_4$), and the solvent was removed in vacuo. The residue was dissolved in ethanol (100 ml), the solution was cooled to 0° C., and 2M ethereal hydrogen chloride solution (28 ml) was added. The mixture was stirred for 20 minutes then the solvent was removed in vacuo. The residue was triturated with a 1:1 mixture of ethanol and ether (50 ml), then the resulting solid was collected by filtration and recrystallised from propan-2-ol to give 3-(benzo[b]thiophen-4-yl)-2-methyl-5,6-dihydroimidazo[2,1-b]thiazole hydrochloride (6.3 g) as a colourless solid, m.p. 235–238° C. Concentration of the liquor yielded a second crop of 3-(benzo[b]thiophen-4-yl)-2-methyl-5,6-dihydroimidazo[2,1-b]thiazole hydrochloride (2.7 g) as a colourless solid, m.p. 234–237° C.

Method B

Boron trifluoride diethyl etherate (120 drops) was added dropwise under nitrogen at ambient temperature to a stirred mixture of 6,7-dihydrobenzo[b]thiophen-4(5H)-one (130.5 g) and trimethylsilyl cyanide (98 g), the mixture was stirred at ambient temperature for 2 hours and at 100° C. for 1 hour, then it was allowed to stand at ambient temperature for 18 hours. Pyridine (650 ml) followed by phosphorus oxychloride (125 ml) were added, the mixture was heated at 140° C. for 2 hours whilst volatile materials were removed by distillation, then it was cooled to ambient temperature and added to crushed ice (2000 ml). Ether (2000 ml) was added and the mixture was filtered through Celite. The filter pad was washed with ether (500 ml), the aqueous phase was separated, and further product was extracted from it using ether (500 ml). The ethereal solutions were combined, washed with water (500 ml), 5M hydrochloric acid (2250+ 500 ml), water (500 ml) and saturated aqueous sodium chloride solution (500 ml), then they were dried ($MgSO_4$) and the solvents were removed in vacuo to give crude 6,7-dihydrobenzo[b]thiophene-4-carbonitrile (88.3 g) as an orange oil which was used without further purification.

A mixture of the crude 6,7-dihydrobenzo[b]thiophene-4-carbonitrile (88.3 g), 2,3-dichloro-5,6-dicyano-1,4-benzoquinone (120 g) and toluene (750 ml) was stirred at 80° C. for 2 hours then allowed to cool to ambient temperature. The resulting solid was removed by filtration and washed with toluene (500 ml). The filtrate and washings were combined, the solvent was removed in vacuo, and the residue was purified by Biotage flash chromatography over silica using 3–5% mixtures of ethyl acetate in petroleum ether (b.p. 60–80° C.) as eluant. Appropriate fractions were combined and the solvents were removed in vacuo to leave benzo[b]thiophene-4-carbonitrile (56.6 g) as a pale yellow solid which was used without further purification.

A solution of benzo[b]thiophene-4-carbonitrile (24.2 g) in ether (200 ml) was added under nitrogen over 10 minutes to ethylmagnesium chloride (2M solution in ether; 250 ml), then the stirred mixture was heated under reflux for 1 hour, cooled to ambient temperature and poured into crushed ice (100 ml). The mixture was stirred for 30 minutes, then 5M hydrochloric acid (250 ml) was added. The acidic layer was separated, heated to 90° C. for 20 minutes, then allowed to cool to ambient temperature. The product was extracted into ether (500+250 ml), the combined extracts were washed with water (250 ml) and saturated aqueous sodium chloride solution (150 ml), then they were dried ($MgSO_4$) and the solvent was removed in vacuo to give 1-(benzo[b]thiophen-4-yl)propan-1-one (18.25 g) as a colourless oil which was used without further purification.

1-(Benzo[b]thiophen-4-yl)propan-1-one (32.3 g; prepared in a manner similar to that described above) was reacted with phenyltrimethylammonium tribromide (63.9 g) followed by 2-imidazolidinethione (17.4 g) using methodology similar to that described in Example 9 Method A to give 3-(benzo[b]thiophen-4-yl)-2-methyl-5,6-dihydroimidazo[2,1-b]thiazole hydrobromide (46.8 g) as a colourless solid, m.p. 262–264° C. This was combined with a sample of 3-(benzo[b]thiophen-4-yl)-2-methyl-5,6-dihydroimidazo[2,1-b]thiazole hydrobromide (25.4 g) prepared according to the methodology described in Example 9 Method A. The combined sample was then basified and converted into the hydrochloride salt in a manner similar to that described in Example 9 Method A to give 3-(benzo[b]thiophen-4-yl)-2-methyl-5,6-dihydroimidazo[2,1-b]thiazole hydrochloride (46.8 g) as a colourless solid, m.p. 242–245° C.

Example 10

Ethylmagnesium bromide (1M solution in tetrahydrofuran; 17.2 ml) was added under nitrogen to a stirred solution of 4-chloro-N-methoxy-N-methylbenzo[b]thiophene-2-carboxamide (4 g; prepared in a manner similar to that described in Example 18) in tetrahydrofuran (120 ml) then the mixture was allowed to stand at ambient temperature for 30 minutes, heated under reflux for 30 minutes and allowed to stand at ambient temperature for 30 minutes. Further ethylmagnesium bromide (1M solution in tetrahydrofuran; 7.0 ml) was added and the mixture was allowed to stand at ambient temperature for 2 hours. Water (200 ml) and 5M hydrochloric acid (15 ml) were added, and the product was extracted into dichloromethane (2×90 ml). The combined extracts were dried ($MgSO_4$) and the solvents were removed in vacuo. The residue was purified by column chromatography over silica using dichloromethane as eluant. Appropriate fractions were combined and the solvents removed in vacuo to leave 1-(4-chlorobenzo[b]thiophen-2-yl)propan-1-one (1.88 g) as a pale yellow solid, m.p. 96–98° C.

A mixture of 1-(4-chlorobenzo[b]thiophen-2-yl)propan-1-one (1.65 g), phenyltrimethylammonium tribromide (2.76 g) and tetrahydrofuran (20 ml) was stirred under nitrogen for 18.5 hours, then it was filtered and diluted with water (200 ml). The product was extracted into dichloromethane (3×40 ml), the combined extracts were dried ($MgSO_4$) and the solvents were removed in vacuo. The residue was purified by flash chromatography over silica using dichloromethane as eluant. Appropriate fractions were combined and the solvents removed in vacuo to leave 2-bromo-1-(4-chlorobenzo[b]thiophen-2-yl)propan-1-one (3.06 g) as a pale yellow solid, m.p. 104–106° C.

A mixture of 2-bromo-1-(4-chlorobenzo[b]thiophen-2-yl)propan-1-one (0.74 g), 2-imidazolidinethione (0.19 g) and ethanol (15 ml) was heated under reflux for 20 minutes. Acetic acid (7 ml) was added and the mixture was heated under reflux for 17 hours then cooled in ice-water. The resulting solid was collected by filtration and dried in vacuo at 60° C. to give 3-(4-chlorobenzo[b]thiophen-2-yl)-2-methyl-5,6-dihydroimidazo[2,1-b]thiazole hydrobromide (0.5 g) as a white solid, m.p. 246–248° C.

Example 11

A solution of 2-bromobutyryl chloride (8 g) in dichloromethane (15 ml) was added dropwise under nitrogen at ambient temperature to a stirred suspension of anhydrous aluminium chloride (12 g) in dichloromethane (100 ml). When the addition was complete, a solution of 5-chlorobenzo[b]thiophene (5 g; prepared in a manner similar to that described in *J. Heterocyclic Chem.*, 1988, 25, 1271) in dichloromethane (30 ml) was added dropwise, then the mixture was stirred at ambient temperature for 1 hour and added to ice-cold water (500 ml). The mixture was stirred at ambient temperature for 30 minutes then the product was extracted into dichloromethane (100 ml). The extract was washed with water (2×30 ml) and saturated aqueous sodium chloride solution (2×30 ml), then it was dried ($Na_2SO_4$) and the solvent was removed in vacuo. The residue was purified by repeated (5-fold) flash chromatography over silica using a 19:1 mixture of petroleum ether (b.p. 60–80° C.) and ethyl acetate as eluant. Appropriate fractions were combined and the solvents removed in vacuo to give 2-bromo-1-(5-chlorobenzo[b]thiophen-2-yl)butan-1-one (1.04 g) as an off-white solid which was used without further purification.

A mixture of 2-bromo-1-(5-chlorobenzo[b]thiophen-2-yl)butan-1-one (1 g), 2-imidazolidinethione (0.32 g), ethanol (30 ml) and acetic acid (15 ml) was heated under reflux for 24 hours, then the solvents were removed in vacuo. The residue was crystallised from ethanol (100 ml) and the resulting solid was collected by filtration, washed with ethanol (10 ml) and dried in vacuo at 60° C. to give 3-(5-chlorobenzo[b]thiophen-2-yl)-2-ethyl-5,6-dihydroimidazo[2,1-b]thiazole hydrobromide (0.8 g) as a white solid, m.p. 282–284° C.

Example 12

Phenyltrimethylammonium tribromide (11.4 g) was added in portions under nitrogen at ambient temperature over 35 minutes to a stirred solution of 6,7-dihydrobenzo[b]thiophen-4(5H)-one (4.6 g) in tetrahydrofuran (45 ml), the mixture was stirred for 1 hour and allowed to stand at ambient temperature overnight, then it was filtered and the solvent was removed in vacuo. The residue was dissolved in dimethylformamide (20 ml), the solution was added under nitrogen to a suspension of lithium carbonate (8.2 g) in dimethylformamide (50 ml), the mixture was heated under reflux for 4 hours, then it was cooled to ambient temperature and added to 10% aqueous acetic acid solution (500 ml). The product was extracted into dichloromethane (3×100 ml) and the combined extracts were washed with water (3×100 ml), dried (MgSO$_4$), and the solvent was removed in vacuo. The residue was purified by flash chromatography over silica using dichloromethane as eluant. Appropriate fractions were combined and the solvents removed in vacuo to give benzo[b]thiophen-4-ol (4 g) as a white solid which was used without further purification.

A mixture of benzo[b]thiophen-4-ol (4 g), benzoyl chloride (3.3 ml) and pyridine (10 ml) was heated under reflux under nitrogen for 3 hours, then cooled to ambient temperature and poured onto ice-water (130 ml). The product was extracted into ether (3×50 ml), the combined extracts were washed with 5% aqueous sodium hydrogencarbonate solution (50 ml), 2M hydrochloric acid (50 ml) and water (3×50 ml), then they were dried (MgSO$_4$) and the solvent was removed in vacuo to give benzo[b]thiophen-4-yl benzoate (6.7 g) as a cream solid which was used without further purification.

A solution of acetyl chloride (0.25 ml) in dichloromethane (1.5 ml) was added dropwise under nitrogen at ambient temperature to a stirred suspension of anhydrous aluminium chloride (0.94 g) in dichloromethane (10 ml) and the mixture was stirred at ambient temperature for 15 minutes. A solution of benzo[b]thiophen-4-yl benzoate (0.6 g) in dichloromethane (4 ml) was added, the mixture was stirred at ambient temperature for 18 hours, then it was poured onto ice-water (60 ml). The product was extracted into dichloromethane (2×50 ml), the combined extracts were washed with water (50 ml), saturated aqueous sodium hydrogencarbonate solution (20 ml), water (2×50 ml) and saturated aqueous sodium chloride solution (40 ml), then they were dried (MgSO$_4$) and the solvent was removed in vacuo. The residue was purified by flash chromatography over silica using a 7:3 mixture of dichloromethane and petroleum ether (b.p. 60–80° C.) as eluant. Appropriate fractions were combined and the solvents removed in vacuo to give 2-acetylbenzo[b]thiophen-4-yl benzoate (0.13 g) as a cream solid which was used without further purification.

A mixture of 2-acetylbenzo[b]thiophen-4-yl benzoate (0.13 g), potassium carbonate (0.18 g), tetrahydrofuran (25 ml) and 5M aqueous sodium hydroxide solution (10 ml) was heated under reflux for 1 hour, then cooled to ambient temperature and concentrated in vacuo. The aqueous residue was acidified by the addition of 5M hydrochloric acid (20 ml), then the product was extracted into dichloromethane (2×25 ml). The combined extracts were washed with water (20 ml), 10% aqueous sodium hydrogencarbonate solution (3×20 ml) and water (2×20 ml), then dried (MgSO$_4$) and the solvent was removed in vacuo to give 1-(5-hydroxybenzo[b]thiophen-2-yl]ethan-1-one (0.07 g) as a yellow solid which was used without further purification.

Phenyltrimethylammonium tribromide (0.13 g) was added in portions under nitrogen at ambient temperature over 30 minutes to a stirred solution of 1-(5-hydroxybenzo[b]thiophen-2-yl]ethan-1-one (0.07 g) in tetrahydrofuran (5 ml), then the mixture was stirred at ambient temperature for 30 minutes and filtered. The solvent was removed in vacuo and the residue was dissolved in ethanol (1.5 ml). 2-Imidazolidinethione (0.036 g) and acetic acid (1 ml) were added, then the mixture was heated under reflux for 18 hours and cooled to ambient temperature. The resulting solid was collected by filtration, washed with ether (10 ml) and dried in vacuo at 60° C. to give 2-(5,6-dihydroimidazo[2,1-b]thiazol-3-yl)benzo[b]thiophen-4-ol hydrobromide (0.03 g) as a brown solid, (M$^+$=274).

Example 13

Potassium carbonate (62.4 g) was added in portions at 0° C. over 10 minutes to a stirred solution of N,O-dimethylhydroxylamine hydrochloride (250 g) in water (250 ml), then toluene (250 ml) was added and the mixture was stirred until the internal temperature reached 2° C. Butyryl chloride (26 ml) was added dropwise over 10 minutes, then the mixture was stirred at 0° C. for 5 minutes and at ambient temperature for 1 hour. The aqueous phase was separated and shaken with toluene (2×100 ml), then the combined toluene solutions were dried (Na$_2$SO$_4$) and the solvent was removed in vacuo to give N-methoxy-N-methylbutyramide (21.0 g) as a pale-yellow oil which was used without further purification.

Approximately 5 ml of a solution of 4-bromobenzo[b]thiophene (1.85 g; prepared in a manner similar to that described in *Bull. Soc. Chim. Fr.*, 1966, 111, 3667) in tetrahydrofuran (20 ml) was added under nitrogen to magnesium turnings (0.22 g) in tetrahydrofuran (2 ml). Two crystals of iodine were added, and the mixture was heated to initiate the reaction. The remainder of the 4-bromo-benzo[b]thiophene solution was added at reflux temperature over 15 minutes, then the mixture was heated under reflux 20 minutes and allowed to cool to ambient temperature. A solution of N-methoxy-N-methylbutyramide (1.13 g) in tetrahydrofuran (10 ml) was added, the mixture was heated under reflux for 50 minutes, then it was allowed to cool to ambient temperature and 2M hydrochloric acid (25 ml) was added. The mixture was stirred at ambient temperature for 1 hour, then the product was extracted into ethyl acetate (100 ml). The extract was washed with water (50 ml) and saturated aqueous sodium chloride solution (2×50 ml), dried (Na$_2$SO$_4$), and the solvents were removed in vacuo. The residue was purified by flash chromatography over silica using a 96:4 mixture of petroleum ether (b.p. 60–80° C.) and ethyl acetate as eluant. Appropriate fractions were combined and the solvents removed in vacuo to give 1-(benzo[b]thiophen-4-yl)butan-1-one (0.41 g) as a colourless oil which was used without further purification.

Phenyltrimethylammonium tribromide (0.756 g) was added in portions under nitrogen over 2 minutes to a stirred solution of 1-(benzo[b]thiophen-4-yl)butan-1-one (0.41 g) in tetrahydrofuran (15 ml), the mixture was stirred at ambient temperature for 4 hours, then it was filtered and the solvent was removed in vacuo. The residue was dissolved in ethanol (15 ml), 2-imidazolidinethione (0.205 g) was added and the mixture was heated under reflux for 10 minutes. Acetic acid (7.5 ml) was added, the mixture was heated under reflux for 65 hours, then it was allowed to cool to ambient temperature and the solvents were removed in vacuo. The residue was triturated with hot ethyl acetate (10 ml) containing a few drops of ethanol, then the resulting solid was collected by filtration and dried in vacuo to give 3-(benzo[b]thiophen-4-yl)-2-ethyl-5,6-dihydroimidazo[2,1-b]thiazole hydrobromide (0.11 g) as an off-white solid, m.p. 144–146° C.

Example 14 n-Butyllithium (2.5M solution in hexanes; 105.3 ml) was added dropwise under nitrogen at 0° C. over 30 minutes to a stirred solution of methyltriphenyl-phosphonium bromide (75.16 g) in tetrahydrofuran (250 ml), then the mixture was stirred at ambient temperature for 90 minutes. A solution of 6,7-dihydrobenzo[b]thiophen-4(5H)-one (20 g) in tetrahydrofuran (200 ml) was added, the mixture was stirred at ambient temperature for 1 hour, then it was heated under reflux for 24 hours and cooled to ambient temperature. The solvents were removed in vacuo and the residue was purified by flash chromatography over silica using a 98:2 mixture of petroleum ether (b.p. 60–80° C.) and dichloromethane as eluant. Appropriate fractions were combined and the solvents removed in vacuo to give 4-methylene-4,5,6,7-tetrahydrobenzo[b]thiophene (8.8 g) as a yellow oil which was used without further purification.

A stirred mixture of 4-methylene-4,5,6,7-tetrahydrobenzo[b]thiophene (8.8 g) 10% palladium on carbon catalyst (4.39 g) and toluene (200 ml) was heated under reflux for 6 hours, cooled to ambient temperature and filtered. The solvent was removed in vacuo to give 4-methylbenzo[b]thiophene (7.68 g) as a yellow oil which was used without further purification.

A solution of bromine (2.94 ml) in dichloromethane (30 ml) was added dropwise under nitrogen at −5° C. to a stirred mixture of 4-methylbenzo[b]thiophene (7.68 g), sodium acetate (6.38 g) and dichloromethane (100 ml). The mixture was stirred at ambient temperature for 6 hours, then it was filtered and the solvent was removed in vacuo. The residue was was distilled in vacuo to give 3-bromo-4-methylbenzo[b]thiophene (6.04 g) as a yellow oil, b.p. 100–120° C. @ 0.4 mmHg, which was used without further purification.

A solution of 3-bromo-4-methylbenzo[b]thiophene (2 g) in tetrahydrofuran (10 ml) was added dropwise under nitrogen at −70° C. over 10 minutes to a stirred solution of n-butyllithium (2.5M solution in hexanes; 4.58 ml) in ether (30 ml), then the mixture was stirred at −70° C. for 30 minutes. A solution of 2-chloro-N-methoxy-N-methylacetamide (1.04 g) in tetrahydrofuran (10 ml) was added dropwise at −70° C. over 10 minutes, then the mixture was stirred at −70° C. for 5 hours, allowed to stand at ambient temperature for 18 hours and quenched by the addition of saturated aqueous ammonium chloride solution (40 ml). The organic layer was separated, washed with saturated aqueous sodium chloride solution (40 ml), and dried (MgSO$_4$). The solvents were removed in vacuo to give 2-chloro-1-(4-methylbenzo[b]thiophen-2-yl]ethan-1-one (1.65 g) as a brown oil which was used without further purification.

A mixture of 2-chloro-1-(4-methylbenzo[b]thiophen-2-yl]ethan-1-one (0.62 g) 2-imidazolidinethione (0.28 g), acetic acid (20 ml) and ethanol (10 ml) was heated under reflux for 2 hours then cooled to ambient temperature. The solvents were removed in vacuo and the residue was crystallised from ethanol. The resulting solid was collected by filtration and dried in vacuo at 60° C. for 2 hours to give 3-(4-methylbenzo[b]thiophen-2-yl)-5,6-dihydroimidazo[2,1-b]thiazole hydrochloride (0.27 g) as colourless solid, m.p. 238–245° C.

Example 15

Potassium carbonate (90 g) was added in portions at 0° C. over 10 minutes to a stirred solution of N,O-dimethylhydroxylamine hydrochloride (36.25 g) in water (325 ml), then dichloromethane (300 ml) was added and the mixture was stirred until the internal temperature reached 5° C. Acetyl chloride (25 ml) was added dropwise over 20 minutes, then the mixture was stirred at ambient temperature for 2 hours. The organic phase was separated, washed with water (250 ml) and saturated aqueous sodium chloride solution (250 ml), then it was dried (Na$_2$SO$_4$) and the solvents were removed in vacuo to give N-methoxy-N-methylacetamide (18.26 g) as a colourless oil which was used without further purification.

n-Butyllithium (1.6 M solution in hexanes; 74.6 ml) was added dropwise under nitrogen at 0° C. to a stirred solution of benzo[b]thiophene (25.0 g) in ether (350 ml), then the mixture cooled to −70° C. and a solution of N-methoxy-N-methylacetamide (19.21 g) in ether (100 ml) was added dropwise. The mixture was stirred at ambient temperature for 18 hours, then it was poured into saturated aqueous ammonium chloride solution (400 ml). The organic phase was separated, washed with water (300 ml) and saturated aqueous sodium chloride solution (300 ml), dried (Na$_2$SO$_4$) and the solvents were removed in vacuo. The residue was triturated with petroleum ether (b.p. 60–80° C.) (50 ml) and the resulting solid was collected by filtration and dried in vacuo to give 1-(benzo[b]thiophen-2-yl]ethan-1-one (18.7 g) as a brown solid, m.p. 78–81° C.

Phenyltrimethylammonium tribromide (32.04 g) was added in portions under nitrogen at 0° C. over 10 minutes to a stirred solution of 1-(benzo[b]thiophen-2-yl]ethan-1-one (15.0 g) in tetrahydrofuran (400 ml), the mixture was stirred at ambient temperature for 5 hours, then it was filtered and the solvent was removed in vacuo. The residue was triturated with a 9:1 mixture of petroleum ether (b.p. 60–80° C.) and ethyl acetate (50 ml) and the resulting solid was collected by filtration and dried in vacuo to give 1-(benzo[b]thiophen-2-yl)-2-bromoethan-1-one (24.40 g) as a brown solid which was used without further purification.

A mixture of 1-(benzo[b]thiophen-2-yl)-2-bromoethan-1-one (21.96 g), 2-imidazolidinethione (7.81 g) and ethanol (300 ml) was heated under reflux for 10 minutes. Acetic acid (150 ml) was added, then the mixture was heated under reflux for 18 hours and allowed to cool to ambient temperature. The resulting solid was collected by filtration, washed with ethanol (50 ml) and ether (50 ml), then dried in vacuo at 100° C. for 3 hours to give 3-(benzo[b]thiophen-2-yl)-5,6-dihydroimidazo[2,1-b]thiazole hydrobromide (19.6 g) as a light brown solid, m.p. 275–285° C. (decomposes).

Sodium carbonate (9.29 g) was added at 0° C. to a stirred suspension of 3-(benzo[b]thiophen-2-yl)-5,6-dihydroimidazo[2,1-b]thiazole hydrobromide (19.0 g) in a mixture of dichloromethane (300 ml) and water (300 ml). The mixture was stirred at ambient temperature for 3 hours, then the organic phase was separated, washed with water (200 ml) and saturated aqueous sodium chloride solution (200 ml), dried (Na$_2$SO$_4$) and the solvents were removed in vacuo to give 3-(benzo[b]thiophen-2-yl)-5,6-dihydroimidazo[2,1-b]thiazole as a brown solid (13.1 g) which was used without further purification.

n-Butyllithium (1.6 M solution in hexanes; 6.25 ml) was added dropwise under nitrogen at −70° C. to a stirred solution of 3-(benzo[b]thiophen-2-yl)-5,6-dihydroimidazo[2,1-b]thiazole (2.58 g) in tetrahydrofuran (40 ml), then the mixture was stirred at −70° C. for 10 minutes and at 0° C. for 35 minutes. Dimethylformamide (0.85 ml) was added, the mixture was stirred at 0° C. for 1.5 hours, then it was poured into saturated aqueous ammonium chloride solution (200 ml). The product was extracted into ethyl acetate (2×200 ml), then the combined extracts were washed with water (2×100 ml) and saturated aqueous sodium chloride solution (2×100 ml), dried (Na$_2$SO$_4$), and the solvents were removed in vacuo. The residue was purified by flash chromatography over silica using a 19:1 mixture of ethyl acetate and methanol as eluant. Appropriate fractions were combined and the solvents were removed in vacuo to give 3-(benzo[b]thiophen-2-yl)-5,6-dihydroimidazo[2,1-b]thiazole-2-carboxaldehyde (0.73 g) as a yellow solid which was used without further purification.

Sodium borohydride (0.144 g) was added in portions over 10 minutes to a stirred suspension of 3-(benzo[b]thiophen-2-yl)-5,6-dihydroimidazo[2,1-b]-thiazole-2-carboxaldehyde (0.73 g) in methanol (20 ml), then the mixture was stirred at ambient temperature for 2 hours and allowed to stand at ambient temperature for 18 hours. Water (35 ml) was added and the mixture was stirred at ambient temperature for 10 minutes. The resulting solid was collected by filtration and dissolved in a 9:1 mixture of dichloromethane and ethanol (50 ml). The solution was dried ($Na_2SO_4$) and the solvents were removed in vacuo to give [3-(benzo[b]thiophen-2-yl)-5,6-dihydroimidazo[2,1-b]thiazol-2-yl]methanol (0.275 g) as a brown solid, m.p. 138–140° C.

Example 16

A solution of 3-bromo-4-methylbenzo[b]thiophene (1.69 g) in tetrahydrofuran (10 ml) was added dropwise under nitrogen at −70° C. over 10 minutes to a stirred solution of n-butyllithium (2.5M solution in hexanes; 3.87 ml) in ether (30 ml), then the mixture was stirred at −70° C. for 30 minutes. A solution of N-methoxy-N-methylpropionamide (1.31 g) in tetrahydrofuran (10 ml) was added dropwise at −70° C. over 10 minutes, the mixture was stirred at −70° C. for 3 hours, then it was allowed to warm to ambient temperature and quenched by the addition of saturated aqueous ammonium chloride solution (30 ml). The organic layer was separated, washed with saturated aqueous sodium chloride solution (30 ml), and dried ($MgSO_4$). The solvents were removed in vacuao to give 1-(4-methylbenzo[b]thiophen-2-yl)propan-1-one (0.53 g) as an orange solid which was used without further purification.

Phenyltrimethylammonium tribromide (1.47 g) was added in portions under nitrogen at 0° C. over 10 minutes to a stirred solution of 1-(4-methylbenzo[b]thiophen-2-yl)propan-1-one (0.53 g) in tetrahydrofuran (15 ml), then the mixture was stirred at 0° C. for 3 hours and at ambient temperature for 16 hours. Further phenyltrimethylammonium tribromide (0.49 g) was added, then the mixture was stirred at ambient temperature for 26 hours and filtered. The solvent was removed in vacuo and the residue was purified by flash chromatography over silica using a 4:1 mixture of petroleum ether (b.p. 60–80° C.) and dichloromethane as eluant. Appropriate fractions were combined and the solvents removed in vacuo to give 2-bromo-1-(4-methylbenzo[b]thiophen-2-yl)propan-1-one (0.3 g) as a yellow solid which was used without further purification.

A mixture of 2-bromo-1-(4-methylbenzo[b]thiophen-2-yl)propan-1-one (0.27 g), 2-imidazolidinethione (0.1 g), acetic acid (2 ml) and ethanol (4 ml) was heated under reflux for 3 hours, then cooled to ambient temperature. The solvents were removed in vacuo and the residue was triturated with ether (2×1 ml). The resulting solid was collected by filtration, washed with ethanol (2 ml) and dried in vacuo at 60° C. for 2 hours to give 2-methyl-3-(4-methylbenzo[b]thiophen-2-yl)-5,6-dihydroimidazo[2,1-b]thiazole hydrobromide (0.3 g) as a cream solid, m.p. 201–204° C.

Example 17

A mixture of 2-bromo-1-(4-chlorobenzo[b]thiophen-2-yl)propan-1-one (0.5 g), 3,4,5,6-tetrahydro-2-pyrimidinethiol (0.144 g) and ethanol (8 ml) was heated under reflux for 20 minutes. Acetic acid (4 ml) was added, the mixture was heated under reflux for 18 hours then the solvents were removed in vacuo. 2.5M Sulphuric acid (10 ml) was added, the mixture was heated at 95° C. for 4.5 hours, then water (30 ml) was added and the mixture was basified to pH 7 by the addition of 5M aqueous sodium hydroxide solution. The product was extracted into dichloromethane (3×25 ml), the combined extracts were dried ($MgSO_4$), and the solvent was removed in vacuo. The residue was dissolved in ethanol (20 ml) and hydrogen bromide (30% solution in acetic acid; 0.5 ml) was added. The solution was added dropwise to stirred ether (50 ml) and the resulting solid was collected by filtration and recrystallised from propan-2-ol (35 ml) to give 3-(4-chlorobenzo[b]thiophen-2-yl)-2-methyl-6,7-dihydro-5H-thiazolo[3,2-a]pyrimidine hydrobromide (0.2 g) as a white solid, m.p. 236–238° C.

Example 18

Methyl thioglycolate (11.3 ml) was added under nitrogen to a stirred solution of triethylamine (45 ml) in dimethyl sulphoxide (160 ml), then the mixture was stirred at ambient temperature for 30 minutes. A solution of 2-chloro-6-fluorobenzaldehyde (20 g) in dimethyl sulphoxide (80 ml) was added then the mixture was stirred at 95° C. for 4.66 hours, allowed to stand at ambient temperature for 18 hours and poured into water (1600 ml). The resulting solid was collected by filtration, washed with water (3×100 ml), and dried in vacuo to give methyl 4-chlorobenzo[b]thiophene-2-carboxylate (22.4 g) as an off-white solid, m.p. 84–86° C.

A mixture of methyl 4-chlorobenzo[b]thiophene-2-carboxylate (20 g), 5M aqueous sodium hydroxide solution (100 ml) and water (300 ml) was heated at 95° C. for 5 hours then poured into a mixture of concentrated hydrochloric acid (180 ml) and water (2000 ml) and stirred at ambient temperature for 2 hours. The resulting solid was collected by filtration, washed with water (3×500 ml), and dried in vacuo at 60° C. to give 4-chlorobenzo[b]thiophene-2-carboxylic acid (21.0 g) as an off-white solid, m.p. 246–248° C.

Oxalyl chloride (9.2 ml) was added dropwise at 0° C. to a stirred suspension of 4-chlorobenzo[b]thiophene-2-carboxylic acid (17.89 g) in dichloromethane (240 ml), then the mixture was allowed to warm to ambient temperature. Dimethylformamide (8 drops) was added and the mixture was stirred at ambient temperature for 4 hours. The dichloromethane was removed in vacuo and tetrahydrofuran (200 ml) and dichloromethane (50 ml) were added to the residue to give a solution. N,O-Dimethylhydroxylamine hydrochloride (9.03 g) and triethylamine (25 ml) were added and the mixture was stirred at ambient temperature for 18 hours. Water (50 ml) and triethylamine (10 ml) were added then the solution was stirred at ambient temperature for 1 hour and diluted with water (1000 ml). The product was extracted into dichloromethane (3×300 ml), the combined extracts were dried ($MgSO_4$) and the solvents were removed in vacuo. The residue was purified by flash chromatography over silica using a 19:1 mixture of dichloromethane and methanol as eluant. Appropriate fractions were combined and the solvents removed in vacuo to leave 4-chloro-N-methoxy-N-methylbenzo[b]thiophene-2-carboxamide (19.7 g) as an off-white solid which was used without further purification.

Propylmagnesium chloride (2M solution in ether; 4.3 ml) was added under nitrogen over 15 minutes to a stirred solution of 4-chloro-N-methoxy-N-methylbenzo[b]thiophene-2-carboxamide (2 g) in tetrahydrofuran (25 ml) then the mixture was stirred at ambient temperature for 2.33 hours. Further propylmagnesium chloride (2M solution in ether; 0.5 ml) was added, the mixture was stirred at ambient temperature for 0.5 hours, then water (150 ml) and 5M hydrochloric acid (15 ml) were added. The product was extracted into dichloromethane (3×40 ml), the combined extracts were dried ($MgSO_4$) and the solvents were removed in vacuo. The residue was purified by column chromatography over silica using dichloromethane as eluant. Appropriate fractions were combined and the solvents removed in vacuo to leave 1-(4-chlorobenzo[b]thiophen-2-yl)butan-1-one (0.95 g) which was used without further purification.

A mixture of 1-(4-chlorobenzo[b]thiophen-2-yl)butan-1-one (0.93 g), phenyltrimethylammonium tribromide (1.47 g) and tetrahydrofuran (20 ml) was stirred under nitrogen at ambient temperature for 66 hours, then it was filtered and diluted with water (50 ml). The product was extracted into dichloromethane (3×30 ml), the combined extracts were dried (MgSO$_4$) and the solvents were removed in vacuo. The residue was purified by flash chromatography over silica using dichloromethane as eluant. Appropriate fractions were combined and the solvents removed in vacuo to leave 2-bromo-1-(4-chlorobenzo[b]thiophen-2-yl)butan-1-one (1.07 g) which was used without further purification.

A mixture of 2-bromo-1-(4-chlorobenzo[b]thiophen-2-yl)butan-1-one (1.06 g), 2-imidazolidinethione (0.255 g) and ethanol (25 ml) was heated under reflux for 20 minutes. Acetic acid (12 ml) was added, the mixture was heated under reflux for 21 hours, then the solvents were removed in vacuo and the solid residue recrystallised from propan-2-ol (40 ml) to give 3-(4-chlorobenzo[b]thiophen-2-yl)-2-ethyl-5,6-dihydroimidazo[2,1-b]thiazole hydrobromide (0.72 g) as a white solid, m.p. 187–189° C.

Example 19 n-Butyllithium (2.5 M solution in hexanes; 4.0 ml) was added dropwise under nitrogen at −70° C. to a stirred solution of 3-(benzo[b]thiophen-2-yl)-5,6-dihydroimidazo[2,1-b]thiazole (2.58 g; prepared in a manner similar to that described in Example 15) in tetrahydrofuran (40 ml), then the mixture was stirred at −70° C. for 25 minutes. Dimethyl disulphide (0.9 ml) was added, the mixture was stirred at ambient temperature for 2 hours, then it was poured into saturated aqueous ammonium chloride solution (200 ml). The product was extracted into ethyl acetate (300 ml), then the extract was washed with water (200 ml) and saturated aqueous sodium chloride solution (2×100 ml), dried (Na$_2$SO$_4$), and the solvents were removed in vacuo. The residue was purified by flash chromatography over silica using a 19:1 mixture of ethyl acetate and methanol as eluant. Appropriate fractions were combined and the solvents removed in vacuo to give 3-(benzo[b]thiophen-2-yl)-2-(methylthio)-5,6-dihydroimidazo[2,1-b]thiazole (0.79 g) as a yellow solid, m.p. 95–97° C.

Example 20

In a similar manner to Example 18, methylthioglycolate (13 g) was reacted with 3-chloro-2-fluorobenzaldehyde (19.57 g) in dimethylformamide to give methyl 7-chlorobenzo[b]thiophene-2-carboxylate, which was hydrolysed, chlorinated and reacted with N,O-dimethylhydroxylamine hydrochloride to give 7-chloro-N-methoxy-N-methylbenzo[b]thiophene-2-carboxamide, which was reacted with ethylmagnesium bromide to give 1-(7-chlorobenzo[b]thiophen-2-yl)propan-1-one. This ketone (1.17 g) was reacted with phenyltrimethylammonium tribromide (2.15 g) to give 2-bromo-1-(7-chlorobenzo[b]thiophen-2-yl)propan-1-one (2.32 g) which was used without further purification.

A mixture of 2-bromo-1-(7-chlorobenzo[b]thiophen-2-yl)propan-1-one (2.32 g), 2-imidazolidinethione (0.53 g), ethanol (25 ml) and acetic acid (12.5 ml) was heated under reflux for 3 hours and allowed to cool to ambient temperature. The resulting solid was collected by filtration, washed with ethanol and dried in vacuo to give 3-(7-chlorobenzo[b]thiophen-2-yl)-2-methyl-5,6-dihydroimidazo[2,1-b]thiazole hydrobromide (1.12 g) as a white solid, m.p. 294–295° C.

Example 21

In a similar manner to Example 9 Method A, 1-(benzo[b]thiophen-5-yl)propan-1-one was prepared starting from methyl thioglycolate (13.2 g) and 5-bromo-2-fluorobenzaldehyde (25.35 g) which were reacted together and the product hydrolysed to give 5-bromobenzo[b]thiophene-2-carboxylic acid (30.4 g), which was decarboxylated using copper and quinoline at 190° C. for 1.5 hours to give 5-bromobenzo[b]thiophene. This compound was reacted with magnesium and then with N-methoxy-N-methylpropionamide to give 1-(benzo[b]thiophen-5-yl)propan-1-one (1.3 g) as a cream solid which was used without further purification.

Phenyltrimethylammonium tribromide (2 g) was added in portions under nitrogen at 0–5° C. to a stirred solution of 1-(benzo[b]thiophen-5-yl)propan-1-one (1 g) in tetrahydrofuran (35 ml) then the mixture was stirred at ambient temperature for 1 hour. Further phenyltrimethylammonium tribromide (0.1 g) was added, the mixture was stirred at ambient temperature for 18 hours, then it was filtered and the solvent was removed in vacuo. The residue was dissolved in ethanol (32 ml), 2-imidazolidinethione (0.54 g) was added, and the mixture was heated under reflux under nitrogen for 10 minutes. Acetic acid (17 ml) was added, the mixture was heated under reflux for 18 hours, then it was cooled to ambient temperature and the solvents were removed in vacuo. The residue was triturated with hot ethanol (10 ml) and the resulting solid was collected by filtration, washed with ethanol (10 ml) and ether (10 ml), and dried in vacuo at 60° C. to give 3-(benzo[b]thiophen-5-yl)-2-methyl-5,6-dihydroimidazo[2,1-b]thiazole hydrobromide (1.3 g) as a white solid, m.p. 285° C.

Example 22

Approximately 5 ml of a solution of 4-bromobenzo[b]thiophene (4.10 g; prepared in a manner similar to that described in *Bull. Soc. Chim. Fr.*, 1966, 111, 3667) in tetrahydrofuran (44 ml) was added under nitrogen to magnesium turnings (0.486 g). Two crystals of iodine were added and the mixture was heated to initiate the reaction. The remainder of the 4-bromobenzo[b]thiophene solution was added at reflux temperature over 20 minutes then the mixture was heated under reflux for 15 minutes and allowed to cool to ambient temperature. A solution of N-methoxy-N-methylacetamide (1.98 g; prepared in a manner similar to that described in Example 15) in tetrahydrofuran (20 ml) was added, the mixture was heated under reflux for 1 hour, then it was allowed to cool to ambient temperature. 2M Hydrochloric acid (40 ml) was added, the mixture was stirred at ambient temperature for 1 hour, then the product was extracted into ethyl acetate (250 ml). The extract was washed with water (2×50 ml) and saturated aqueous sodium chloride solution (2×50 ml), dried (Na$_2$SO$_4$), and the solvents were removed in vacuo. The residue was purified by flash chromatography over silica using a 97:3 mixture of petroleum ether (b.p. 60–80° C.) and ethyl acetate as eluant. Appropriate fractions were combined and the solvents removed in vacuo to give 1-(benzo[b]thiophen-4-yl)ethan-1-one (1.76 g) as a yellow oil which was used without further purification.

Phenyltrimethylammonium tribromide (3.75 g) was added in portions under nitrogen over 10 minutes to a stirred solution of 1-(benzo[b]thiophen-4-yl)ethan-1-one (1.76 g) in tetrahydrofuran (40 ml), the mixture was stirred for 1 hour, then it was filtered and the solvent was removed in vacuo. The residue was dissolved in ethanol (30 ml), 2-imidazolidinethione (1.02 g) was added and the mixture was heated under reflux for 10 minutes. Acetic acid (15 ml) was added, the mixture was heated under reflux for 17 hours, then it was allowed to cool to ambient temperature. The resulting solid was collected by filtration, washed with ethanol (30 ml) and ether (30 ml) and dried in vacuo at 100° C. for 3 hours to give 3-(benzo[b]thiophen-4-yl)-5,6-dihydroimidazo[2,1-b]thiazole hydrobromide (2.38 g) as a pale-yellow solid which was used without further purification.

Saturated aqueous sodium hydrogencarbonate solution (100 ml) was added at 0° C. to a stirred suspension of 3-(benzo[b]thiophen-4-yl)-5,6-dihydroimidazo[2,1-b]thiazole hydrobromide (2.38 g) in dichloromethane (50 ml), and the mixture was stirred at ambient temperature for 2 hours. The organic phase was separated, washed with water (50 ml) and saturated aqueous sodium chloride solution (50 ml), dried ($Na_2SO_4$), and the solvent was removed in vacuo to give 3-(benzo[b]thiophen-4-yl)-5,6-dihydroimidazo[2,1-b]thiazole (1.45 g) as a yellow solid which was used without further purification.

A solution of bromine (0.30 ml) in dichloromethane (15 ml) was added dropwise under nitrogen at 0–5° C. to a stirred solution of 3-(benzo[b]thiophen-4-yl)-5,6-dihydroimidazo[-2,1-b]thiazole (1.45 g) in dichloromethane (40 ml), then the mixture was stirred at ambient temperature for 1 hour. The resulting solid was collected by filtration, washed with dichloromethane (20 ml) and dried in vacuo at 40–50° C. to give 3-(benzo[b]thiophen-4-yl)-2-bromo-5,6-dihydroimidazo[2,1-b]thiazole hydrobromide (2.3 g) as a pale yellow solid, m.p. 229–235° C.

3-(Benzo[b]thiophen-4-yl)-2-bromo-5,6-dihydroimidazo[2,1-b]thiazole hydrobromide (2.3 g) was added in portions under nitrogen at 0–5° C. over 20 minutes to a stirred solution of ethylmagnesium chloride (2.0 M solution in ether; 6.9 ml) in tetrahydrofuran (35 ml), then the mixture was stirred at 0–5° C. for 20 minutes and at ambient temperature 70 minutes. The mixture was cooled to 0° C. and dimethyl disulphide (0.82 ml) was added, then the mixture was stirred at ambient temperature for 4 hours and quenched by the addition of saturated aqueous ammonium chloride solution (40 ml) and water (50 ml). The product was extracted into ethyl acetate (250 ml), then the extract was washed with saturated aqueous sodium chloride solution (2×100 ml), dried ($Na_2SO_4$), and the solvents were removed in vacuo. The residue was purified by flash chromatography over silica using a 96:4 mixture of ethyl acetate and methanol as eluant. Appropriate fractions were combined and the solvents removed in vacuo. The residue was triturated with 2M ethereal hydrogen chloride solution (20 ml) and the resulting solid was collected by filtration, washed with ether (2×20 ml) and dried in vacuo to give 3-(benzo[b]thiophen-4-yl)-2-(methylthio)-5,6-dihydroimidazo[2,1-b]thiazole hydrochloride (0.219 g) as a cream solid, m.p. 95–105° C.

Example 23

In a similar manner to Example 9 Method A, methyl 7-iodobenzo[b]thiophene-2-carboxylate (prepared in a manner similar to that described in *Tetrahedron Lett.*, 1992, 7499) was hydrolysed to give 7-iodobenzo[b]thiophene-2-carboxylic acid (10.5 g) as a colourless solid, m.p. 268–270° C., which was decarboxylated to give 7-iodobenzo[b]thiophene (6.48 g) as an oil, b.p. 90–100° C. @ 133Pa. This compound was reacted with magnesium and then with N-methoxy-N-methyl-propionamide to give 1-(benzo[b]thiophen-7-yl)propan-1-one (0.77 g) as an oil which was used without further purification.

Phenyltrimethylammonium tribromide (1.52 g) was added in portions under nitrogen at 0° C. over 30 minutes to a stirred solution of 1-(benzo[b]thiophen-7-yl)propan-1-one (0.77 g) in tetrahydrofuran (110 ml), then the mixture was stirred at ambient temperature for 18 hours. Further phenyltrimethylammonium tribromide (0.76 g) was added and the mixture was heated under reflux for 4 hours. Further phenyltrimethylammonium tribromide (0.76 g) was added, then the mixture was heated under reflux for 90 minutes, cooled to ambient temperature and filtered. The solvent was removed in vacuo and the residue was purified by flash chromatography over silica using a 7:3 mixture of petroleum ether (b.p. 60–80° C.) and dichloromethane as eluant. Appropriate fractions were combined and the solvents removed in vacuo to give 1-(benzo[b]thiophen-7-yl)-2-bromopropan-1-one (0.71 g) as an oil which was used without further purification.

A mixture of 1-(benzo[b]thiophen-7-yl)-2-bromopropan-1-one (0.83 g; prepared in a manner similar to that described above), 2-imidazolidinethione (0.32 g), ethanol (20 ml) and acetic acid (10 ml) was heated under reflux for 90 minutes then allowed to stand at ambient temperature overnight. The solvent was removed in vacuo to give a yellow oil which was triturated with ether (3×5 ml) then crystallised from ethanol. The resulting solid was suspended in acetic acid (10 ml), acetic anhydride (10 ml) was added, and the mixture was heated at 90–95° C. for 80 hours. The solvent was removed in vacuo, the residue was basified by the addition of saturated aqueous sodium hydrogencarbonate solution (25 ml), and the product was extracted into dichloromethane (60 ml). The extract was dried ($MgSO_4$) and the solvent was removed in vacuo. The residue was dissolved in warm ethanol (6 ml), concentrated hydrochloric acid (15 drops) was added and the solvent was removed in vacuo. The residue was triturated with ether (2×5 ml) and the resulting solid was collected by filtration and dried in vacuo at 60° C. to give 3-(benzo[b]thiophen-7-yl)-2-methyl-5,6-dihydroimidazo[2,1-b]thiazole hydrochloride (0.48 g) as a yellow solid, m.p. 210–212° C.

Example 24

In a similar manner to Example 18, methyl thioglycolate (9.3 ml) was reacted with 2,3-dichloro-6-fluorobenzaldehyde (15.46 g) in dimethylformamide to give methyl 4,5-dichlorobenzo[b]thiophene-2-carboxylate (7.28 g) as an off-white solid which was hydrolysed, chlorinated and reacted with N,O-dimethylhydroxylamine hydrochloride to give 4,5-dichloro-N-methoxy-N-methylbenzo[b]thiophene-2-carboxamide (1.96 g) as a colourless solid. Reaction of this amide with ethylmagnesium bromide gave 1-(4,5-dichlorobenzo[b]thiophen-2-yl)propan-1-one (1.09 g) as an oil which was used without further purification.

Phenyltrimethylammonium tribromide (1.58 g) was added in portions under nitrogen at 0° C. over 30 minutes to a stirred solution of 1-(4,5-dichlorobenzo[b]thiophen-2-yl)propan-1-one (1.09 g) in tetrahydrofuran (80 ml), then the mixture was stirred at 0° C. for 30 minutes, at ambient temperature for 18 hours and at reflux temperature for 5 hours. Further phenyltrimethylammonium tribromide (0.79 g) was added, the mixture was heated under reflux for 2 hours, then it was cooled to ambient temperature and filtered. The solvent was removed in vacuo to give a brown oil which was purified by flash chromatography over silica using a 3:1 mixture of petroleum ether (b.p. 60–80° C.) and dichloromethane as eluant. Appropriate fractions were combined and the solvents removed in vacuo to give 2-bromo-1-(4,5-dichlorobenzo[b]thiophen-2-yl)propan-1-one (1.59 g) as an oil which was used without further purification.

A mixture of 2-bromo-1-(4,5-dichlorobenzo[b]thiophen-2-yl)propan-1-one (1.59 g), 2-imidazolidinethione (0.43 g), ethanol (25 ml) and acetic acid (12.5 ml) was heated under reflux for 4 hours and allowed to cool to ambient temperature. The solvent was removed in vacuo to give a yellow solid which was triturated with ether (3×10 ml). The resulting solid was collected by filtration and dried in vacuo at 60° C. to give 3-(4,5-dichlorobenzo[b]thiophen-2-yl)-2-methyl-5,6-dihydroimidazo[2,1-b]-thiazole hydrobromide (1.8 g) as a yellow solid, m.p. 244–246° C.

Example 25

Phenyltrimethylammonium tribromide (5.36 g) was added in portions under nitrogen at 0° C. over 5 minutes to a stirred solution of 1-(benzo[b]thiophen-4-yl)butan-1-one (2.91 g; prepared in a manner similar to that described in Example 13) in tetrahydrofuran (60 ml), the mixture was stirred at ambient temperature for 4 hours, then it was filtered and the solvent was removed in vacuo. The residue was dissolved in ethanol (70 ml), 2-imidazolidinethione (1.45 g) was added and the mixture was stirred at ambient temperature for 10 minutes. Acetic acid (35 ml) was added, the mixture was heated under reflux for 17 hours, then it was allowed to cool to ambient temperature and the solvents were removed in vacuo. The residue was suspended in dichloromethane (100 ml) and basified by shaking with saturated aqueous sodium hydrogencarbonate solution (100 ml). The organic phase was separated, washed with water (30 ml), dried ($Na_2SO_4$), and the solvent was removed in vacuo. The residue was suspended in 2M sulphuric acid (50 ml), the mixture was stirred at 90–95° C. for 2 hours, then it was cooled to ambient temperature and basified by the dropwise addition of an excess of 2M aqueous sodium hydroxide solution. The product was extracted into dichloromethane (3×30 ml), then the combined extracts were washed with water (2×30 ml), dried ($Na_2SO_4$), and the solvent was removed in vacuo. The residue was purified by flash chromatography over silica using a 9:1 mixture of dichloromethane and methanol as eluant. Appropriate fractions were combined and the solvents removed in vacuo. The residue was dissolved in ethanol (30 ml), fumaric acid (0.9 g) was added, then the mixture was heated under reflux for 15 minutes and allowed to stand at ambient temperature for 18 hours. The resulting solid was collected by filtration, washed with ethanol (2×10 ml) and ether (10 ml), and dried in vacuo at 80° C. for 2 hours to give 3-(benzo[b]thiophen-4-yl)-2-ethyl-5,6-dihydroimidazo[2,1-b]thiazole fumarate (1.94 g) as an off-white solid, m.p. 171–173° C.

Example 26

A solution of N,N-dimethylthiocarbamoyl chloride (10 g) in tetrahydrofuran (40 ml) was added dropwise at <12° C. over 30 minutes to a stirred solution of 3-methoxy-2-hydroxybenzaldehyde (12.3 g) and potassium hydroxide (4.6 g) in water (105 ml) then the mixture was stirred at ambient temperature for 15 minutes. 10% Aqueous potassium hydroxide solution (30 ml) was added, then the product was extracted into toluene (3×150 ml). The combined extracts were washed with water (150 ml) then dried ($MgSO_4$). The solvents were removed in vacuo and the residue was crystallised from methanol to give 2-(N,N-dimethylthiocarbamoyloxy)-3-methoxybenzaldehyde (10.5 g) as a yellow solid which was used without further purification.

A mixture of 2-(N,N-dimethylthiocarbamoyloxy)-3-methoxybenzaldehyde (10.3 g) and diphenyl ether (200 ml) was stirred under nitrogen at 240–250° C. for 15 minutes, then it was cooled to ambient temperature and diluted with petroleum ether (b.p. 40–60° C.) (1400 ml). The mixture was allowed to stand at ambient temperature for 65 hours and at 4° C. for 24 hours, then the resulting solid was collected by filtration and dried in vacuo to give 2-(N,N-dimethylcarbamoylthio)-3-methoxybenzaldehyde (6.7 g) as pale yellow needles which were used without further purification.

A mixture of 2-(N,N-dimethylcarbamoylthio)-3-methoxybenzaldehyde (6.7 g), sodium hydroxide (1.4 g), water (13 ml) and methanol (27 ml) was heated under reflux under nitrogen for 1 hour then cooled to ambient temperature and washed with dichloromethane (20 ml). Water (10 ml), methanol (10 ml) and sodium chloroacetate (3.25 g) were added, the mixture was heated under reflux for 8 hours, then it was cooled to ambient temperature and acidified by the addition of 5M hydrochloric acid (15 ml). The product was extracted into dichloromethane (3×30 ml), then the combined extracts were dried ($MgSO_4$) and the solvent was removed in vacuo. The resulting crude (2-formyl-6-methoxyphenylthio)acetic acid (3 g) was diluted with 5M aqueous sodium hydroxide solution then the mixture was heated under reflux for 3.5 hours, cooled to ambient temperature and added dropwise to stirred 5M hydrochloric acid (150 ml). The resulting solid was collected by filtration, washed with water (40 ml) and crystallised from a 3:1 mixture of methanol and water (250 ml) to give 7-methoxybenzo[b]thiophene-2-carboxylic acid (1.9 g) as a pale pink solid which was used without further purification.

Oxalyl chloride (1 ml) was added dropwise under nitrogen at 0° C. to a stirred suspension of 7-methoxybenzo[b]thiophene-2-carboxylic acid (1.9 g) in dichloromethane (25 ml), then dimethylformamide (2 drops) was added and the mixture was stirred at ambient temperature for 4.5 hours. N,O-Dimethylhydroxylamine hydrochloride (1 g), triethylamine (3.2 ml) and dichloromethane (5 ml) were added, the mixture was stirred at ambient temperature for 19 hours, then it was poured into water (60 ml). The product was extracted into dichloromethane (2×30 ml), the combined extracts were dried ($MgSO_4$), and the solvent was removed in vacuo. The residue was purified by flash chromatography over silica using dichloromethane as eluant. Appropriate fractions were combined and the solvent removed in vacuo to give N,7-dimethoxy-N-methylbenzo[b]thiophene-2-carboxamide (1.5 g) as a gum which was used without further purification.

Ethylmagnesium bromide (1M solution in tetrahydrofuran; 6.4 ml) was added to a solution of N,7-dimethoxy-N-methylbenzo[b]thiophene-2-carboxamide (1.5 g) in tetrahydrofuran, then the mixture was stirred at ambient temperature for 1 hour and at reflux temperature for 1 hour. Further ethylmagnesium bromide (1M solution in tetrahydrofuran; 6.4 ml) was added, the mixture was stirred at ambient temperature for 1 hour and at reflux temperature for 2.5 hour, then it was cooled to ambient temperature and quenched by the addition of 5M hydrochloric acid (10 ml) and water (150 ml). The product was extracted into dichloromethane (3×60 ml), then the combined extracts were dried ($MgSO_4$) and the solvents were removed in vacuo. The residue was purified by flash chromatography over silica using dichloromethane followed by a 99:1 mixture of dichloromethane and methanol as eluants. Appropriate fractions were combined, and the solvents were removed in vacuo to give 1-(7-methoxybenzo[b]thiophen-2-yl)propan-1-one (0.7 g) as an oil which was used without further purification.

A mixture of 1-(7-methoxybenzo[b]thiophen-2-yl)propan-1-one (0.7 g), phenyltrimethylammonium tribromide (1.2 g) and tetrahydrofuran (50 ml) was stirred at ambient temperature under nitrogen for 17 hours, then it was diluted with water (150 ml). The product was extracted into dichloromethane (3×40 ml), the combined extracts were dried ($MgSO_4$) and the solvents were removed in vacuo. A mixture of the residue, 2-imidazolidinethione (0.24 g) and ethanol (25 ml) was heated under reflux for 20 minutes. Acetic acid (10 ml) was added, the mixture was heated under reflux for 19 hours, then it was cooled in ice. The resulting solid was collected by filtration, washed with ethanol (4 ml) and ether (20 ml), and dried in vacuo to give 3-(7-methoxybenzo[b]thiophen-2-yl)-2-methyl-5,6-dihydroimidazo[2,1-b]thiazole hydrobromide (0.6 g) as an off-white solid, m.p. 270–272° C.

Example 27

In a similar manner to Example 9 Method A, methyl thioglycolate (75.2 g) was reacted with 2,5-difluorobenzaldehyde (101.8 g) to give methyl 5-fluorobenzo[b]thiophene-2-carboxylate which was hydrolysed to give 5-fluorobenzo[b]thiophene-2-carboxylic acid which was decarboxylated to give 5-fluorobenzo[b]thiophene (31 g) as an orange oil which was used without further purification.

A solution of 2-bromopropionyl chloride (31 ml) in dichloromethane (130 ml) was added dropwise under nitrogen at ambient temperature over 20 minutes to a stirred suspension of freshly ground aluminium chloride (81 g) in dichloromethane (800 ml). A solution of 5-fluorobenzo[b]thiophene (31 g) in dichloromethane (300 ml) was added dropwise over 1 hour, the mixture was stirred at ambient temperature for 2.5 hours, then it was poured into ice-water (1200 ml) and stirred for 1 hour. The organic layer was separated and further product was isolated from the aqueous layer by extraction into dichloromethane (3×300 ml). The combined dichloromethane solutions were washed with water (2×400 ml) and saturated aqueous sodium chloride solution (2×400 ml), then they were dried ($Na_2SO_4$) and the solvent was removed in vacuo. The residue was purified twice by chromatography over silica using dichloromethane as eluant. Appropriate fractions were combined and the solvent removed in vacuo to give a red oil which was shown by nmr to be a mixture containing mainly 2-bromo-1-(5-fluorobenzo[b]thiophen-3-yl)propan-1-one with lower amounts of 2-bromo-1-(5-fluorobenzo[b]thiophen-2-yl) propan-1-one. The oil was further purified by Biotage radial compression flash chromatography over silica using a 10:1 mixture of petroleum ether (b.p. 40–60° C.) and ether as eluant. Appropriate fractions were combined and allowed to stand at ambient temperature. The resulting solid was collected by filtration and dried in vacuo to give 2-bromo-1-(5-fluorobenzo[b]thiophen-2-yl)propan-1-one (0.2 g) as a yellow solid which was used without further purification.

A mixture of 2-bromo-1-(5-fluorobenzo[b]thiophen-2-yl)propan-1-one (0.2 g), 2-imidazolidinethione (0.08 g) and ethanol (6 ml) was heated under reflux for 10 minutes. Acetic acid (3 ml) was added, the mixture was heated under reflux for 24 hours, then the solvents were removed in vacuo. Ethanol (10 ml) was added then removed in vacuo, and the residue was dried in vacuo at 60° C. to give 3-(5-fluorobenzo[b]thiophen-2-yl)-3-methyl-5,6-dihydroimidazo[2,1-b]thiazole hydrobromide (0.2 g) as an off-white solid, $^1$H-nmr (DMSO-$d_6$): $\delta_H$ 2.43 (3H, s, —$CH_3$), 4.22–4.51 (4H, m, —$CH_2CH_2$—), 7.36–7.44 (1H, m, ArH), 7.79 (1H, s, ArH), 7.81 (1H, dd, J 9.6 Hz, 2.5 Hz, ArH), 8.13–8.19 (1H, m ArH), 9.3–9.9 (1H, br, $H^+$).

Example 28

Approximately 1 ml of a solution of 5-bromobenzo[b]thiophene (6.6 g; prepared in a manner similar to that described in Example 21) in tetrahydrofuran (35 ml) was added under nitrogen to a mixture of magnesium turnings (0.8 g), tetrahydrofuran (7 ml) and a few small crystals of iodine, heat was applied to initiate the reaction, then the remainder of the bromobenzo[b]thiophene solution was added at reflux temperature over 20 minutes. When the addition was complete, the mixture was heated under reflux for 45 minutes, then a solution of N-methoxy-N-methylacetamide (3.8 g) in tetrahydrofuran (35 ml) was added. The mixture was heated under reflux for 30 minutes, cooled to ambient temperature, then quenched by the addition of 2M hydrochloric acid (90 ml) and stirred at ambient temperature for 30 minutes. The majority of the tetrahydrofuran was removed in vacuo, then water (150 ml) was added to the residue and the product was extracted into ethyl acetate (150 ml). The extract was washed with saturated aqueous sodium chloride solution (100 ml), dried ($MgSO_4$) and the solvent removed in vacuo. The residue was purified by flash chromatography over silica using a 95:5 mixture of petroleum ether (b.p. 60–80° C.) and ethyl acetate as eluant. Appropriate fractions were combined and the solvents removed in vacuo to give 1-(benzo[b]thiophen-5-yl)ethan-1-one (2.35 g) as a white solid which was used without further purification.

Phenyltrimethylammonium tribromide (4.8 g) was added in portions under nitrogen at 0–5° C. to a stirred solution of 1-(benzo[b]thiophen-5-yl)ethan-1-one (2.3 g) in tetrahydrofuran (80 ml), then the mixture was stirred at ambient temperature for 1 hour and allowed to stand at ambient temperature for 18 hours. Further phenyltrimethylammonium tribromide (1 g) was added and the mixture was stirred at ambient temperature for 2 hours. Further phenyltrimethylammonium tribromide (1.5 g) was added, the mixture was stirred at ambient temperature for 1.5 hours and allowed to stand at ambient temperature for 18 hours, then it was filtered and the solvent was removed in vacuo. The residue was dissolved in ethanol (72 ml), 2-imidazolidinethione (1.3 g) was added, and the mixture was heated under reflux for 10 minutes. Acetic acid (39 ml) was added, the mixture was heated under reflux for 18 hours, then it was cooled to ambient temperature. The resulting solid was collected by filtration and dried in vacuo to give 3-(benzo[b]thiophen-5-yl)-5;6-dihydroimidazo[2,1-b]thiazole hydrobromide (2.6 g) as a yellow solid which was used without further purification. Further product was isolated from the ethanolic filtrate by concentration in vacuo and trituration of the residue with ethanol. The resulting gummy solid was collected by filtration and triturated with hot ethanol. The resulting solid was collected by filtration, washed with ethanol and ether, and dried in vacuo to give 3-(benzo[b]thiophen-5-yl)-5,6-dihydroimidazo[2,1-b]thiazole hydrobromide (2.3 g) as a yellow solid which was used without further purification.

Saturated aqueous sodium hydrogencarbonate solution (100 ml) was added over 10 minutes to a stirred suspension of 3-(benzo[b]thiophen-5-yl)-5,6-dihydroimidazo[2,1-b]thiazole hydrobromide (2.6 g) in dichloromethane (100 ml), the mixture was stirred at ambient temperature for 45 minutes, then the organic layer was separated, washed with water (2×75 ml) and saturated aqueous sodium chloride solution (75 ml), dried ($MgSO_4$) and the solvent was removed in vacuo to give 3-(benzo[b]thiophen-5-yl)-5,6-dihydroimidazo[2,1-b]thiazole (1.9 g) as an orange solid which was used without further purification.

A solution of bromine (0.4 ml) in dichloromethane (5 ml) was added dropwise under nitrogen to a stirred suspension of 3-(benzo[b]thiophen-5-yl)-5,6-dihydroimidazo[2,1-b]thiazole (1.9 g) in dichloromethane (20 ml), then the mixture was stirred at ambient temperature for 30 minutes. The resulting solid was collected by filtration and dried in vacuo at ambient temperature to give 3-(benzo[b]thiophen-5-yl)-2-bromo-5,6-dihydroimidazo[2,1-b]thiazole hydrobromide (1.9 g) as a yellow solid which was used without further purification. Concentration of the filtrate yielded a second crop of 3-(benzo[b]thiophen-5-yl)-2-bromo-5,6-dihydroimidazo[2,1-b]thiazole hydrobromide (0.4 g) as a yellow solid.

3-(Benzo[b]thiophen-5-yl)-2-bromo-5,6-dihydroimidazo[2,1-b]thiazole hydrobromide (1.9 g) was added in portions under nitrogen at 0–5° C. to a stirred solution of ethylmagnesium chloride (2M solution in ether; 6.8 ml) in tetrahydrofuran (30 ml), then the mixture was stirred at this temperature for 20 minutes. Dimethylformamide (1.5 ml) was added at <15° C., the mixture was stirred at <15° C. for 20 minutes and at ambient temperature for 1 hour, then it was quenched by the addition of saturated aqueous ammonium chloride solution (10 ml) and water (5 ml). Ethyl acetate (30 ml) was added, the mixture was stirred at ambient temperature for 18 hours, then the organic layer was separated and further product was isolated from the aqueous layer by extraction into ethyl acetate (2×15 ml). The combined ethyl acetate solutions were washed with water (2×30 ml) and saturated aqueous sodium chloride solution (35 ml), then they were dried (MgSO$_4$) and the solvents were removed in vacuo. The residue was purified by flash chromatography over silica using a 9:1 mixture of ethyl acetate and methanol as eluant. Appropriate fractions were combined and the solvents were removed in vacuo to give 3-(benzo[b]thiophen-5-yl)-5,6-dihydroimidazo[2,1-b]thiazole-2-carboxaldehyde (0.7 g) as a yellow solid, m.p. 146° C.

Sodium borohydride (0.13 g) was added in portions at 0–5° C. to a stirred suspension of 3-(benzo[b]thiophen-5-yl)-5,6-dihydroimidazo[2,1-b]thiazole-2-carboxaldehyde (0.67 g) in methanol (20 ml), then the mixture was stirred at this temperature for 45 minutes and at ambient temperature for 1.5 hours. Water (10 ml) was added dropwise, the mixture was stirred at ambient temperature for 1 hour, and the resulting solid was collected by filtration and washed with water. The solid was dissolved in ethanol, the solvent was removed in vacuo, and the residue was triturated with dichloromethane 10 ml). The resulting solid was collected by filtration and dried in vacuo to give [3-(benzo[b]thiophen-5-yl)-5,6-dihydroimidazo[2,1-b]-thiazol-2-yl]methanol (0.1 g) as a pale yellow solid, m.p. 149–150° C.

Example 29

A few drops of a solution of 5-bromobenzo[b]thiophene (2 g; prepared in a manner similar to that described in Example 21) in tetrahydrofuran (10 ml) was added under nitrogen to a mixture of magnesium turnings (0.24 g), tetrahydrofuran (2 ml) and a few small crystals of iodine, heat was applied to initiate the reaction, then the remainder of the bromobenzo[b]thiophene solution was added at reflux temperature over 10 minutes. When the addition was complete, the mixture was heated under reflux for 1 hour, then a solution of N-methoxy-N,3-dimethylbutyramide (1.43 g) in tetrahydrofuran (10 ml) was added. The mixture was heated under reflux for 1 hour, cooled to ambient temperature, then quenched by the addition of 2M hydrochloric acid (25 ml) and stirred at ambient temperature for 5 minutes. The majority of the tetrahydrofuran was removed in vacuo, then water (25 ml) was added to the residue and the product was extracted into ethyl acetate (2×25 ml). The extracts were washed with water (25 ml) and saturated aqueous sodium chloride solution (25 ml), dried (MgSO$_4$) and the solvent removed in vacuo. The residue was purified by flash chromatography over silica using petroleum ether (b.p. 60–80° C.) followed by a 95:5 mixture of petroleum ether (b.p. 60–80° C.) and ethyl acetate as eluants. Appropriate fractions were combined and the solvents removed in vacuo to give 1-(benzo[b]thiophen-5-yl)-3-methylbutan-1-one (1.25 g) as an off-white solid which was used without further purification.

Phenyltrimethylammonium tribromide (2.16 g) was added in portions under nitrogen at 0–5° C. to a stirred solution of 1-(benzo[b]thiophen-5-yl)-3-methylbutan-1-one (1.25 g) in tetrahydrofuran (40 ml), the mixture was stirred at ambient temperature for 1.25 hours, then it was filtered and the solvent was removed in vacuo. The residue was dissolved in ethanol (40 ml), 2-imidazolidinethione (0.6 g) was added and the mixture was heated under reflux for 10 minutes. Acetic acid (22 ml) was added, the mixture was heated under reflux for 18 hours, allowed to cool to ambient temperature, then it was filtered and the solvents were removed in vacuo. The residue was suspended in dichloromethane (40 ml), water (50 ml) and sodium hydrogencarbonate (1.1 g) were added, and the mixture was stirred at ambient temperature for 15 minutes. The organic layer was separated and further product was isolated from the aqueous layer by extraction into dichloromethane (20 ml). The combined dichloromethane solutions were dried (MgSO$_4$) and the solvent was removed in vacuo. The residue was purified by flash chromatography over silica using a 95:5 mixture of dichloromethane and methanol as eluant. Appropriate fractions were combined and the solvents were removed in vacuo to give a yellow oil (0.26 g). A sample (30 mg) of the oil was purified by preparative-scale hplc on a 100 mm×21.2 mm C18 BDS Hypersil column using gradient elution with acetonitrile:water (30:70)→100% acetonitrile over 3 minutes and 100% acetonitrile thereafter. Appropriate fractions were combined and the solvents removed in vacuo to leave 3-(benzo[b]thiophen-5-yl)-2-(1-methylethyl)-5,6-dihydroimidazo[2,1-b]-thiazole (9 mg) as an orange solid, $^1$H-nmr (DMSO-d$_6$): $\delta_H$1.24 (3H, d, J 6.8 Hz, 2×—CH$_3$), 3.07 (1H, m, —CH(CH$_3$)$_2$), 4.25–4.44 (4H, m, —CH$_2$CH$_2$—), 7.31 (1H, dd, J 8.3 Hz, 1.5 Hz, ArH), 7.44 (1H, d, J 5.3 Hz, ArH), 7.62 (1H, d, J 5.4 Hz, ArH), 7.85 (1H, fine d, ArH), 8.03 (1H, d, J 8.3 Hz, ArH).

Example 30

3-(Benzo[b]thiophen-5-yl)-2-bromo-5,6-dihydroimidazo[2,1-b]thiazole hydrobromide (0.4 g; prepared as described in Example 28) was added in portions under nitrogen at 0–5° C. over 8 minutes to a stirred solution of ethylmagnesium chloride (2M solution in ether; 1.4 ml) in tetrahydrofuran (10 ml), then the mixture was stirred at 0° C. for 20 minutes and at ambient temperature for 1.25 hours. Dimethyl disulphide (0.14 ml) was added at 0–5° C., the mixture was stirred at this temperature for 10 minutes and at ambient temperature for 4.5 hours, then it was quenched by the addition of saturated aqueous ammonium chloride solution (10 ml) and water (20 ml). The product was extracted into ethyl acetate (30 ml+2×25 ml), the combined extracts were washed with water (2×25 ml) and saturated aqueous sodium chloride solution (25 ml), then they were dried (MgSO$_4$) and the solvents were removed in vacuo. The residue was purified by flash chromatography over silica using a 9:1 mixture of ethyl acetate and methanol as eluant. Appropriate fractions were combined and the solvents were removed in vacuo to give 3-(benzo[b]thiophen-5-yl)-2-(methylthio)-5,6-dihydroimidazo[2,1-b]thiazole (2 mg) as a yellow solid, ¹H-nmr (DMSO-d₆): $\delta_H$ 2.25 (3H, s, —SCH₃), 3.68–4.19 (4H, m, —CH₂CH₂—), 7.36 (1H, d, J 1.7 Hz, ArH), 7.39–7.41 (1H, m, ArH), 7.54 (1H, d, J 5.45 Hz, ArH), 7.87 (1H, d, J 1.4 Hz, ArH), 7.96 (1H, d, J 8.3 Hz, ArH).

Example 31

A few drops of a solution of 5-bromobenzo[b]thiophene (0.93 g; prepared in a manner similar to that described in Example 21) in tetrahydrofuran (10 ml) was added under nitrogen to a mixture of magnesium turnings (0.1 g), tetrahydrofuran (2 ml) and a few small crystals of iodine, heat was applied to initiate the reaction, then the remainder of the bromobenzo[b]thiophene solution was added at reflux temperature over 10 minutes. When the addition was complete, the mixture was heated under reflux for 45 minutes, then a solution of N-methoxy-N-methylbutyramide (0.6 g) in tetrahydrofuran (10 ml) was added. The mixture was heated under reflux for 1 hour, cooled to ambient temperature, then quenched by the addition of 2M hydrochloric acid (15 ml). Ethyl acetate (25 ml) was added, the mixture was stirred at ambient temperature for 45 minutes, the organic layer was separated, then further product was isolated from the aqueous layer by extraction into ethyl acetate (20 ml). The combined ethyl acetate solutions were washed with water (2×10 ml) and saturated aqueous sodium chloride solution (10 ml), then they were dried (MgSO₄) and the solvents were removed in vacuo. The residue was purified by flash chromatography over silica using petroleum ether (b.p. 60–80° C.) followed by a 95:5 mixture of petroleum ether (b.p. 60–80° C.) and ethyl acetate as eluants. Appropriate fractions were combined and the solvents removed in vacuo to give 1-(benzo[b]thiophen-5-yl)butan-1-one (0.1 g) as a yellow oil which was used without further purification.

Phenyltrimethylammonium tribromide (0.18 g) was added in portions under nitrogen at 0–5° C. to a stirred solution of 1-(benzo[b]thiophen-5-yl)butan-1-one (0.1 g) in tetrahydrofuran (20 ml), the mixture was stirred at ambient temperature for 2 hours, then it was filtered and the solvent was removed in vacuo. The residue was dissolved in ethanol (15 ml), 2-imidazolidinethione (0.05 g) was added, and the mixture was heated under reflux for 10 minutes. Acetic acid (2 ml) was added, the mixture was heated under reflux for 65 hours, then it was cooled to ambient temperature and the solvents were removed in vacuo. The residue was suspended in dichloromethane (25 ml), water (25 ml) and sodium hydrogencarbonate (0.1 g) were added, and the mixture was stirred at ambient temperature for 1 hour. The organic layer was separated and further product was isolated from the aqueous layer by extraction into dichloromethane (20 ml). The combined dichloromethane solutions were washed with water (2×20 ml) and saturated aqueous sodium chloride solution (20 ml), then they were dried (MgSO₄) and the solvent was removed in vacuo. The residue was dissolved in ethanol (10 ml), fumaric acid (0.07 g) was added, the mixture was heated under reflux for 10 minutes, then it was allowed to stand at 4° C. for 18 hours. No solid precipitated, so the solvent was removed in vacuo. The residue was triturated with cold ether (7 ml), the resulting solid was collected by filtration, then it was suspended in ether (3 ml) and the mixture was heated under reflux for 2 minutes. Ethanol (2 ml) was added, the mixture was heated under reflux for 2 minutes, then it was cooled to ambient temperature. The resulting solid was collected by filtration and dried in vacuo to give 3-(benzo[b]thiophen-5-yl)-2-ethyl-5,6-dihydroimidazo[2,1-b]thiazole fumarate (50 mg) as an off-white solid, m.p. 145–150° C.

Example 32

3-(Benzo[b]thiophen-4-yl)-2-bromo-5,6-dihydroimidazo[2,1-b]thiazole hydrobromide (15 g; prepared in a manner similar to that described in Example 22) was added in portions under nitrogen at 0–5° C. over 20 minutes to a stirred solution of ethylmagnesium chloride (2M solution in ether; 45 ml) in tetrahydrofuran (225 ml), then the mixture was stirred at 0–5° C. for 2 hours. The mixture was cooled to 0° C. and dimethyl disulphide (5.4 ml) was added, then the mixture was stirred at ambient temperature for 18 hours and quenched by the addition of saturated aqueous ammonium chloride solution (150 ml). The majority of the tetrahydrofuran was removed in vacuo, the residue was diluted with water (200 ml) and the product was extracted into ethyl acetate (400 ml). The extract was washed with water (300 ml) and saturated aqueous sodium chloride solution (2×150 ml), then it was dried (Na₂SO₄), and the solvents were removed in vacuo. The residue was purified by Biotage flash chromatography over silica using a 96:4 mixture of ethyl acetate and methanol as eluant. Appropriate fractions were combined and the solvents removed in vacuo to leave 3-(benzo[b]thiophen-4-yl)-2-(methylthio)-5,6-dihydroimidazo[2,1-b]thiazole (7.3 g) as a pale yellow solid, m.p. 104–107° C.

A mixture of 3-(benzo[b]thiophen-4-yl)-2-(methylthio)-5,6-dihydroimidazo[2,1-b]thiazole (5.5 g), fumaric acid (2.1 g) and methanol (32 ml) was heated under reflux for 5 minutes then stirred at ambient temperature for 25 minutes. The resulting solid was collected by filtration, washed with ice-cold methanol (10 ml) and dried in vacuo at 95° C. for 2.5 hours to give 3-(benzo[b]thiophen-4-yl)-2-(methylthio)-5,6-dihydroimidazo[2,1-b]thiazole fumarate (6.4 g) as a colourless solid, m.p. 185–187° C.

Example 33

A mixture of 3-(benzo[b]thiophen-4-yl)-2-methyl-5,6-dihydroimidazo[2,1-b]thiazole hydrochloride (2 g; prepared in a manner similar to that described in Example 9 Method A), 5M aqueous sodium hydrogencarbonate solution (50 ml) and dichloromethane (50 ml) was stirred at ambient temperature for 30 minutes, then the free base was extracted into dichloromethane (2×50 ml). The combined extracts were dried (MgSO₄) and the solvent was removed in vacuo. The residue was dissolved in tetrahydrofuran (40 ml), then the stirred solution was cooled to −70° C. and n-butyllithium (2.5M solution in hexanes; 2.85 ml) was added dropwise under nitrogen. The mixture was stirred at −70° C. for 1 hour, then methyl iodide (0.45 ml) was added dropwise. The mixture was stirred at −70° C. for 1 hour then it was poured into saturated aqueous ammonium chloride solution (50 ml). The product was extracted into ethyl acetate (2×50 ml), the combined extracts were dried (MgSO₄) and the solvents were removed in vacuo. The residue was purified via flash chromatography over silica using a 9:1 mixture of dichloromethane and methanol as eluant. Appropriate fractions were combined and the solvents were removed in vacuo. The residue was dissolved in ethanol, concentrated hydrochloric acid (10 drops) was added, the solvent was removed in vacuo, and the residue was triturated with ether (30 ml). The mixture was allowed to stand at ambient temperature for 72 hours then the resulting solid was collected by filtration and dried in vacuo to give 2-methyl-3-(2-methylbenzo[b]thiophen-4-yl)-5,6-dihydroimidazo[2,1-b]thiazole hydrochloride (1.15 g) as a colourless solid, m.p. 271° C.

Example 34

Oxalyl chloride (9.6 ml) was added dropwise at 0° C. under nitrogen to a stirred solution of cyclopropaneacetic acid (10 g) in dichloromethane (250 ml), then the mixture was stirred at 0° C. for 1 hour and at ambient temperature for 42 hours. The resulting solution of cyclopropaneacetyl chloride was added dropwise at 0–5° C. to a stirred aqueous solution of N,O-dimethylhydroxylamine prepared by addition of potassium carbonate (24.8 g) in portions at 0–5° C. over 30 minutes to a stirred solution of N,O-dimethylhydroxylamine hydrochloride (10.2 g) in water (110 ml). When the addition of the acid chloride solution was complete, the mixture was stirred at 0° C. for 20 minutes and at ambient temperature for 4 hours. The organic phase was separated, washed with saturated aqueous sodium chloride solution (50 ml) and dried (MgSO$_4$), then the solvent was removed in vacuo to leave N-methoxy-N-methylcyclopropaneacetamide (13.6 g) as a colourless oil which was used without further purification.

A few drops of a solution of 4-bromobenzo[b]thiophene (2.84 g; prepared in a manner similar to that described in Example 9 Method A) in tetrahydrofuran (20 ml) was added under nitrogen to magnesium turnings (0.4 g). Two crystals of iodine were added and heat was applied to initiate the reaction. The remainder of the 4-bromobenzo[b]thiophene solution was added at reflux temperature over 20 minutes, then the mixture was heated under reflux for 2 hours. A solution of N-methoxy-N-methylcyclopropaneacetamide (2.0 g) in tetrahydrofuran (10 ml) was added, the mixture was heated under reflux for 2.5 hours, then it was stirred at ambient temperature for 18 hours and quenched by the addition of 2M hydrochloric acid (40 ml). The mixture was stirred at ambient temperature for 1 hour, then the product was extracted into ethyl acetate (3×30 ml). The combined extracts were washed with water (30 ml) and saturated aqueous sodium chloride solution (20 ml), dried (MgSO$_4$), and the solvents were removed in vacuo. The residue was purified by flash chromatography over silica using petroleum ether (b.p. 60–80° C.) followed by a 95:5 mixture of petroleum ether (b.p. 60–80° C.) and ethyl acetate as eluants. Appropriate fractions were combined and the solvents removed in vacuo to give 1-(benzo[b]thiophen-4-yl)-2-cyclopropylethan-1-one (1.2 g) as a colourless oil which was used without further purification.

A mixture of phenyltrimethylammonium tribromide (2.2 g), 1-(benzo[b]thiophen-4-yl)-2-cyclopropylethan-1-one (1.2 g) and tetrahydrofuran (40 ml) was stirred at ambient temperature under nitrogen for 18 hours, then it was filtered and diluted with water (50 ml). The product was extracted into dichloromethane (2×30 ml), the combined extracts were dried (MgSO$_4$) and the solvents were removed in vacuo. The residue was dissolved in ethanol (30 ml), 2-imidazolidinethione (0.6 g) was added, and the mixture was heated under reflux for 45 minutes. Acetic acid (12 ml) was added, the mixture was heated under reflux for 18 hours, then it was allowed to cool to ambient temperature and the solvents were removed in vacuo. The residue was dissolved in a mixture of ethanol (15 ml) and ether (5 ml), the solution was cooled in ice and the resulting solid was collected by filtration, washed with ethanol (20 ml) and ether (100 ml) and dried in vacuo to give 3-(benzo[b]thiophen-4-yl)-2-cyclopropyl-5,6-dihydroimidazo[2,1-b]thiazole hydrobromide (1.3 g) as a white solid, m.p. 213–214° C.

Example 35

Approximately 5 ml of a solution of 4-bromobenzo[b]thiophene (2.87 g; prepared in a manner similar to that described in Example 9 Method A) in tetrahydrofuran (30 ml) was added under nitrogen to magnesium turnings (0.45 g). Two crystals of iodine were added and heat was applied to initiate the reaction. The remainder of the 4-bromobenzo[b]thiophene solution was added at reflux temperature over 20 minutes, then the mixture was heated under reflux for a further 15 minutes. A solution of N-methoxy-N,3-dimethylpropionamide (2.12 g) in tetrahydrofuran (15 ml) was added, the mixture was heated under reflux for 30 minutes, then it was cooled to ambient temperature and quenched by the addition of 2M hydrochloric acid (30 ml). The mixture was stirred at ambient temperature for 1.5 hours, then the product was extracted into ethyl acetate (150 ml). The combined extracts were washed with water (2×100 ml) and saturated aqueous sodium chloride solution (200 ml), dried (MgSO$_4$), and the solvents were removed in vacuo. The residue was purified by Biotage flash chromatography over silica using a 97:3 mixture of petroleum ether (b.p. 60–80° C.) and ethyl acetate as eluant. Appropriate fractions were combined and the solvents removed in vacuo to give 1-(benzo[b]thiophen-4-yl)-3-methylpropan-1-one (1.7 g) as a colourless oil which was used without further purification.

Phenyltrimethylammonium tribromide (2.9 g) was added in portions under nitrogen at 0–5° C. to a stirred solution of 1-(benzo[b]thiophen-4-yl)-3-methylpropan-1-one (1.7 g) in tetrahydrofuran (35 ml), the mixture was stirred at ambient temperature for 3 hours, then it was filtered and the solvent was removed in vacuo. The residue was dissolved in ethanol (37 ml), 2-imidazolidinethione (0.8 g) was added and the mixture was heated under reflux for 15 minutes. Acetic acid (18 ml) was added, the mixture was heated under reflux for 20 hours, then it was filtered and the solvents were removed in vacuo. The residue was dissolved in dichloromethane (50 ml), saturated aqueous sodium hydrogencarbonate solution (50 ml) was added, and the mixture was stirred at ambient temperature for 20 minutes. The organic phase was separated, washed with water (50 ml) and saturated aqueous sodium chloride solution (50 ml), dried (Na$_2$SO$_4$), and the solvent was removed in vacuo. The residue was purified by Biotage flash chromatography over silica using a 9:1 mixture of ethyl acetate and methanol as eluant. Appropriate fractions were combined and the solvents were removed in vacuo. The residue was dissolved in ethanol (3 ml), fumaric acid (0.125 g) was added, then the mixture was heated briefly to reflux temperature then allowed to cool to ambient temperature over 4 hours. The resulting solid was collected by filtration, washed with a few drops of cold ethanol and ether, then dried in vacuo to give 3-(benzo[b]thiophen-4-yl)-2-(1-methylethyl)-5,6-dihydroimidazo[2,1-b]thiazole fumarate (0.064 g) as a white solid, m.p. 175–178° C.

Example 36

Oxalyl chloride (25 g) was added dropwise at 0° C. under nitrogen to a stirred solution of pent-4-enoic acid (19 ml) in dichloromethane (400 ml), then the mixture was stirred at 0° C. for 45 minutes and at ambient temperature for 45 hours. The resulting solution of pent-4-enoyl chloride was added dropwise at 0–5° C. over 1.25 hours to a stirred aqueous solution of N,O-dimethylhydroxylamine prepared by addition of potassium carbonate (46.6 g) in portions at 0–5° C. over 30 minutes to a stirred solution of N,O-dimethylhydroxylamine hydrochloride (19.2 g) in water (200 ml). When the addition of the acid chloride solution was complete, the mixture was stirred at 0° C. for 30 minutes and at ambient temperature for 5 hours, then it was allowed to stand at ambient temperature for 65 hours. The organic phase was separated, washed with water (200 ml) and saturated aqueous sodium chloride solution (200 ml) and dried (MgSO$_4$), then the solvent was removed in vacuo to leave N-methoxy-N-methylpent-4-enamide (30.7 g) as a colourless oil which was used without further purification.

A few drops of a solution of 4-bromobenzo[b]thiophene (5 g; prepared in a manner similar to that described in Example 9 Method A) in tetrahydrofuran (10 ml) was added under nitrogen to magnesium turnings (0.6 g). Two crystals of iodine were added and heat was applied to initiate the reaction. The remainder of the 4-bromobenzo[b]thiophene solution was added at reflux temperature over 30 minutes, the mixture was heated under reflux for 2 hours, then further tetrahydrofuran (10 ml) was added. A solution of N-methoxy-N-methylpent-4-enamide (5 g) in tetrahydrofuran (5 ml) was added, the mixture was heated under reflux for 3 hours, then it was cooled to ambient temperature and quenched by the addition of water (100 ml) and 5M hydrochloric acid (5 ml). The product was extracted into ethyl acetate (3×60 ml), the combined extracts were washed with water (100 ml) and saturated aqueous sodium chloride solution (100 ml), then they were dried ($MgSO_4$), and the solvents were removed in vacuo. The residue was purified by flash chromatography over silica using 99:1 followed by a 98:2 mixtures of petroleum ether (b.p. 40–60° C.) and ethyl acetate as eluants. Appropriate fractions were combined and the solvents removed in vacuo to give 1-(benzo[b]thiophen-4-yl)pent-4-en-1-one (1.6 g) as a colourless oil which was used without further purification.

A mixture of phenyltrimethylammonium tribromide (2.6 g), 1-(benzo[b]thiophen-4-yl)pent-4-en-1-one (1.5 g) and tetrahydrofuran (25 ml) was stirred at ambient temperature under nitrogen for 24 hours, then it was filtered. The filter cake was washed with dichloromethane (3×20 ml), then the combined filtrate and washings were washed with water (40 ml), dried ($MgSO_4$) and the solvents were removed in vacuo. The residue was dissolved in ethanol (40 ml), 2-imidazolidinethione (0.4 g) was added, and the mixture was heated under reflux for 20 minutes. Acetic acid (20 ml) was added, the mixture was heated under reflux for 47 hours, then it was allowed to cool to ambient temperature and the solvents were removed in vacuo. The residue was purified by flash chromatography over silica using 19:1 followed by 9:1 mixtures of dichloromethane and methanol as eluants. Appropriate fractions were combined and the solvents were removed in vacuo. The residue was triturated with propan-2-ol (5 ml) and the resulting solid was collected by filtration and dried in vacuo to give 2-allyl-3-(benzo[b]thiophen-4-yl)-5,6-dihydroimidazo[2,1-b]thiazole hydrobromide (0.143 g) as a white solid, m.p. 188–190° C.

Example 37

In a similar manner to Example 9 Method A, 1-(benzo[b]thiophen-6-yl)propan-1-one was prepared starting from methyl thioglycolate (17.8 ml) and 4-bromo-2-fluorobenzaldehyde (40 g) which were reacted together to give methyl 6-bromobenzo[b]thiophene-2-carboxylate (55 g), m.p. 108–110° C. This ester was hydrolysed to give 6-bromobenzo[b]thiophene-2-carboxylic acid (48 g), which was decarboxylated using copper and quinoline at 180–200° C. for 2 hours to give 6-bromobenzo[b]thiophene (20.3 g), m.p. 53–55° C. This compound (7.5 g) was reacted with magnesium (0.9 g) and then with N-methoxy-N-methylpropionamide (6.1 g) to give 1-(benzo[b]thiophen-6-yl)propan-1-one (3.6 g) as a pale yellow solid which was used without further purification.

Phenyltrimethylammonium tribromide (7.8 g) was added in portions under nitrogen at 0–5° C. to a stirred solution of 1-(benzo[b]thiophen-6-yl)propan-1-one (3.6 g) in tetrahydrofuran (100 ml), the mixture was stirred at 0° C. for 30 minutes and at ambient temperature for 30 minutes, then it was filtered through a short column of silica. The product was eluted using a 4:1 mixture of petroleum ether (b.p. 40–60° C.) and dichloromethane followed by dichloromethane as eluants. Appropriate fractions were combined and the solvents were removed in vacuo. The residue was dissolved in ethanol (20 ml), 2-imidazolidinethione (2.24 g) and acetic acid (10 ml) were added, the mixture was heated under reflux for 3 hours, then it was cooled to 0° C. The resulting solid was collected by filtration, washed with ethanol (10 ml) and dried in vacuo at 60° C. for 2 hours to give 3-(benzo[b]thiophen-6-yl)-2-methyl-5,6-dihydroimidazo[2,1-b]thiazole hydrobromide (5.5 g) as a white solid, m.p. 252–254° C.

Example 38

In a similar manner to Example 9 Method A, 1-(7-fluorobenzo[b]thiophen-4-yl)propan-1-one was prepared starting from 4-bromo-1,2-difluorobenzene (39.7 g). This was lithiated and reacted with dimethylformamide to give 6-bromo-2,3-difluorobenzaldehyde (41.3 g) as a yellow solid. The aldehyde was reacted with methyl thioglycolate (14.6 ml) to give methyl 4-bromo-7-fluorobenzo[b]thiophene-2-carboxylate (31.2 g) as a yellow solid. The ester was hydrolysed to give 4-bromo-7-fluorobenzo[b]thiophene-2-carboxylic acid (37.25 g) as a yellow solid which was decarboxylated using copper and quinoline at 170–180° C. for 4 hours to give 4-bromo-7-fluorobenzo[b]thiophene (18.2 g) as a white solid, m.p. 47–48° C. This compound (7.4 g) was reacted with magnesium (0.85 g) and then with N-methoxy-N-methylpropionamide (5.6 g) to give 1-(7-fluorobenzo[b]thiophen-4-yl)propan-1-one (2.1 g) as an oil which was used without further purification.

Phenyltrimethylammonium tribromide (4.1 g) was added in portions under nitrogen at 0–5° C. to a stirred solution of 1-(7-fluorobenzo[b]thiophen-4-yl)propan-1-one (2.1 g) in tetrahydrofuran (50 ml), the mixture was stirred at 0° C. for 25 minutes and at ambient temperature for 1 hour, then it was filtered through a short column of silica. The product was eluted using petroleum ether (b.p. 40–60° C.) followed by dichloromethane as eluants. Appropriate fractions were combined and the solvents were removed in vacuo. The residue was dissolved in ethanol (10 ml), 2-imidazolidinethione (1 g) and acetic acid (5 ml) were added, the mixture was heated under reflux for 3 hours, then it was allowed to stand at 4° C. for 18 hours. No solid precipitated, so the solvents were removed in vacuo and the residue was triturated with ether (3×30 ml). The residue remaining after decantation of the ethereal solutions was crystallised from ethanol, and the resulting solid was collected by filtration and dried in vacuo to give 3-(7-fluorobenzo[b]thiophen-4-yl)-2-methyl-5,6-dihydroimidazo[2,1-b]thiazole hydrobromide (2 g) as a white solid, m.p. 265–267° C.

Example 39 n-Butyllithium (2.5M solution in hexanes: 3.9 ml) was added dropwise under nitrogen at 0–5° C. to a stirred suspension of methyltriphenylphosphonium bromide (3.4 g) in tetrahydrofuran (35 ml), then the mixture was stirred at 0–5° C. for 15 minutes and at ambient temperature for 30 minutes. 3-(Benzo[b]thiophen-4-yl)-5,6-dihydroimidazo[2,1-b]thiazole-2-carboxaldehyde (2.5 g; prepared in a manner similar to that described in Example 3) was added, the mixture was stirred at ambient temperature for 30 minutes and at reflux temperature for 3 hours, then it was cooled to ambient temperature and quenched by the addition of water (80 ml). The product was extracted into dichloromethane (3×40 ml), the combined extracts were washed with saturated aqueous sodium chloride solution (40 ml), then they were dried (MgSO₄) and the solvents were removed in vacuo. The residue was purified by flash chromatography over silica using a 19:1 mixture of dichloromethane and methanol as eluant. Appropriate fractions were combined and the solvents were removed in vacuo. The residue was dissolved in ethanol (1 ml), concentrated hydrochloric acid (3 drops) was added and the mixture was diluted with ether (30 ml). The resulting solid was collected by filtration and dried in vacuo to give 3-(benzo[b]thiophen-4-yl)-2-vinyl-5, 6-dihydroimidazo[2,1-b]thiazole hydrochloride (0.045 g) as a white solid, m.p. 195–197° C.

Pharmaceutical Examples

Example A

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose are de-aggregated and blended. The mixture is filled into hard gelatin capsules, each capsule containing a unit dose or part of a unit dose of active compound.

b) Tablets

Tablets are prepared from the following ingredients.

| | Parts by weight |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinyl-pyrrolidone in ethanol. The dry granulate is blended with the magnesium stearate and the rest of the starch. The mixture is then compressed in a tableting machine to give tablets each containing a unit dose or a part of a unit dose of active compound.

c) Enteric Coated Tablets

Tablets are prepared by the method described in (b) above. The tablets are enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound is incorporated in 1300 parts by weight of triglyceride suppository base and the mixture formed into suppositories each containing a therapeutically effective amount of active ingredient.

We claim:
1. A compound of Formula I

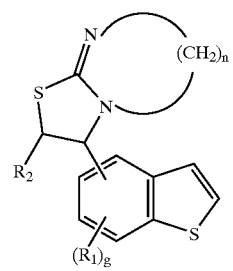

I including pharmaceutically acceptable salts thereof in which g is 0, 1, 2, 3, 4 or 5;

n is 2;

$R_1$ is a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; $R_1$ being the same or different when g is 2, 3, 4 or 5;

$R_2$ represents H, an alkyl group containing 1 to 6 carbon atoms optionally substituted by one or more halo, a hydroxyalkyl group containing 1 to 6 carbon atoms, an α-hydroxyarylmethyl group, a hydroxyalkenyl group containing 3 to 6 carbon atoms in which hydroxy is not attached directly to either carbon of the double bond, a hydroxyalkynyl group containing 3 to 6 carbon atoms in which hydroxy is not attached directly to either carbon of the triple bond, a hydroxycycloalkyl group containing 3 to 6 carbon atoms, an alkenyl group containing 2 to 8 carbon atoms, an arylalkenyl group containing 8 to 10 carbon atoms, a cycloalkyl group containing 3 to 6 carbon atoms, a $C_{3-4}$alkynylalkoxy$C_{1-3}$alkyl group, a $C_{4-6}$cycloalkylalkoxy$C_{1-3}$alkyl group, a $C_{1-3}$alkoxy$C_{1-3}$alkyl group, a $C_{1-3}$alkylthio$C_{1-3}$alkyl group, a $C_{1-3}$alkoxy group, a $C_{1-3}$alkylthio group, an arylthio group, a $C_{1-6}$alkanoyl group, a $C_{3-6}$alkoxycarbonylalkyl group, cyano, halo, a $C_{1-4}$alkylaminomethyl group, a $C_{1-4}$alkylaminoalkyl group or a hydroxyiminomethyl group; and wherein the condensed thiazole ring may be attached at the 2, 4, 5, 6 or 7-position of the benzothiophene ring with the proviso that when the condensed thiazole ring is attached at the 2-position or the 5-position of the benzothiophene ring and g is 0 then $R_2$ is not H, and with the further proviso that when the condensed thiazole ring is attached at the 2-position of the benzothiophene ring and g is other than 0 then $R_1$ is not attached at the 3-position of the benzothiophene ring.

2. A compound of Formula I according to claim 1 in which g is 0, 1 or 2;

$R_1$ is halo, an alkyl group containing 1 to 3 carbon atoms, an alkoxy group containing 1 to 3 carbon atoms or hydroxy; and $R_2$ represents H, an alkyl group containing 1 to 3 carbon atoms, a hydroxyalkyl group containing 1 to 6 carbon atoms, a $C_{1-3}$alkylthio group, a cycloalkyl group containing 3 to 6 carbon atoms, or an alkenyl group containing 2 to 8 carbon atoms.

3. A compound of Formula I according to claim 1 in which g is 0, 1 or 2;

$R_1$ is halo, an alkyl group containing 1 to 3 carbon atoms, an alkoxy group containing 1 to 3 carbon atoms or hydroxy; and $R_2$ represents H, an alkyl group containing 1 to 3 carbon atoms, a hydroxyalkyl group containing 1 to 6 carbon atoms or a $C_{1-3}$alkylthio group.

4. A compound of Formula I according to claim 1 as represented by Formula II

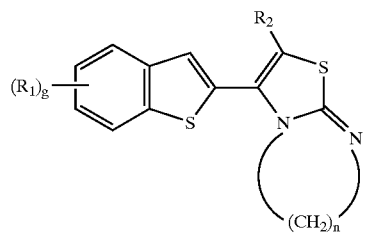

II in which $R_1$, $R_2$, n and r are as initially defined.

5. A compound of Formula I according to claim 1 as represented by Formula III

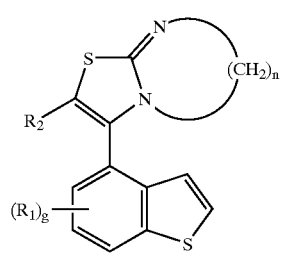

III in which $R_1$, $R_2$, n and g are as initially defined.

6. A compound of Formula I according to claim 1 as represented by Formula IV

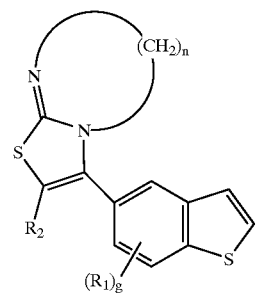

IV in which $R_1$, $R_2$, n and g are as initially defined.

7. A compound of Formula I according to claim 1 as represented by Formula V

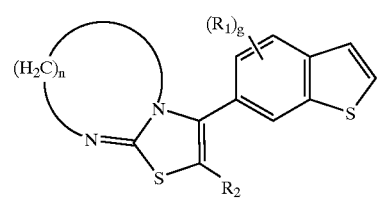

V in which $R_1$, $R_2$, n and g are as initially defined.

8. A compound of Formula I according to claim 1 as represented by Formula VI

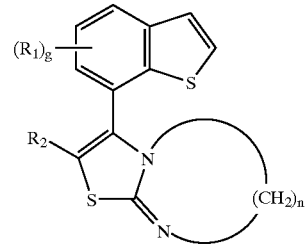

VI in which $R_1$, $R_2$, n and g are as initially defined.

9. A compound according to any one of claim 4 in which g is 0, 1 or 2;

$R_1$ is halo, an alkyl group containing 1 to 3 carbon atoms, an alkoxy group containing 1 to 3 carbon atoms or hydroxy; and $R_2$ represents H, an alkyl group containing 1 to 3 carbon atoms, a hydroxyalkyl group containing 1 to 6 carbon atoms, a $C_{1-3}$alkylthio group, a cycloalkyl group containing 3 to 6 carbon atoms, or an alkenyl group containing 2 to 8 carbon atoms.

10. A compound according to any one of claim 4 in which g is 0, 1 or 2;

$R_1$ is halo, an alkyl group containing 1 to 3 carbon atoms, an alkoxy group containing 1 to 3 carbon atoms or hydroxy; and $R_2$ represents H, an alkyl group containing 1 to 3 carbon atoms, a hydroxyalkyl group containing 1 to 6 carbon atoms or a $C_{1-3}$alkylthio group.

11. A compound according to claim 4 in which g is 0, 1 or 2;

$R_1$ is fluoro, chloro, hydroxy, methyl or methoxy, with the proviso that, when g is other than 0, $R_1$ is not attached at the 3-position of the benzo[b]thiophene ring; and R$_2$ represents H, methyl, ethyl, hydroxymethyl or methylthio, with the proviso that, when g is 0, R$_2$ is not H.

12. A compound according to claim 5 in which g is 0 or 1;
R$_1$ is fluoro or methyl; and
R$_2$ represents H, an alkyl group containing 1 to 3 carbon atoms, a hydroxyalkyl group containing 1 to 6 carbon atoms a C$_{1-3}$alkylthio group, a cycloalkyl group containing 3 to 6 carbon atoms, or an alkenyl group containing 2 to 8 carbon atoms.

13. A compound according to claim 5 in which g is 0 or 1;
R$_1$ is fluoro or methyl; and
R$_2$ represents H, an alkyl group containing 1 to 3 carbon atoms, a hydroxyalkyl group containing 1 to 6 carbon atoms or a C$_{1-3}$alkylthio group.

14. A compound according to claim 6 in which g is 0, and R$_2$ represents an alkyl group containing 1 to 3 carbon atoms, a hydroxyalkyl group containing 1 to 6 carbon atoms or a C$_{1-3}$alkylthio group.

15. A compound according to claim 7 in which g is 0, and R$_2$ represents H, an alkyl group containing 1 to 3 carbon atoms, a hydroxyalkyl group containing 1 to 6 carbon atoms, or a C$_{1-3}$alkylthio group.

16. A compound according to claim 8 in which g is 0, and R$_2$ represents H, an alkyl group containing 1 to 3 carbon atoms, a hydroxyalkyl group containing 1 to 6 carbon atoms, or a C$_{1-3}$alkylthio group.

17. A compound of Formula I according to claim 1 selected from:

3-(4-chlorobenzo[b]thiophen-2-yl)-5,6-dihydroimidazo[2,1-b]thiazole;

3-(benzo[b]thiophen-4-yl)-5,6-dihydroimidazo[2,1-b]thiazole;

[3-(benzo[b]thiophen-4-yl)-5,6-dihydroimidazo[2,1-b]thiazol-2-yl]methanol;

[3-(4-chlorobenzo[b]thiophen-2-yl]-5,6-dihydroimidazo[2,1-b]thiazol-2-yl]methanol;

3-(4-fluorobenzo[b]thiophen-2-yl)-5,6-dihydroimidazo[2,1-b]thiazole;

3-(benzo[b]thiophen-2-yl)-2-methyl-5,6-dihydroimidazo[2,1-b]thiazole;

3-(4-fluorobenzo[b]thiophen-2-yl)-2-methyl-5,6-dihydroimidazo[2,1-b]thiazole;

3-(benzo[b]thiophen-4-yl)-2-methyl-5,6-dihydroimidazo[2,1-b]thiazole;

3-(4-chlorobenzo[b]thiophen-2-yl)-2-methyl-5,6-dihydroimidazo[2,1-b]thiazole;

3-(5-chorobenzo[b]thiophen-2-yl)-2-ethyl-5,6-dihydroimidazo[2,1-b]thiazole;

2-(5,6-dihydroimidazo[2,1-b]thiazol-3-yl)benzo[b]thiophen-4-ol;

3-(benzo[b]thiophen-4-yl)-2-ethyl-5,6-dihydroimidazo[2,1-b]thiazole;

3-(4-methylbenzo[b]thiophen-2-yl)-5,6-dihyroimidazo[2,1-b]thiazole;

[3-(benzo[b]thiophen-2-yl)-5,6-dihydroimidazo[2,1-b]thiazol-2-yl]methanol;

2-methyl-3-(4-methylbenzo[b]thiophen-2-yl)-5,6-dihydroimidazo[2,1-b]thiazole;

3-(4-chlorobenzo[b]thiophen-2-yl)-2-methyl-6,7-dihyro-5H-thiazolo[3,2-a]pyrimidine;

3-(4-chlorobenzo[b]thiophen-2-yl)-2-ethyl-5,6-dihydroimidazo[2,1-b]thiazole;

3-(benzo[b]thiophen-2-yl)-2-(methylthio)-5,6-dihydroimidazo[2,1-b]thiazole;

3-(7-chlorobenzo[b]thiophen-2-yl-2-methyl)-5,6-dihydroimidazo[2,1-b]thiazole;

3-(benzo[b]thiophen-5-yl)-2-methyl-5,6-dihydroimidazo[2,1-b]thiazole;

3-(benzo[b]thiophen-4-yl)-2-(methylthio)-5,6-dihydroimidazo[2,1-b]thiazole;

3-(benzo[b]thiophen-7-yl)-2-methyl-5,6-dihydroimidazo[2,1-b]thiazole;

3-(4,5-dichlorobenzo[b]thiophen-2-yl)-2-methyl-5,6-dihydroimidazo[2,1-b]thiazole;

3-(7-methoxybenzo[b]thiophen-2-yl)-2-methyl-5,6-dihydroimidazo[2,1-b]thiazole;

3-(5-fluorobenzo[b]thiophen-2-yl)-2-methyl-5,6-dihydroimidazo[2,1-b]thiazole;

[3-(benzo[b]thiophen-5-yl)-5,6-dihydroimidazo[2,1-b]thiazol-2-yl]methanol;

3-(benzo[b]thiophen-5-yl)-2-(1-methylethyl)-5,6-dihydroimidazo[2,1-b]thiazole;

3-(benzo[b]thiophen-5-yl)-2-(methylthio)-5,6-dihydroimidazo[2,1-b]thiazole;

3-(benzo[b]thiophen-5-yl)-2-ethyl-5,6-dihydroimidazo[2,1-b]thiazole;

3-(benzo[b]thiophen-4-yl)-2-cyclopropyl-5,6-dihydroimidazo[2,1-b]thiazole;

2-methyl-3-(2-methylbenzo[b]thiophen-4-yl)-5,6-dihydroimidazo[2,1-b]thizole;

3-(benzo[b]thiophen-4-yl)-2-(1-methylethyl)-5,6-dihydroimidazo[2,1-b]thiazole;

2-allyl-3-(benzo[b]thiophen-4-yl)-5,6-dihydroimidazo[2,1-b]thiazole;

3-(benzo[b]thiophen-6-yl)-2-methyl-5,6-dihydroimidazo[2,1-b]thiazole;

3-(7-fluorobenzo[b]thiophen-4-yl)-2-methyl-5,6-dihydroimidazo[2,1-b]thiazole;

3-(benzo[b]thiophen-4-yl)-2-vinyl-5,6-dihydroimidazo[2,1-b]thiazole;

3-(benzo[b]thiophen-2-yl)-2-ethyl-5,6-dihydroimidazo[2,1-b]thiazole;

3-(benzo[b]thiophen-2-yl)-2-propyl-5,6-dihydroimidazo[2,1-b]thiazole;

3-(benzo[b]thiophen-2-yl)-2-(1-methylethyl)-5,6-dihydroimidazo[2,1-b]thiazole;

3-(benzo[b]thiophen-2-yl)-2-cyclopropyl-5,6-dihydroimidazo[2,1-b]thiazole;

3-(benzo[b]thiophen-2-yl)-2-vinyl-5,6-dihydroimidazo[2,1-b]thiazole;

3-(benzo[b]thiophen-2-yl)-2-methoxymethyl-5,6-dihydroimidazo[2,1-b]thiazole;

1-[3-(benzo[b]thiophen-2-yl)-5,6-dihydroimidazo[2,1-b]thiazol-2-yl]ethanol;

2-[3-(benzo[b]thiophen-2-yl)-5,6-dihydroimidazo[2,1-b]thiazol-2-yl]ethanol;

3-(4-chlorobenzo[b]thiophen-2-yl)-2-propyl-5,6-dihydroimidazo[2,1-b]thiazole;

3-(4-chlorobenzo[b]thiophen-2-yl)-2-(1-methylethyl)-5,6-dihydroimidazo[2,1-b]thiazole;

3-(4-chlorobenzo[b]thiophen-2-yl)-2-cyclopropyl-5,6-dihydroimidazo[2,1-b]thiazole;

3-(4-chlorobenzo[b]thiophen-2-yl)-2-vinyl-5,6-dihydroimidazo[2,1-b]thiazole;

3-(4-chlorobenzo[b]thiophen-2-y)-2-(methylthio)-5,6-dihydroimidazo[2,1-b]thiazole;

1-[3-(4-chlorobenzo[b]thiophen-2-yl)-5,6-dihydroimidazo[2,1-b]thiazol-2-yl]ethanol;

2-[3-(4-chlorobenzo[b]thiophen-2-yl)-5,6-dihydroimidazo[2,1-b]thiazol-2-yl]ethanol;

3-(5-chlorobenzo[b]thiophen-2-yl)-2-methyl-5,6-dihydroimidazo[2,1-b]thiazole;

3-(5-chlorobenzo[b]thiophen-2-yl)-2-propyl-5,6-dihydroimidazo[2,1-b]thiazole;

3-(5-chlorobenzo[b]thiophen-2-yl)-2-(1-methylethyl)-5,6-dihydroimidazo[2,1-b]thiazole;

3-(5-chlorobenzo[b]thiophen-2-yl)-2-cyclopropyl-5,6-dihydroimidazo[2,1-b]thiazole;

3-(5-chlorobenzo[b]thiophen-2-yl)-2-vinyl-5,6-dihydroimidazo[2,1-b]thiazole;

3-(5-chlorobenzo[b]thiophen-2-yl)-2-(methylthio)-5,6-dihydroimidazo[2,1-b]thiazole;

[3-(5-chlorobenzo[b]thiophen-2-yl)-5,6-dihydroimidazo[2,1-b]thiazol-2-yl]methanol;

1-[3-(5-chlorobenzo[b]thiophen-2-yl)-5,6-dihydroimidazo[2,1-b]thiazol-2-yl]ethanol;

2-[3-(5-chlorobenzo[b]thiophen-2-yl)-5,6-dihydroimidazo[2,1-b]thiazol-2-yl]ethanol;

3-(6-chlorobenzo[b]thiophen-2-yl)-2-methyl-5,6-dihydroimidazo[2,1-b]thiazole;

3-(6-chlorobenzo[b]thiophen-2-yl)-2-ethyl-5,6-dihydroimidazo[2,1-b]thiazole;

3-(6-chlorobenzo[b]thiophen-2-yl)-2-propyl-5,6-dihydroimidazo[2,1-b]thiazole;

3-(6-chlorobenzo[b]thiophen-2-yl)-2-(1-methylethyl)-5,6-dihydroimidazo[2,1-b]thiazole;

3-(6-chlorobenzo[b]thiophen-2-yl)-2-cyclopropyl-5,6-dihydroimidazo[2,1-b]thiazole;

3-(6-chlorobenzo[b]thiophen-2-yl)-2-vinyl-5,6-dihydroimidazo[2,1-b]thiazole;

3-(6-chlorobenzo[b]thiophen-2-yl)-2-(methylthio)-5,6-dihydroimidazo[2,1-b]thiazole;

[3-(6-chlorobenzo[b]thiophen-2-yl)-5,6-dihydroimidazo[2,1-b]thiazol-2-yl]methanol;

1-[3-(6-chlorobenzo[b]thiophen-2-yl)-5,6-dihydroimidazo[2,1-b]thiazol-2-yl]ethanol;

2-[3-(6-chlorobenzo[b]thiophen-2-yl)-5,6-dihydroimidazo[2,1-b]thiazol-2-yl]ethanol;

3-(7-chlorobenzo[b]thiophen-2-yl)-2-ethyl-5,6-dihydroimidazo[2,1-b]thiazole;

3-(7-chlorobenzo[b]thiophen-2-yl)-2-propyl-5,6-dihydroimidazo[2,1-b]thiazole;

3-(7-chlorobenzo[b]thiophen-2-yl)-2-(1-methylethyl)-5,6-dihydroimidazo[2,1-b]thiazole;

3-(7-chlorobenzo[b]thiophen-2-yl)-2-cyclopropyl-5,6-dihydroimidazo[2,1-b]thiazole;

3-(7-chlorobenzo[b]thiophen-2-yl)-2-vinyl-5,6-dihydroimidazo[2,1-b]thiazole;

3-(7-chlorobenzo[b]thiophen-2-yl)-2-(methylthio)-5,6-dihydroimidazo[2,1-b]thiazole;

[3-(7-chlorobenzo[b]thiophen-2-yl)-5,6-dihydroimidazo[2,1-b]thiazol-2-yl]methanol;

1-[3-(7-chlorobenzo[b]thiophen-2-yl)-5,6-dihydroimidazo[2,1-b]thiazol-2-yl]ethanol;

2-[3-(7-chlorobenzo[b]thiophen-2-yl)-5,6-dihydroimidazo[2,1-b]thiazol-2-yl]ethanol;

3-(4-fluorobenzo[b]thiophen-2-yl)-2-ethyl-5,6-dihydroimidazo[2,1-b]thiazole;

3-(4-fluorobenzo[b]thiophen-2-yl)-2-propyl-5,6-dihydroimidazo[2,1-b]thiazole;

3-(4-fluorobenzo[b]thiophen-2-yl)-2-(1-methylethyl)-5,6-dihydroimidazo[2,1-b]thiazole;

3-(4-fluorobenzo[b]thiophen-2-yl)-2-cyclopropyl-5,6-dihydroimidazo[2,1-b]thiazole;

3-(4-fluorobenzo[b]thiophen-2-yl)-2-vinyl-5,6-dihydroimidazo[2,1-b]thiazole;

3-(4-fluorobenzo[b]thiophen-2-yl)-2-methoxymethyl-5,6-dihydroimidazo[2,1-b]thiazole;

3-(4-fluorobenzo[b]thiophen-2-yl)-2-(methylthio)-5,6-dihydroimidazo[2,1-b]thiazole;

1-[3-(4-fluorobenzo[b]thiophen-2-yl)-5,6-dihydroimidazo[2,1-b]thiazol-2-yl]ethanol;

2-[3-(4-fluorobenzo[b]thiophen-2-yl)-5,6-dihydroimidazo[2,1-b]thiazol-2-yl]ethanol;

3-(5-fluorobenzo[b]thiophen-2-yl)-2-ethyl-5,6-dihydroimidazo[2,1-b]thiazole;

3-(5-fluorobenzo[b]thiophen-2-yl)-2-propyl-5,6-dihydroimidazo[2,1-b]thiazole;

3-(5-fluorobenzo[b]thiophen-2-yl)-2-(1-methylethyl)-5,6-dihydroimidazo[2,1-b]thiazole;

3-(5-fluorobenzo[b]thiophen-2-yl)-2-cyclopropyl-5,6-dihydroimidazo[2,1-b]thiazole;

3-(5-fluorobenzo[b]thiophen-2-yl)-2-vinyl-5,6-dihydroimidazo[2,1-b]thiazole;

3-(5-fluorobenzo[b]thiophen-2-yl)-2-(methylthio)-5,6-dihydroimidazo[2,1-b]thiazole;

[3-(5-fluorobenzo[b]thiophen-2-yl)-5,6-dihydroimidazo[2,1-b]thiazol-2-yl]methanol;

1-[3-(5-fluorobenzo[b]thiophen-2-yl)-5,6-dihydroimidazo[2,1-b]thiazol-2-yl]ethanol;

2-[3-(5-fluorobenzo[b]thiophen-2-yl)-5,6-dihydroimidazo[2,1-b]thiazol-2-yl]ethanol;

3-(6-fluorobenzo[b]thiophen-2-yl)-2-methyl-5,6-dihydroimidazo[2,1-b]thiazole;

3-(6-fluorobenzo[b]thiophen-2-yl)-2-ethyl-5,6-dihydroimidazo[2,1-b]thiazole;

3-(6-fluorobenzo[b]thiophen-2-yl)-2-propyl-5,6-dihydroimidazo[2,1-b]thiazole;

3-(6-fluorobenzo[b]thiophen-2-yl)-2-(1-methylethyl)-5,6-dihydroimidazo[2,1-b]thiazole;

3-(6-fluorobenzo[b]thiophen-2-yl)-2-cyclopropyl-5,6-dihydroimidazo[2,1-b]thiazole;

3-(6-fluorobenzo[b]thiophen-2-yl)-2-vinyl-5,6-dihydroimidazo[2,1-b]thiazole;

3-(6-fluorobenzo[b]thiophen-2-yl)-2-(methylthio)-5,6-dihydroimidazo[2,1-b]thiazole;

[3-(6-fluorobenzo[b]thiophen-2-yl)-5,6-dihydroimidazo[2,1-b]thiazol-2-yl]methanol;

1-[3-(6-fluorobenzo[b]thiophen-2-yl)-5,6-dihydroimidazo[2,1-b]thiazol-2-yl]ethanol;

2-[3-(6-fluorobenzo[b]thiophen-2-yl)-5,6-dihydroimidazo[2,1-b]thiazol-2-yl]ethanol;

3-(7-fluorobenzo[b]thiophen-2-yl)-2-methyl-5,6-dihydroimidazo[2,1-b]thiazole;

3-(7-fluorobenzo[b]thiophen-2-yl)-2-ethyl-5,6-dihydroimidazo[2,1-b]thiazole;

3-(7-fluorobenzo[b]thiophen-2-yl)-2-propyl-5,6-dihydroimidazo[2,1-b]thiazole;

3-(7-fluorobenzo[b]thiophen-2-yl)-2-(1-methylethyl)-5,6-dihydroimidazo[2,1-b]thiazole;

3-(7-fluorobenzo[b]thiophen-2-yl)-2-cyclopropyl-5,6-dihydroimidazo[2,1-b]thiazole;

3-(7-fluorobenzo[b]thiophen-2-yl)-2-vinyl-5,6-dihydroimidazo[2,1-b]thiazole;

3-(7-fluorobenzo[b]thiophen-2-yl)-2-(methylthio)-5,6-dihydroimidazo[2,1-b]thiazole;

[3-(7-fluorobenzo[b]thiophen-2-yl)-5,6-dihydroimidazo[2,1-b]thiazol-2-yl]methanol;

1-[3-(7-fluorobenzo[b]thiophen-2-yl)-5,6-dihydroimidazo[2,1-b]thiazol-2-yl]ethanol;

2-[3-(7-fluorobenzo[b]thiophen-2-yl)-5,6-dihydroimidazo[2,1-b]thiazol-2-yl]ethanol;

3-(4-methoxybenzo[b]thiophen-2-yl)-2-methyl-5,6-dihydroimidazo[2,1-b]thiazole;

2-ethyl-3-(4-methoxybenzo[b]thiophen-2-yl)-5,6-dihydroimidazo[2,1-b]thiazole;

3-(4-methoxybenzo[b]thiophen-2-yl)-2-propyl-5,6-dihydroimidazo[2,1-b]thiazole;

3-(4-methoxybenzo[b]thiophen-2-yl)-2-(1-methylethyl)-5,6-dihydroimidazo[2,1-b]thiazole;

2-cyclopropyl-3-(4-methoxybenzo[b]thiophen-2-yl)-5,6-dihydroimidazo[2,1-b]thiazole;

3-(4-methoxybenzo[b]thiophen-2-yl)-2-vinyl-5,6-dihydroimidazo[2,1-b]thiazole;

3-(4-methoxybenzo[b]thiophen-2-yl)-2-(methylthio)-5,6-dihydroimidazo[2,1-b]thiazole;

[3-(4-methoxybenzo[b]thiophen-2-yl)-5,6-dihydroimidazo[2,1-b]thiazol-2-yl]methanol;

1-[3-(4-methoxybenzo[b]thiophen-2-yl)-5,6-dihydroimidazo[2,1-b]thiazol-2-yl]ethanol;

2-[3-(4-methoxybenzo[b]thiophen-2-yl)-5,6-dihydroimidazo[2,1-b]thiazol-2-yl]ethanol;

3-(5-methoxybenzo[b]thiophen-2-yl)-2-methyl-5,6-dihydroimidazo[2,1-b]thiazole;

2-ethyl-3-(5-methoxybenzo[b]thiophen-2-yl)-5,6-dihydroimidazo[2,1-b]thiazole;

3-(5-methoxybenzo[b]thiophen-2-yl)-2-propyl-5,6-dihydroimidazo[2,1-b]thiazole;

3-(5-methoxybenzo[b]thiophen-2-yl)-2-(1-methylethyl)-5,6-dihydroimidazo[2,1-b]thiazole;

2-cyclopropyl-3-(5-methoxybenzo[b]thiophen-2-yl)-5,6-dihydroimidazo[2,1-b]thiazole;

3-(5-methoxybenzo[b]thiophen-2-yl)-2-vinyl-5,6-dihydroimidazo[2,1-b]thiazole;

3-(5-methoxybenzo[b]thiophen-2-yl)-2-(methylthio)-5,6-dihydroimidazo[2,1-b]thiazole;

[3-(5-methoxybenzo[b]thiophen-2-yl)-5,6-dihydroimidazo[2,1-b]thiazol-2-yl]methanol;

1-[3-(5-methoxybenzo[b]thiophen-2-yl)-5,6-dihydroimidazo[2,1-b]thiazol-2-yl]ethanol;

2-[3-(5-methoxybenzo[b]thiophen-2-yl)-5,6-dihydroimidazo[2,1-b]thiazol-2-yl]ethanol;

3-(6-methoxybenzo[b]thiophen-2-yl)-2-methyl-5,6-dihydroimidazo[2,1-b]thiazole;

2-ethyl-3-(6-methoxybenzo[b]thiophen-2-yl)-5,6-dihydroimidazo[2,1-b]thiazole;

3-(6-methoxybenzo[b]thiophen-2-yl)-2-propyl-5,6-dihydroimidazo[2,1-b]thiazole;

3-(6-methoxybenzo[b]thiophen-2-yl)-2-(1-methylethyl)-5,6-dihydroimidazo[2,1-b]thiazole;

2-cyclopropyl-3-(6-methoxybenzo[b]thiophen-2-yl)-5,6-dihydroimidazo[2,1-b]thiazole;

3-(6-methoxybenzo[b]thiophen-2-yl)-2-vinyl-5,6-dihydroimidazo[2,1-b]thiazole;

3-(6-methoxybenzo[b]thiophen-2-yl)-2-(methylthio)-5,6-dihydroimidazo[2,1-b]thiazole;

[3-(6-methoxybenzo[b]thiophen-2-yl)-5,6-dihydroimidazo[2,1-b]thiazol-2-yl]methanol;

1-[3-(6-methoxybenzo[b]thiophen-2-yl)-5,6-dihydroimidazo[2,1-b]thiazol-2-yl]ethanol;

2-[3-(6-methoxybenzo[b]thiophen-2-yl)-5,6-dihydroimidazo[2,1-b]thiazol-2-yl]ethanol;

2-ethyl-3-(7-methoxybenzo[b]thiophen-2-yl)-5,6-dihydroimidazo[2,1-b]thiazole;

3-(7-methoxybenzo[b]thiophen-2-yl)-2-propyl-5,6-dihydroimidazo[2,1-b]thiazole;

3-(7-methoxybenzo[b]thiophen-2-yl)-2-(1-methylethyl)-5,6-dihydroimidazo[2,1-b]thiazole;

2-cyclopropyl-3-(7-methoxybenzo[b]thiophen-2-yl)-5,6-dihydroimidazo[2,1-b]thiazole;

3-(7-methoxybenzo[b]thiophen-2-yl)-2-vinyl-5,6-dihydroimidazo[2,1-b]thiazole;

3-(7-methoxybenzo[b]thiophen-2-yl)-2-(methylthio)-5,6-dihydroimidazo[2,1-b]thiazole;

[3-(7-methoxybenzo[b]thiophen-2-yl)-5,6-dihydroimidazo[2,1-b]thiazol-2-yl]methanol;

1-[3-(7-methoxybenzo[b]thiophen-2-yl)-5,6-dihydroimidazo[2,1-b]thiazol-2-yl]ethanol;

2-[3-(7-methoxybenzo[b]thiophen-2-yl)-5,6-dihydroimidazo[2,1-b]thiazol-2-yl]ethanol;

2-ethyl-3-(4-methylbenzo[b]thiophen-2-yl)-5,6-dihydroimidazo[2,1-b]thiazole;

3-(4-methylbenzo[b]thiophen-2-yl)-2-propyl-5,6-dihydroimidazo[2,1-b]thiazole;

3-(4-methylbenzo[b]thiophen-2-yl)-2-(1-methylethyl)-5,6-dihydroimidazo[2,1-b]thiazole;

2-cyclopropyl-3-(4-methylbenzo[b]thiophen-2-yl)-5,6-dihydroimidazo[2,1-b]thiazole;

3-(4-methylbenzo[b]thiophen-2-yl)-2-vinyl-5,6-dihydroimidazo[2,1-b]thiazole;

3-(4-methylbenzo[b]thiophen-2-yl)-2-(methylthio)-5,6-dihydroimidazo[2,1-b]thiazole;

[3-(4-methylbenzo[b]thiophen-2-yl)-5,6-dihydroimidazo[2,1-b]thiazol-2-yl]methanol;

1-[3-(4-methylbenzo[b]thiophen-2-yl)-5,6-dihydroimidazo[2,1-b]thiazol-2-yl]ethanol;

2-[3-(4-methylbenzo[b]thiophen-2-yl)-5,6-dihydroimidazo[2,1-b]thiazol-2-yl]ethanol;

2-methyl-3-(5-methylbenzo[b]thiophen-2-yl)-5,6-dihydroimidazo[2,1-b]thiazole;

2-ethyl-3-(5-methylbenzo[b]thiophen-2-yl)-5,6-dihydroimidazo[2,1-b]thiazole;

3-(5-methylbenzo[b]thiophen-2-yl)-2-propyl-5,6-dihydroimidazo[2,1-b]thiazole;

3-(5-methylbenzo[b]thiophen-2-yl)-2-(1-methylethyl)-5,6-dihydroimidazo[2,1-b]thiazole;

2-cyclopropyl-3-(5-methylbenzo[b]thiophen-2-yl)-5,6-dihydroimidazo[2,1-b]thiazole;

3-(5-methylbenzo[b]thiophen-2-yl)-2-vinyl-5,6-dihydroimidazo[2,1-b]thiazole;

3-(5-methylbenzo[b]thiophen-2-yl)-2-(methylthio)-5,6-dihydroimidazo[2,1-b]thiazole;

[3-(5-methylbenzo[b]thiophen-2-yl)-5,6-dihydroimidazo[2,1-b]thiazol-2-yl]methanol;

1-[3-(5-methylbenzo[b]thiophen-2-yl)-5,6-dihydroimidazo[2,1-b]thiazol-2-yl]ethanol;

2-[3-(5-methylbenzo[b]thiophen-2-yl)-5,6-dihydroimidazo[2,1-b]thiazol-2-yl]ethanol;

2-methyl-3-(6-methylbenzo[b]thiophen-2-yl)-5,6-dihydroimidazo[2,1-b]thiazole;

2-ethyl-3-(6-methylbenzo[b]thiophen-2-yl)-5,6-dihydroimidazo[2,1-b]thiazole;

3-(6-methylbenzo[b]thiophen-2-yl)-2-propyl-5,6-dihydroimidazo[2,1-b]thiazole;

3-(6-methylbenzo[b]thiophen-2-yl)-2-(1-methylethyl)-5,6-dihydroimidazo[2,1-b]thiazole;

2-cyclopropyl-3-(6-methylbenzo[b]thiophen-2-yl)-5,6-dihydroimidazo[2,1-b]thiazole;

3-(6-methylbenzo[b]thiophen-2-yl)-2-vinyl-5,6-dihydroimidazo[2,1-b]thiazole;

3-(6-methylbenzo[b]thiophen-2-yl)-2-(methylthio)-5,6-dihydroimidazo[2,1-b]thiazole;

[3-(6-methylbenzo[b]thiophen-2-yl)-5,6-dihydroimidazo[2,1-b]thiazol-2-yl]methanol;

1-[3-(6-methylbenzo[b]thiophen-2-yl)-5,6-dihydroimidazo[2,1-b]thiazol-2-yl]ethanol;

2-[3-(6-methylbenzo[b]thiophen-2-yl)-5,6-dihydroimidazo[2,1-b]thiazol-2-yl]ethanol;

2-methyl-3-(7-methylbenzo[b]thiophen-2-yl)-5,6-dihydroimidazo[2,1-b]thiazole;

2-ethyl-3-(7-methylbenzo[b]thiophen-2-yl)-5,6-dihydroimidazo[2,1-b]thiazole;

3-(7-methylbenzo[b]thiophen-2-yl)-2-propyl-5,6-dihydroimidazo[2,1-b]thiazole;

3-(7-methylbenzo[b]thiophen-2-yl)-2-(1-methylethyl)-5,6-dihydroimidazo[2,1-b]thiazole;

2-cyclopropyl-3-(7-methylbenzo[b]thiophen-2-yl)-5,6-dihydroimidazo[2,1-b]thiazole;

3-(7-methylbenzo[b]thiophen-2-yl)-2-vinyl-5,6-dihydroimidazo[2,1-b]thiazole;

3-(7-methylbenzo[b]thiophen-2-yl)-2-(methylthio)-5,6-dihydroimidazo[2,1-b]thiazole;

[3-(7-methylbenzo[b]thiophen-2-yl)-5,6-dihydroimidazo[2,1-b]thiazol-2-yl]methanol;

1-[3-(7-methylbenzo[b]thiophen-2-yl)-5,6-dihydroimidazo[2,1-b]thiazol-2-yl]ethanol;

2-[3-(7-methylbenzo[b]thiophen-2-yl)-5,6-dihydroimidazo[2,1-b]thiazol-2-yl]ethanol;

2-methyl-3-[4-(methylthio)benzo[b]thiophen-2-yl]-5,6-dihydroimidazo[2,1-b]thiazole;

2-ethyl-3-[4-(methylthio)benzo[b]thiophen-2-yl]-5,6-dihydroimidazo[2,1-b]thiazole;

3-[4-(methylthio)benzo[b]thiophen-2-yl]-2-propyl-5,6-dihydroimidazo[2,1-b]thiazole;

2-(1-methylethyl)-3-[4-(methylthio)benzo[b]thiophen-2-yl]-5,6-dihydroimidazo[2,1-b]thiazole;

2-cyclopropyl-3-[4-(methylthio)benzo[b]thiophen-2-yl]-5,6-dihydroimidazo[2,1-b]thiazole;

3-[4-(methylthio)benzo[b]thiophen-2-yl]-2-vinyl-5,6-dihydroimidazo[2,1-b]thiazole;

2-(methylthio)-3-[4-(methylthio)benzo[b]thiophen-2-yl]-5,6-dihydroimidazo[2,1-b]thiazole;

[3-[4-(methylthio)benzo[b]thiophen-2-yl]-5,6-dihydroimidazo[2,1-b]thiazol-2-yl]methanol;

1-[3-[4-(methylthio)benzo[b]thiophen-2-yl]-5,6-dihydroimidazo[2,1-b]thiazol-2-yl]ethanol;

2-[3-[4-(methylthio)benzo[b]thiophen-2-yl]-5,6-dihydroimidazo[2,1-b]thiazol-2-yl]ethanol;

2-methyl-3-[5-(methylthio)benzo[b]thiophen-2-yl]-5,6-dihydroimidazo[2,1-b]thiazole;

2-ethyl-3-[5-(methylthio)benzo[b]thiophen-2-yl]-5,6-dihydroimidazo[2,1-b]thiazole;

3-[5-(methylthio)benzo[b]thiophen-2-yl]-2-propyl-5,6-dihydroimidazo[2,1-b]thiazole;

2-(1-methylethyl)-3-[5-(methylthio)benzo[b]thiophen-2-yl]-5,6-dihydroimidazo[2,1-b]thiazole;

2-cyclopropyl-3-[5-(methylthio)benzo[b]thiophen-2-yl]-5,6-dihydroimidazo[2,1-b]thiazole;

3-(5-(methylthio)benzo[b]thiophen-2-yl]-2-vinyl-5,6-dihydroimidazo[2,1-b]thiazole;

2-(methylthio)-3-[5-(methylthio)benzo[b]thiophen-2-yl]-5,6-dihydroimidazo[2,1-b]thiazole;

[3-[5-(methylthio)benzo[b]thiophen-2-yl]-5,6-dihydroimidazo[2,1-b]thiazol-2-yl]methanol;

1-[3-[5-(methylthio)benzo[b]thiophen-2-yl]-5,6-dihydroimidazo[2,1-b]thiazol-2-yl]ethanol;

2-[3-[5-(methylthio)benzo[b]thiophen-2-yl]-5,6-dihydroimidazo[2,1-b]thiazol-2-yl]ethanol;

2-methyl-3-[6-(methylthio)benzo[b]thiophen-2-yl]-5,6-dihydroimidazo[2,1-b]thiazole;

2-ethyl-3-[6-(methylthio)benzo[b]thiophen-2-yl]-5,6-dihydroimidazo[2,1-b]thiazole;

3-[6-(methylthio)benzo[b]thiophen-2-yl]-5,6-dihydroimidazo[2,1-b]thiazole;

2-(1-methylethyl)-3-[6-(methylthio)benzo[b]thiophen-2-yl]-5,6-dihydroimidazo[2,1-b]thiazole;

2-cyclopropyl-3-[6-(methylthio)benzo[b]thiophen-2-yl]-5,6-dihydroimidazo[2,1-b]thiazole;

3-[6-(methylthio)benzo[b]thiophen-2-yl]-2-vinyl-5,6-dihydroimidazo[2,1-b]thiazole;

2-(methylthio)-3-[6-(methylthio)benzo[b]thiophen-2-yl]-5,6-dihydroimidazo[2,1-b]thiazole;

[3-[6-(methylthio)benzo[b]thiophen-2-yl]-5,6-dihydroimidazo[2,1-b]thiazol-2-yl]methanol;

1-[3-[6-(methylthio)benzo[b]thiophen-2-yl]-5,6-dihydroimidazo[2,1-b]thiazol-2-yl]ethanol;

2-[3-[6-(methylthio)benzo[b]thiophen-2-yl]-5,6-dihydroimidazo[2,1-b]thiazol-2-yl]ethanol;

2-methyl-3-[7-(methylthio)benzo[b]thiophen-2-yl]-5,6-dihydroimidazo[2,1-b]thiazole;

2-ethyl-3-[7-(methylthio)benzo[b]thiophen-2-yl]-5,6-dihydroimidazo[2,1-b]thiazole;

3-[7-(methylthio)benzo[b]thiophen-2-yl]-2-propyl-5,6-dihydroimidazo[2,1-b]thiazole;

2-(1-methylethyl)-3-[7-(methylthio)benzo[b]thiophen-2-yl]-5,6-dihydroimidazo[2,1-b]thiazole;

2-cyclopropyl-3-[7-(methylthio)benzo[b]thiophen-2-yl]-5,6-dihydroimidazo[2,1-b]thiazole;

3-[7-(methylthio)benzo[b]thiophen-2-yl]-2-vinyl-5,6-dihydroimidazo[2,1-b]thiazole;

2-(methylthio)-3-[7-(methylthio)benzo[b]thiophen-2-yl]-5,6-dihydroimidazo[2,1-b]thiazole;

[3-[7-(methylthio)benzo[b]thiophen-2-yl]-5,6-dihydroimidazo[2,1-b]thiazol-2-yl]methanol;

1-[3-[7-(methylthio)benzo[b]thiophen-2-yl]-5,6-dihydroimidazo[2,1-b]thiazol-2-yl]ethanol;
2-[3-[7-(methylthio)benzo[b]thiophen-2-yl]-5,6-dihydroimidazo[2,1-b]thiazol-2-yl]ethanol;
3-(benzo[b]thiophen-4-yl)-2-propyl-5,6-dihydroimidazo[2,1-b]thiazole;
1-[3-(benzo[b]thiophen-4-yl)-5,6-dihydroimidazo[2,1-b]thiazol-2-yl]ethanol;
2-[3-(benzo[b]thiophen-4-yl)-5,6-dihydroimidazo[2,1-b]thiazol-2-yl]ethanol;
3-(6-chlorobenzo[b]thiophen-4-yl)-2-methyl-5,6-dihydroimidazo[2,1-b]thiazole;
3-(6-chlorobenzo[b]thiophen-4-yl)-2-ethyl-5,6-dihydroimidazo[2,1-b]thiazole;
3-(6-chlorobenzo[b]thiophen-4-yl)-2-propyl-5,6-dihydroimidazo[2,1-b]thiazole;
3-(6-chlorobenzo[b]thiophen-4-yl)-2-(1-methylethyl)-5,6-dihydroimidazo[2,1-b]thiazole;
3-(6-chlorobenzo[b]thiophen-4-yl)-2-cyclopropyl-5,6-dihydroimidazo[2,1-b]thiazole;
3-(6-chlorobenzo[b]thiophen-4-yl)-2-vinyl-5,6-dihydroimidazo[2,1-b]thiazole;
3-(6-chlorobenzo[b]thiophen-4-yl)-2-(methylthio)-5,6-dihydroimidazo[2,1-b]thiazole;
[3-(6-chlorobenzo[b]thiophen-4-yl)-5,6-dihydroimidazo[2,1-b]thiazol-2-yl]methanol;
1-[3-(6-chlorobenzo[b]thiophen-4-yl)-5,6-dihydroimidazo[2,1-b]thiazol-2-yl]ethanol;
2-[3-(6-chlorobenzo[b]thiophen-4-yl)-5,6-dihydroimidazo[2,1-b]thiazol-2-yl]ethanol;
3-(7-chlorobenzo[b]thiophen-4-yl)-2-methyl-5,6-dihydroimidazo[2,1-b]thiazole;
3-(7-chlorobenzo[b]thiophen-4-yl)-2-ethyl-5,6-dihydroimidazo[2,1-b]thiazole;
3-(7-chlorobenzo[b]thiophen-4-yl)-2-propyl-5,6-dihydroimidazo[2,1-b]thiazole;
3-(7-chlorobenzo[b]thiophen-4-yl)-2-(1-methylethyl)-5,6-dihydroimidazo[2,1-b]thiazole;
3-(7-chlorobenzo[b]thiophen-4-yl)-2-cyclopropyl-5,6-dihydroimidazo[2,1-b]thiazole;
3-(7-chlorobenzo[b]thiophen-4-yl)-2-vinyl-5,6-dihydroimidazo[2,1-b]thiazole;
3-(7-chlorobenzo[b]thiophen-4-yl)-2-(methylthio)-5,6-dihydroimidazo[2,1-b]thiazole;
[3-(7-chlorobenzo[b]thiophen-4-yl)-5,6-dihydroimidazo[2,1-b]thiazol-2-yl]methanol;
1-[3-(7-chlorobenzo[b]thiophen-4-yl)-5,6-dihydroimidazo[2,1-b]thiazol-2-yl]ethanol;
2-[3-(7-chlorobenzo[b]thiophen-4-yl)-5,6-dihydroimidazo[2,1-b]thiazol-2-yl]ethanol;
3-(6-fluorobenzo[b]thiophen-4-yl)-2-methyl-5,6-dihydroimidazo[2,1-b]thiazole;
3-(6-fluorobenzo[b]thiophen-4-yl)-2-ethyl-5,6-dihydroimidazo[2,1-b]thiazole;
3-(6-fluorobenzo[b]thiophen-4-yl)-2-propyl-5,6-dihydroimidazo[2,1-b]thiazole;
3-(6-fluorobenzo[b]thiophen-4-yl)-2-(1-methylethyl)-5,6-dihydroimidazo[2,1-b]thiazole;
3-(6-fluorobenzo[b]thiophen-4-yl)-2-cyclopropyl-5,6-dihydroimidazo[2,1-b]thiazole;
3-(6-fluorobenzo[b]thiophen-4-yl)-2-vinyl-5,6-dihydroimidazo[2,1-b]thiazole;
3-(6-fluorobenzo[b]thiophen-4-yl)-2-(methylthio)-5,6-dihydroimidazo[2,1-b]thiazole;
[3-(6-fluorobenzo[b]thiophen-4-yl)-5,6-dihydroimidazo[2,1-b]thiazol-2-yl]methanol;
1-[3-(6-fluorobenzo[b]thiophen-4-yl)-5,6-dihydroimidazo[2,1-b]thiazol-2-yl]ethanol;
2-[3-(6-fluorobenzo[b]thiophen-4-yl)-5,6-dihydroimidazo[2,1-b]thiazol-2-yl]ethanol;
3-(7-fluorobenzo[b]thiophen-4-yl)-2-ethyl-5,6-dihydroimidazo[2,1-b]thiazole;
3-(7-fluorobenzo[b]thiophen-4-yl)-2-propyl-5,6-dihydroimidazo[2,1-b]thiazole;
3-(7-fluorobenzo[b]thiophen-4-yl)-2-(1-methylethyl)-5,6-dihydroimidazo[2,1-b]thiazole;
3-(7-fluorobenzo[b]thiophen-4-yl)-2-cyclopropyl-5,6-dihydroimidazo[2,1-b]thiazole;
3-(7-fluorobenzo[b]thiophen-4-yl)-2-vinyl-5,6-dihydroimidazo[2,1-b]thiazole;
3-(7-fluorobenzo[b]thiophen-4-yl)-2-(methylthio)-5,6-dihydroimidazo[2,1-b]thiazole;
[3-(7-fluorobenzo[b]thiophen-4-yl)-5,6-dihydroimidazo[2,1-b]thiazol-2-yl]methanol;
1-[3-(7-fluorobenzo[b]thiophen-4-yl)-5,6-dihydroimidazo[2,1-b]thiazol-2-yl]ethanol;
2-[3-(7-fluorobenzo[b]thiophen-4-yl)-5,6-dihydroimidazo[2,1-b]thiazol-2-yl]ethanol;
3-(6-methoxybenzo[b]thiophen-4-yl)-2-methyl-5,6-dihydroimidazo[2,1-b]thiazole;
2-ethyl-3-(6-methoxybenzo[b]thiophen-2-yl)-5,6-dihydroimidazo[2,1-b]thiazole;
3-(6-methoxybenzo[b]thiophen-4-yl)-2-propyl-5,6-dihydroimidazo[2,1-b]thiazole;
3-(6-methoxybenzo[b]thiophen-4-yl)-2-(1-methylethyl)-5,6-dihydroimidazo[2,1-b]thiazole;
2-cyclopropyl-3-(6-methoxybenzo[b]thiophen-4-yl)-5,6-dihydroimidazo[2,1-b]thiazole;
3-(6-methoxybenzo[b]thiophen-4-yl)-2-vinyl-5,6-dihydroimidazo[2,1-b]thiazole;
3-(6-methoxybenzo[b]thiophen-4-yl)-2-(methylthio)-5,6-dihydroimidazo[2,1-b]thiazole;
[3-(6-methoxybenzo[b]thiophen-4-yl)-5,6-dihydroimidazo[2,1-b]thiazol-2-yl]methanol;
1-[3-(6-methoxybenzo[b]thiophen-4-yl)-5,6-dihydroimidazo[2,1-b]thiazol-2-yl]ethanol;
2-[3-(6-methoxybenzo[b]thiophen-4-yl)-5,6-dihydroimidazo[2,1-b]thiazol-2-yl]ethanol;
3-(7-methoxybenzo[b]thiophen-4-yl)-2-methyl-5,6-dihydroimidazo[2,1-b]thiazole;
2-ethyl-3-(7-methoxybenzo[b]thiophen-4-yl)-5,6-dihydroimidazo[2,1-b]thiazole;
3-(7-methoxybenzo[b]thiophen-4-yl)-2-propyl-5,6-dihydroimidazo[2,1-b]thiazole;
3-(7-methoxybenzo[b]thiophen-4-yl)-2-(1-methylethyl)-5,6-dihydroimidazo[2,1-b]thiazole;
2-cyclopropyl-3-(7-methoxybenzo[b]thiophen-4-yl)-5,6-dihydroimidazo[2,1-b]thiazole;
3-(7-methoxybenzo[b]thiophen-4-yl)-2-vinyl-5,6-dihydroimidazo[2,1-b]thiazole;
3-(7-methoxybenzo[b]thiophen-4-yl)-2-(methylthio)-5,6-dihydroimidazo[2,1-b]thiazole;
[3-(7-methoxybenzo[b]thiophen-4-yl)-5,6-dihydroimidazo[2,1-b]thiazol-2-yl]methanol;

1-[3-(7-methoxybenzo[b]thiophen-4-yl)-5,6-dihydroimidazo[2,1-b]thiazol-2-yl]ethanol;

2-[3-(7-methoxybenzo[b]thiophen-4-yl)-5,6-dihydroimidazo[2,1-b]thiazol-2-yl]ethanol;

2-ethyl-3-(2-methylbenzo[b]thiophen-4-yl)-5,6-dihydroimidazo[2,1-b]thiazole;

3-(2-methylbenzo[b]thiophen-4-yl)-2-propyl-5,6-dihydroimidazo[2,1-b]thiazole;

3-(2-methylbenzo[b]thiophen-4-yl)-2-(1-methylethyl)-5,6-dihydroimidazo[2,1-b]thiazole;

2-cyclopropyl-3-(2-methylbenzo[b]thiophen-4-yl)-5,6-dihydroimidazo[2,1-b]thiazole;

3-(2-methylbenzo[b]thiophen-4-yl)-2-vinyl-5,6-dihydroimidazo[2,1-b]thiazole;

3-(2-methylbenzo[b]thiophen-4-yl)-2-(methylthio)-5,6-dihydroimidazo[2,1-b]thiazole;

[3-(2-methylbenzo[b]thiophen-4-yl)-5,6-dihydroimidazo[2,1-b]thiazol-2-yl]methanol;

1-[3-(2-methylbenzo[b]thiophen-4-yl)-5,6-dihydroimidazo[2,1-b]thiazol-2-yl]ethanol;

2-[3-(2-methylbenzo[b]thiophen-4-yl)-5,6-dihydroimidazo[2,1-b]thiazol-2-yl]ethanol;

2-methyl-3-(3-methylbenzo[b]thiophen-4-yl)-5,6-dihydroimidazo[2,1-b]thiazole;

2-ethyl-3-(3-methylbenzo[b]thiophen-4-yl)-5,6-dihydroimidazo[2,1-b]thiazole;

3-(3-methylbenzo[b]thiophen-4-yl)-2-propyl-5,6-dihydroimidazo[2,1-b]thiazole;

3-(3-methylbenzo[b]thiophen-4-yl)-2-(1-methylethyl)-5,6-dihydroimidazo[2,1-b]thiazole;

2-cyclopropyl-3-(3-methylbenzo[b]thiophen-4-yl)-5,6-dihydroimidazo[2,1-b]thiazole;

3-(3-methylbenzo[b]thiophen-4-yl)-2-vinyl-5,6-dihydroimidazo[2,1-b]thiazole;

3-(3-methylbenzo[b]thiophen-4-yl)-2-(methylthio)-5,6-dihydroimidazo[2,1-b]thiazole;

[3-(3-methylbenzo[b]thiophen-4-yl)-5,6-dihydroimidazo[2,1-b]thiazol-2-yl]methanol;

1-[3-(3-methylbenzo[b]thiophen-4-yl)-5,6-dihydroimidazo[2,1-b]thiazol-2-yl]ethanol;

2-[3-(3-methylbenzo[b]thiophen-4-yl)-5,6-dihydroimidazo[2,1-b]thiazol-2-yl]ethanol;

2-methyl-3-(6-methylbenzo[b]thiophen-4-yl)-5,6-dihydroimidazo[2,1-b]thiazole;

2-ethyl-3-(6-methylbenzo[b]thiophen-4-yl)-5,6-dihydroimidazo[2,1-b]thiazole;

3-(6-methylbenzo[b]thiophen-4-yl)-2-propyl-5,6-dihydroimidazo[2,1-b]thiazole;

3-(6-methylbenzo[b]thiophen-4-yl)-2-(1-methylethyl)-5,6-dihydroimidazo[2,1-b]thiazole;

2-cyclopropyl-3-(6-methylbenzo[b]thiophen-4-yl)-5,6-dihydroimidazo[2,1-b]thiazole;

3-(6-methylbenzo[b]thiophen-4-yl)-2-vinyl-5,6-dihydroimidazo[2,1-b]thiazole;

3-(6-methylbenzo[b]thiophen-4-yl)-2-(methylthio)-5,6-dihydroimidazo[2,1-b]thiazole;

[3-(6-methylbenzo[b]thiophen-4-yl)-5,6-dihydroimidazo[2,1-b]thiazol-2-yl]methanol;

1-[3-(6-methylbenzo[b]thiophen-4-yl)-5,6-dihydroimidazo[2,1-b]thiazol-2-yl]ethanol;

2-[3-(6-methylbenzo[b]thiophen-4-yl)-5,6-dihydroimidazo[2,1-b]thiazol-2-yl]ethanol;

2-methyl-3-(7-methylbenzo[b]thiophen-4-yl)-5,6-dihydroimidazo[2,1-b]thiazole;

2-ethyl-3-(7-methylbenzo[b]thiophen-4-yl)-5,6-dihydroimidazo[2,1-b]thiazole;

3-(7-methylbenzo[b]thiophen-4-yl)-2-propyl-5,6-dihydroimidazo[2,1-b]thiazole;

3-(7-methylbenzo[b]thiophen-4-yl)-2-(1-methylethyl)-5,6-dihydroimidazo[2,1-b]thiazole;

2-cyclopropyl-3-(7-methylbenzo[b]thiophen-4-yl)-5,6-dihydroimidazo[2,1-b]thiazole;

3-(7-methylbenzo[b]thiophen-4-yl)-2-vinyl-5,6-dihydroimidazo[2,1-b]thiazole;

3-(7-methylbenzo[b]thiophen-4-yl)-2-(methylthio)-5,6-dihydroimidazo[2,1-b]thiazole;

[3-(7-methylbenzo[b]thiophen-4-yl)-5,6-dihydroimidazo[2,1-b]thiazol-2-yl]methanol;

1-[3-(7-methylbenzo[b]thiophen-4-yl)-5,6-dihydroimidazo[2,1-b]thiazol-2-yl]ethanol;

2-[3-(7-methylbenzo[b]thiophen-4-yl)-5,6-dihydroimidazo[2,1-b]thiazol-2-yl]ethanol;

2-methyl-3-[6-(methylthio)benzo[b]thiophen-4-yl]-5,6-dihydroimidazo[2,1-b]thiazole;

2-ethyl-3-[6-(methylthio)benzo[b]thiophen-4-yl]-5,6-dihydroimidazo[2,1-b]thiazole;

3-[6-(methylthio)benzo[b]thiophen-4-yl]-2-propyl-5,6-dihydroimidazo[2,1-b]thiazole;

2-(1-methylethyl)-3-[6-(methylthio)benzo[b]thiophen-4-yl]-5,6-dihydroimidazo[2,1-b]thiazole;

2-cyclopropyl-3-[6-(methylthio)benzo[b]thiophen-4-yl]-5,6-dihydroimidazo[2,1-b]thiazole;

3-[6-(methylthio)benzo[b]thiophen-4-yl]-2-vinyl-5,6-dihydroimidazo[2,1-b]thiazole;

2-(methylthio)-3-[6-(methylthio)benzo[b]thiophen-4-yl]-5,6-dihydroimidazo[2,1-b]thiazole;

[3-[6-(methylthio)benzo[b]thiophen-4-yl]-5,6-dihydroimidazo[2,1-b]thiazol-2-yl]methanol;

1-[3-[6-(methylthio)benzo[b]thiophen-4-yl]-5,6-dihydroimidazo[2,1-b]thiazol-2-yl]ethanol;

2-[3-[6-(methylthio)benzo[b]thiophen-4-yl]-5,6-dihydroimidazo[2,1-b]thiazol-2-yl]ethanol;

2-methyl-3-[7-(methylthio)benzo[b]thiophen-4-yl]-5,6-dihydroimidazo[2,1-b]thiazole;

2-ethyl-3-[7-(methylthio)benzo[b]thiophen-4-yl]-5,6-dihydroimidazo[2,1-b]thiazole;

3-[7-(methylthio)benzo[b]thiophen-4-yl]-2-propyl-5,6-dihydroimidazo[2,1-b]thiazole;

2-(1-methylethyl)-3-[7-(methylthio)benzo[b]thiophen-4-yl]-5,6-dihydroimidazo[2,1-b]thiazole;

2-cyclopropyl-3-[7-(methylthio)benzo[b]thiophen-4-yl]-5,6-dihydroimidazo[2,1-b]thiazole;

3-[7-(methylthio)benzo[b]thiophen-4-yl]-2-vinyl-5,6-dihydroimidazo[2,1-b]thiazole;

2-(methylthio)-3-[7-(methylthio)benzo[b]thiophen-4-yl]-5,6-dihydroimidazo[2,1-b]thiazole;

[3-[7-(methylthio)benzo[b]thiophen-4-yl]-5,6-dihydroimidazo[2,1-b]thiazol-2-yl]methanol;

1-[3-[7-(methylthio)benzo[b]thiophen-4-yl]-5,6-dihydroimidazo[2,1-b]thiazol-2-yl]ethanol;

2-[3-[7-(methylthio)benzo[b]thiophen-4-yl]-5,6-dihydroimidazo[2,1-b]thiazol-2-yl]ethanol;

3-(benzo[b]thiophen-5-yl)-2-propyl-5,6-dihydroimidazo[2,1-b]thiazole;

3-(benzo[b]thiophen-5-yl)-2-cyclopropyl-5,6-dihydroimidazo[2,1-b]thiazole;
3-(benzo[b]thiophen-5-yl)-2-vinyl-5,6-dihydroimidazo[2,1-b]thiazole;
1-[3-(benzo[b]thiophen-5-yl)-5,6-dihydroimidazo[2,1-b]thiazol-2-yl]ethanol;
2-[3-(benzo[b]thiophen-5-yl)-5,6-dihydroimidazo[2,1-b]thiazol-2-yl]ethanol;
3-(7-chlorobenzo[b]thiophen-5-yl)-2-methyl-5,6-dihydroimidazo[2,1-b]thiazole;
3-(7-chlorobenzo[b]thiophen-5-yl)-2-ethyl-5,6-dihydroimidazo[2,1-b]thiazole;
3-(7-chlorobenzo[b]thiophen-5-yl)-2-propyl-5,6-dihydroimidazo[2,1-b]thiazole;
3-(7-chlorobenzo[b]thiophen-5-yl)-2-(1-methylethyl)-5,6-dihydroimidazo[2,1-b]thiazole;
3-(7-chlorobenzo[b]thiophen-5-yl)-2-cyclopropyl-5,6-dihydroimidazo[2,1-b]thiazole;
3-(7-chlorobenzo[b]thiophen-5-yl)-2-vinyl-5,6-dihydroimidazo[2,1-b]thiazole;
3-(7-chlorobenzo[b]thiophen-5-yl)-2-(methylthio)-5,6-dihydroimidazo[2,1-b]thiazole;
[3-(7-chlorobenzo[b]thiophen-5-yl)-5,6-dihydroimidazo[2,1-b]thiazol-2-yl]methanol;
1-[3-(7-chlorobenzo[b]thiophen-5-yl)-5,6-dihydroimidazo[2,1-b]thiazol-2-yl]ethanol;
2-[3-(7-chlorobenzo[b]thiophen-5-yl)-5,6-dihydroimidazo[2,1-b]thiazol-2-yl]ethanol;
3-(7-fluorobenzo[b]thiophen-5-yl)-2-methyl-5,6-dihydroimidazo[2,1-b]thiazole;
3-(7-fluorobenzo[b]thiophen-5-yl)-2-ethyl-5,6-dihydroimidazo[2,1-b]thiazole;
3-(7-fluorobenzo[b]thiophen-5-yl)-2-propyl-5,6-dihydroimidazo[2,1-b]thiazole;
3-(7-fluorobenzo[b]thiophen-5-yl)-2-(1-methylethyl)-5,6-dihydroimidazo[2,1-b]thiazole;
3-(7-fluorobenzo[b]thiophen-5-yl)-2-cyclopropyl-5,6-dihydroimidazo[2,1-b]thiazole;
3-(7-fluorobenzo[b]thiophen-5-yl)-2-vinyl-5,6-dihydroimidazo[2,1-b]thiazole;
3-(7-fluorobenzo[b]thiophen-5-yl)-2-(methylthio)-5,6-dihydroimidazo[2,1-b]thiazole;
[3-(7-fluorobenzo[b]thiophen-5-yl)-5,6-dihydroimidazo[2,1-b]thiazol-2-yl]methanol;
1-[3-(7-fluorobenzo[b]thiophen-5-yl)-5,6-dihydroimidazo[2,1-b]thiazol-2-yl]ethanol;
2-[3-(7-fluorobenzo[b]thiophen-5-yl)-5,6-dihydroimidazo[2,1-b]thiazol-2-yl]ethanol;
3-(7-methoxybenzo[b]thiophen-5-yl)-2-methyl-5,6-dihydroimidazo[2,1-b]thiazole;
2-ethyl-3-(7-methoxybenzo[b]thiophen-5-yl)-5,6-dihydroimidazo[2,1-b]thiazole;
3-(7-methoxybenzo[b]thiophen-5-yl)-2-propyl-5,6-dihydroimidazo[2,1-b]thiazole;
3-(7-methoxybenzo[b]thiophen-5-yl)-2-(1-methylethyl)-5,6-dihydroimidazo[2,1-b]thiazole;
2-cyclopropyl-3-(7-methoxybenzo[b]thiophen-5-yl)-5,6-dihydroimidazo[2,1-b]thiazole;
3-(7-methoxybenzo[b]thiophen-5-yl)-2-vinyl-5,6-dihydroimidazo[2,1-b]thiazole;
3-(7-methoxybenzo[b]thiophen-5-yl)-2-(methylthio)-5,6-dihydroimidazo[2,1-b]thiazole;
[3-(7-methoxybenzo[b]thiophen-5-yl)-5,6-dihydroimidazo[2,1-b]thiazol-2-yl]methanol;
1-[3-(7-methoxybenzo[b]thiophen-5-yl)-5,6-dihydroimidazo[2,1-b]thiazol-2-yl]ethanol;
2-[3-(7-methoxybenzo[b]thiophen-5-yl)-5,6-dihydroimidazo[2,1-b]thiazol-2-yl]ethanol;
2-methyl-3-(2-methylbenzo[b]thiophen-5-yl)-5,6-dihydroimidazo[2,1-b]thiazole;
2-ethyl-3-(2-methylbenzo[b]thiophen-5-yl)-5,6-dihydroimidazo[2,1-b]thiazole;
3-(2-methylbenzo[b]thiophen-5-yl)-2-propyl-5,6-dihydroimidazo[2,1-b]thiazole;
3-(2-methylbenzo[b]thiophen-5-yl)-2-(1-methylethyl)-5,6-dihydroimidazo[2,1-b]thiazole;
2-cyclopropyl-3-(2-methylbenzo[b]thiophen-5-yl)-5,6-dihydroimidazo[2,1-b]thiazole;
3-(2-methylbenzo[b]thiophen-5-yl)-2-vinyl-5,6-dihydroimidazo[2,1-b]thiazole;
3-(2-methylbenzo[b]thiophen-5-yl)-2-(methylthio)-5,6-dihydroimidazo[2,1-b]thiazole;
[3-(2-methylbenzo[b]thiophen-5-yl)-5,6-dihydroimidazo[2,1-b]thiazol-2-yl]methanol;
1-[3-(2-methylbenzo[b]thiophen-5-yl)-5,6-dihydroimidazo[2,1-b]thiazol-2-yl]ethanol;
2-[3-(2-methylbenzo[b]thiophen-5-yl)-5,6-dihydroimidazo[2,1-b]thiazol-2-yl]ethanol;
2-methyl-3-(3-methylbenzo[b]thiophen-5-yl)-5,6-dihydroimidazo[2,1-b]thiazole;
2-ethyl-3-(3-methylbenzo[b]thiophen-5-yl)-5,6-dihydroimidazo[2,1-b]thiazole;
3-(3-methylbenzo[b]thiophen-5-yl)-2-propyl-5,6-dihydroimidazo[2,1-b]thiazole;
3-(3-methylbenzo[b]thiophen-5-yl)-2-(1-methylethyl)-5,6-dihydroimidazo[2,1-b]thiazole;
2-cyclopropyl-3-(3-methylbenzo[b]thiophen-5-yl)-5,6-dihydroimidazo[2,1-b]thiazole;
3-(3-methylbenzo[b]thiophen-5-yl)-2-vinyl-5,6-dihydroimidazo[2,1-b]thiazole;
3-(3-methylbenzo[b]thiophen-5-yl)-2-(methylthio)-5,6-dihydroimidazo[2,1-b]thiazole;
[3-(3-methylbenzo[b]thiophen-5-yl)-5,6-dihydroimidazo[2,1-b]thiazol-2-yl]methanol;
1-[3-(3-methylbenzo[b]thiophen-5-yl)-5,6-dihydroimidazo[2,1-b]thiazol-2-yl]ethanol;
2-[3-(3-methylbenzo[b]thiophen-5-yl)-5,6-dihydroimidazo[2,1-b]thiazol-2-yl]ethanol;
2-methyl-3-(7-methylbenzo[b]thiophen-5-yl)-5,6-dihydroimidazo[2,1-b]thiazole;
2-ethyl-3-(7-methylbenzo[b]thiophen-5-yl)-5,6-dihydroimidazo[2,1-b]thiazole;
3-(7-methylbenzo[b]thiophen-5-yl)-2-propyl-5,6-dihydroimidazo[2,1-b]thiazole;
3-(7-methylbenzo[b]thiophen-5-yl)-2-(1-methylethyl)-5,6-dihydroimidazo[2,1-b]thiazole;
2-cyclopropyl-3-(7-methylbenzo[b]thiophen-5-yl)-5,6-dihydroimidazo[2,1-b]thiazole;
3-(7-methylbenzo[b]thiophen-5-yl)-2-vinyl-5,6-dihydroimidazo[2,1-b]thiazole;
3-(7-methylbenzo[b]thiophen-5-yl)-2-(methylthio)-5,6-dihydroimidazo[2,1-b]thiazole;
[3-(7-methylbenzo[b]thiophen-5-yl)-5,6-dihydroimidazo[2,1-b]thiazol-2-yl]methanol;

1-[3-(7-methylbenzo[b]thiophen-5-yl)-5,6-dihydroimidazo[2,1-b]thiazol-2-yl]ethanol;

2-[3-(7-methylbenzo[b]thiophen-5-yl)-5,6-dihydroimidazo[2,1-b]thiazol-2-yl]ethanol;

2-methyl-3-[7-(methylthio)benzo[b]thiophen-5-yl]-5,6-dihydroimidazo[2,1-b]thiazole;

2-ethyl-3-[7-(methylthio)benzo[b]thiophen-5-yl]-5,6-dihydroimidazo[2,1-b]thiazole;

3-[7-(methylthio)benzo[b]thiophen-5-yl]-2-propyl-5,6-dihydroimidazo[2,1-b]thiazole;

2-(1-methylethyl)-3-[7-(methylthio)benzo[b]thiophen-5-yl]-5,6-dihydroimidazo[2,1-b]thiazole;

2-cyclopropyl-3-[7-(methylthio)benzo[b]thiophen-5-yl]-5,6-dihydroimidazo[2,1-b]thiazole;

3-[7-(methylthio)benzo[b]thiophen-5-yl]-2-vinyl-5,6-dihydroimidazo[2,1-b]thiazole;

2-(methylthio)-3-[7-(methylthio)benzo[b]thiophen-5-yl]-5,6-dihydroimidazo[2,1-b]thiazole;

[3-[7-(methylthio)benzo[b]thiophen-5-yl]-5,6-dihydroimidazo[2,1-b]thiazol-2-yl]methanol;

1-[3-[7-(methylthio)benzo[b]thiophen-5-yl]-5,6-dihydroimidazo[2,1-b]thiazol-2-yl]ethanol;

2-[3-[7-(methylthio)benzo[b]thiophen-5-yl]-5,6-dihydroimidazo[2,1-b]thiazol-2-yl]ethanol;

3-(benzo[b]thiophen-6-yl)-2-ethyl-5,6-dihydroimidazo[2,1-b]thiazole;

3-(benzo[b]thiophen-6-yl)-2-propyl-5,6-dihydroimidazo[2,1-b]thiazole;

3-(benzo[b]thiophen-6-yl)-2-(1-methylethyl)-5,6-dihydroimidazo[2,1-b]thiazole;

3-(benzo[b]thiophen-6-yl)-2-cyclopropyl-5,6-dihydroimidazo[2,1-b]thiazole;

3-(benzo[b]thiophen-6-yl)-2-vinyl-5,6-dihydroimidazo[2,1-b]thiazole;

3-(benzo[b]thiophen-6-yl)-2-(methylthio)-5,6-dihydroimidazo[2,1-b]thiazole;

[3-(benzo[b]thiophen-6-yl)-5,6-dihydroimidazo[2,1-b]thiazol-2-yl]methanol;

1-[3-(benzo[b]thiophen-6-yl)-5,6-dihydroimidazo[2,1-b]thiazol-2-yl]ethanol;

2-[3-(benzo[b]thiophen-6-yl)-5,6-dihydroimidazo[2,1-b]thiazol-2-yl]ethanol;

3-(4-chlorobenzo[b]thiophen-6-yl)-2-methyl-5,6-dihydroimidazo[2,1-b]thiazole;

3-(4-chlorobenzo[b]thiophen-6-yl)-2-ethyl-5,6-dihydroimidazo[2,1-b]thiazole;

3-(4-chlorobenzo[b]thiophen-6-yl)-2-propyl-5,6-dihydroimidazo[2,1-b]thiazole;

3-(4-chlorobenzo[b]thiophen-6-yl)-2-(1-methylethyl)-5,6-dihydroimidazo[2,1-b]thiazole;

3-(4-chlorobenzo[b]thiophen-6-yl)-2-cyclopropyl-5,6-dihydroimidazo[2,1-b]thiazole;

3-(4-chlorobenzo[b]thiophen-6-yl)-2-vinyl-5,6-dihydroimidazo[2,1-b]thiazole;

3-(4-chlorobenzo[b]thiophen-6-yl)-2-(methylthio)-5,6-dihydroimidazo[2,1-b]thiazole;

[3-(4-chlorobenzo[b]thiophen-6-yl)-5,6-dihydroimidazo[2,1-b]thiazol-2-yl]methanol;

1-[3-(4-chlorobenzo[b]thiophen-6-yl)-5,6-dihydroimidazo[2,1-b]thiazol-2-yl]ethanol;

2-[3-(4-chlorobenzo[b]thiophen-6-yl)-5,6-dihydroimidazo[2,1-b]thiazol-2-yl]ethanol;

3-(4-fluorobenzo[b]thiophen-6-yl)-2-methyl-5,6-dihydroimidazo[2,1-b]thiazole;

3-(4-fluorobenzo[b]thiophen-6-yl)-2-ethyl-5,6-dihydroimidazo[2,1-b]thiazole;

3-(4-fluorobenzo[b]thiophen-6-yl)-2-propyl-5,6-dihydroimidazo[2,1-b]thiazole;

3-(4-fluorobenzo[b]thiophen-6-yl)-2-(1-methylethyl)-5,6-dihydroimidazo[2,1-b]thiazole;

3-(4-fluorobenzo[b]thiophen-6-yl)-2-cyclopropyl-5,6-dihydroimidazo[2,1-b]thiazole;

3-(4-fluorobenzo[b]thiophen-6-yl)-2-vinyl-5,6-dihydroimidazo[2,1-b]thiazole;

3-(4-fluorobenzo[b]thiophen-6-yl)-5,6-dihydroimidazo[2,1-b]thiazol-2-yl]methanol;

[3-(4-fluorobenzo[b]thiophen-6-yl)-5,6-dihydroimidazo[2,1-b]thiazol-2-yl]methanol;

1-[3-(4-fluorobenzo[b]thiophen-6-yl)-5,6-dihydroimidazo[2,1-b]thiazol-2-yl]ethanol;

2-[3-(4-fluorobenzo[b]thiophen-6-yl)-5,6-dihydroimidazo[2,1-b]thiazol-2-yl]ethanol;

3-(4-methoxybenzo[b]thiophen-6-yl)-2-methyl-5,6-dihydroimidazo[2,1-b]thiazole;

2-ethyl-3-(4-methoxybenzo[b]thiophen-6-yl)-5,6-dihydroimidazo[2,1-b]thiazole;

3-(4-methoxybenzo[b]thiophen-6-yl)-2-propyl-5,6-dihydroimidazo[2,1-b]thiazole;

3-(4-methoxybenzo[b]thiophen-6-yl)-2-(1-methylethyl)-5,6-dihydroimidazo[2,1-b]thiazole;

2-cyclopropyl-3-(4-methoxybenzo[b]thiophen-6-yl)-5,6-dihydroimidazo[2,1-b]thiazole;

3-(4-methoxybenzo[b]thiophen-6-yl)-2-vinyl-5,6-dihydroimidazo[2,1-b]thiazole;

3-(4-methoxybenzo[b]thiophen-6-yl)-2-(methylthio)-5,6-dihydroimidazo[2,1-b]thiazole;

[3-(4-methoxybenzo[b]thiophen-6-yl)-5,6-dihydroimidazo[2,1-b]thiazol-2-yl]methanol;

1-[3-(4-methoxybenzo[b]thiophen-6-yl)-5,6-dihydroimidazo[2,1-b]thiazol-2-yl]ethanol;

2-[3-(4-methoxybenzo[b]thiophen-6-yl)-5,6-dihydroimidazo[2,1-b]thiazol-2-yl]ethanol;

2-methyl-3-(2-methylbenzo[b]thiophen-6-yl)-5,6-dihydroimidazo[2,1-b]thiazole;

2-ethyl-3-(2-methylbenzo[b]thiophen-6-yl)-5,6-dihydroimidazo[2,1-b]thiazole;

3-(2-methylbenzo[b]thiophen-6-yl)-2-propyl-5,6-dihydroimidazo[2,1-b]thiazole;

3-(2-methylbenzo[b]thiophen-6-yl)-2-(1-methylethyl)-5,6-dihydroimidazo[2,1-b]thiazole;

2-cyclopropyl-3-(2-methylbenzo[b]thiophen-yl)-5,6-dihydroimidazo[2,1-b]thiazole;

3-(2-methylbenzo[b]thiophen-6-yl)-2-vinyl-5,6-dihydroimidazo[2,1-b]thiazole;

3-(2-methylbenzo[b]thiophen-6-yl)-2-(methylthio)-5,6-dihydroimidazo[2,1-b]thiazole;

[3-(2-methylbenzo[b]thiophen-6-yl)-5,6-dihydroimidazo[2,1-b]thiazol-2-yl]methanol;

1-[3-(2-methylbenzo[b]thiophen-6-yl)-5,6-dihydroimidazo[2,1-b]thiazol-2-yl]ethanol;

2-[3-(2-methylbenzo[b]thiophen-6-yl)-5,6-dihydroimidazo[2,1-b]thiazol-2-yl]ethanol;

2-methyl-3-(3-methylbenzo[b]thiophen-6-yl)-5,6-dihydroimidazo[2,1-b]thiazole;

2-ethyl-3-(3-methylbenzo[b]thiophen-6-yl)-5,6-dihydroimidazo[2,1-b]thiazole;
3-(3-methylbenzo[b]thiophen-6-yl)-2-propyl-5,6-dihydroimidazo[2,1-b]thiazole;
3-(3-methylbenzo[b]thiophen-6-yl)-2-(1-methylethyl)-5,6-dihydroimidazo[2,1-b]thiazole;
2-cyclopropyl-3-(3-methylbenzo[b]thiophen-6-yl)-5,6-dihydroimidazo[2,1-b]thiazole;
3-(3-methylbenzo[b]thiophen-6-yl)-2-vinyl-5,6-dihydroimidazo[2,1-b]thiazole;
3-(3-methylbenzo[b]thiophen-6-yl]-2-(methylthio)-5,6-dihydroimidazo[2,1-b]thiazole;
[3-(3-methylbenzo[b]thiophen-6-yl)-5,6-dihydroimidazo[2,1-b]thiazol-2-yl]methanol;
1-[3-(3-methylbenzo[b]thiophen-6-yl)-5,6-dihydroimidazo[2,1-b]thiazol-2-yl]ethanol;
2-[3-(3-methylbenzo[b]thiophen-6-yl)-5,6-dihydroimidazo[2,1-b]thiazol-2-yl]ethanol;
2-methyl-3-(4-methylbenzo[b]thiophen-6-yl)-5,6-dihydroimidazo[2,1-b]thiazole;
2-ethyl-3-(4-methylbenzo[b]thiophen-6-yl)-5,6-dihydroimidazo[2,1-b]thiazole;
3-(4-methylbenzo[b]thiophen-6-yl)-2-propyl-5,6-dihydroimidazo[2,1-b]thiazole;
3-(4-methylbenzo[b]thiophen-6-yl)-2-(1-methylethyl)-5,6-dihydroimidazo[2,1-b]thiazole;
2-cyclopropyl-3-(4-methylbenzo[b]thiophen-6-yl)-5,6-dihydroimidazo[2,1-b]thiazole;
3-(4-methylbenzo[b]thiophen-6-yl)-2-vinyl-5,6-dihydroimidazo[2,1-b]thiazole;
3-(4-methylbenzo[b]thiophen-6-yl)-2-(methylthio)-5,6-dihydroimidazo[2,1-b]thiazole;
[3-(4-methylbenzo[b]thiophen-6-yl)-5,6-dihydroimidazo[2,1-b]thiazol-2-yl]methanol;
1-[3-(4-methylbenzo[b]thiophen-6-yl)-5,6-dihydroimidazo[2,1-b]thiazol-2-yl]ethanol;
2-[3-(4-methylbenzo[b]thiophen-6-yl)-5,6-dihydroimidazo[2,1-b]thiazol-2-yl]ethanol;
2-methyl-3-[4-(methylthio)benzo[b]thiophen-6-yl]-5,6-dihydroimidazo[2,1-b]thiazole;
2-ethyl-3-[4-(methylthio)benzo[b]thiophen-6-yl]-5,6-dihydroimidazo[2,1-b]thiazole;
3-[4-(methylthio)benzo[b]thiophen-6-yl]2-propyl-5,6-dihydroimidazo[2,1-b]thiazole;
2-(1-methylethyl)-3-[4-(methylthio)benzo[b]thiophen-6-yl]-5,6-dihydroimidazo[2,1-b]thiazole;
2-cyclopropyl-3-[4-(methylthio)benzo[b]thiophen-6-yl]-5,6-dihydroimidazo[2,1-b]thiazole;
3-[4-(methylthio)benzo[b]thiophen-6-yl]-2-vinyl-5,6-dihydroimidazo[2,1-b]thiazole;
2-(methylthio)-3-[4-(methylthio)benzo[b]thiophen-6-yl]-5,6-dihydroimidazo[2,1-b]thiazole;
[3-[4-(methylthio)benzo[b]thiophen-6-yl]-5,6-dihydroimidazo[2,1-b]thiazol-2-yl]methanol;
1-[3-[4-(methylthio)benzo[b]thiophen-6-yl]-5,6-dihydroimidazo[2,1-b]thiazol-2-yl]ethanol;
2-[3-[4-(methylthio)benzo[b]thiophen-6-yl]-5,6-dihydroimidazo[2,1-b]thiazol-2-yl]ethanol;
3-(benzo[b]thiophen-7-yl)-2-ethyl-5,6-dihydroimidazo[2,1-b]thiazole;
3-(benzo[b]thiophen-7-yl)-2-propyl-5,6-dihydroimidazo[2,1-b]thiazole;
3-(benzo[b]thiophen-7-yl)-2-(1-methylethyl)-5,6-dihydroimidazo[2,1-b]thiazole;
3-(benzo[b]thiophen-7-yl)-2-cyclopropyl-5,6-dihydroimidazo[2,1-b]thiazole;
3-(benzo[b]thiophen-7-yl)-2-vinyl-5,6-dihydroimidazo[2,1-b]thiazole;
3-(benzo[b]thiophen-7-yl)-2-(methylthio)-5,6-dihydroimidazo[2,1-b]thiazole;
[3-(benzo[b]thiophen-7-yl)-5,6-dihydroimidazo[2,1-b]thiazol-2-yl]methanol;
1-[3-(benzo[b]thiophen-7-yl)-5,6-dihydroimidazo[2,1-b]thiazol-2-yl]ethanol;
2-[3-(benzo[b]thiophen-7-yl)-5,6-dihydroimidazo[2,1-b]thiazol-2-yl]ethanol;
3-(4-chlorobenzo[b]thiophen-7-yl)-2-methyl-5,6-dihydroimidazo[2,1-b]thiazole;
3-(4-chlorobenzo[b]thiophen-7-yl)-2-ethyl-5,6-dihydroimidazo[2,1-b]thiazole;
3-(4-chlorobenzo[b]thiophen-7-yl)-2-propyl-5,6-dihydroimidazo[2,1-b]thiazole;
3-(4-chlorobenzo[b]thiophen-7-yl)-2-(1-methylethyl)-5,6-dihydroimidazo[2,1-b]thiazole;
3-(4-chlorobenzo[b]thiophen-7-yl)-2-cyclopropyl-5,6-dihydroimidazo[2,1-b]thiazole;
3-(4-chlorobenzo[b]thiophen-7-yl)-2-vinyl-5,6-dihydroimidazo[2,1-b]thiazole;
3-(4-chlorobenzo[b]thiophen-7-yl)-2-(methylthio)-5,6-dihydroimidazo[2,1-b]thiazole;
[3-(4-chlorobenzo[b]thiophen-7-yl)-5,6-dihydroimidazo[2,1-b]thiazol-2-yl]methanol;
1-[3-(4-chlorobenzo[b]thiophen-7-yl)-5,6-dihydroimidazo[2,1-b]thiazol-2-yl]ethanol;
2-[3-(4-chlorobenzo[b]thiophen-7-yl)-5,6-dihydroimidazo[2,1-b]thiazol-2-yl]ethanol;
3-(5-chlorobenzo[b]thiophen-7-yl)-2-methyl-5,6-dihydroimidazo[2,1-b]thiazole;
3-(5-chlorobenzo[b]thiophen-7-yl)-2-ethyl-5,6-dihydroimidazo[2,1-b]thiazole;
3-(5-chlorobenzo[b]thiophen-7-yl)-2-propyl-5,6-dihydroimidazo[2,1-b]thiazole;
3-(5-chlorobenzo[b]thiophen-7-yl)-2-(1-methylethyl)-5,6-dihydroimidazo[2,1-b]thiazole;
3-(5-chlorobenzo[b]thiophen-7-yl)-2-cyclopropyl-5,6-dihydroimidazo[2,1-b]thiazole;
3-(5-chlorobenzo[b]thiophen-7-yl)-2-vinyl-5,6-dihydroimidazo[2,1-b]thiazole;
3-(5-chlorobenzo[b]thiophen-7-yl)-2-(methylthio)-5,6-dihydroimidazo[2,1-b]thiazole;
[3-(5-chlorobenzo[b]thiophen-7-yl)-5,6-dihydroimidazo[2,1-b]thiazol-2-yl]methanol;
1-[3-(5-chlorobenzo[b]thiophen-7-yl)-5,6-dihydroimidazo[2,1-b]thiazol-2-yl]ethanol;
2-[3-(5-chlorobenzo[b]thiophen-7-yl)-5,6-dihydroimidazo[2,1-b]thiazol-2-yl]ethanol;
3-(4-fluorobenzo[b]thiophen-7-yl)-2-methyl-5,6-dihydroimidazo[2,1-b]thiazole;
3-(4-fluorobenzo[b]thiophen-7-yl)-2-ethyl-5,6-dihydroimidazo[2,1-b]thiazole;
3-(4-fluorobenzo[b]thiophen-7-yl)-2-propyl-5,6-dihydroimidazo[2,1-b]thiazole;
3-(4-fluorobenzo[b]thiophen-7-yl)-2-(1-methylethyl)-5,6-dihydroimidazo[2,1-b]thiazole;

3-(4-fluorobenzo[b]thiophen-7-yl)-2-cyclopropyl-5,6-dihydroimidazo[2,1-b]thiazole;

3-(4-fluorobenzo[b]thiophen-7-yl)-2-vinyl-5,6-dihydroimidazo[2,1-b]thiazole;

3-(4-fluorobenzo[b]thiophen-7-yl)-2-(methylthio)-5,6-dihydroimidazo[2,1-b]thiazole;

[3-(4-fluorobenzo[b]thiophen-7-yl)-5,6-dihydroimidazo[2,1-b]thiazol-2-yl]methanol;

1-[3-(4-fluorobenzo[b]thiophen-7-yl)-5,6-dihydroimidazo[2,1-b]thiazol-2-yl]ethanol;

2-[3-(4-fluorobenzo[b]thiophen-7-yl)-5,6-dihydroimidazo[2,1-b]thiazol-2-yl]ethanol;

3-(5-fluorobenzo[b]thiophen-7-yl)-2-methyl-5,6-dihydroimidazo[2,1-b]thiazole;

3-(5-fluorobenzo[b]thiophen-7-yl)-2-ethyl-5,6-dihydroimidazo[2,1-b]thiazole;

3-(5-fluorobenzo[b]thiophen-7-yl)-2-propyl-5,6-dihydroimidazo[2,1-b]thiazole;

3-(5-fluorobenzo[b]thiophen-7-yl)-2-(1-methylethyl)-5,6-dihydroimidazo[2,1-b]thiazole;

3-(5-fluorobenzo[b]thiophen-7-yl)-2-cyclopropyl-5,6-dihydroimidazo[2,1-b]thiazole;

3-(5-fluorobenzo[b]thiophen-7-yl)-2-vinyl-5,6-dihydroimidazo[2,1-b]thiazole;

3-(5-fluorobenzo[b]thiophen-7-yl)-2-(methylthio)-5,6-dihydroimidazo[2,1-b]thiazole;

[3-(5-fluorobenzo[b]thiophen-7-yl)-5,6-dihydroimidazo[2,1-b]thiazol-2-yl]methanol;

1-[3-(5-fluorobenzo[b]thiophen-7-yl)-5,6-dihydroimidazo[2,1-b]thiazol-2-yl]ethanol;

2-[3-(5-fluorobenzo[b]thiophen-7-yl)-5,6-dihydroimidazo[2,1-b]thiazol-2-yl]ethanol;

3-(5-methoxybenzo[b]thiophen-7-yl)-2-methyl-5,6-dihydroimidazo[2,1-b]thiazole;

2-ethyl-3-(5-methoxybenzo[b]thiophen-7-yl)-5,6-dihydroimidazo[2,1-b]thiazole;

3-(5-methoxybenzo[b]thiophen-7-yl)-2-propyl-5,6-dihydroimidazo[2,1-b]thiazole;

3-(5-methoxybenzo[b]thiophen-7-yl)-2-(1-methylethyl)-5,6-dihydroimidazo[2,1-b]thiazole;

2-cyclopropyl-3-(5-methoxybenzo[b]thiophen-7-yl)-5,6-dihydroimidazo[2,1-b]thiazole;

3-(5-methoxybenzo[b]thiophen-7-yl)-2-vinyl-5,6-dihydroimidazo[2,1-b]thiazole;

3-(5-methoxybenzo[b]thiophen-7-yl)-2-(methylthio)-5,6-dihydroimidazo[2,1-b]thiazole;

[3-(5-methoxybenzo[b]thiophen-7-yl)-5,6-dihydroimidazo[2,1-b]thiazol-2-yl]methanol;

1-[3-(5-methoxybenzo[b]thiophen-7-yl)-5,6-dihydroimidazo[2,1-b]thiazol-2-yl]ethanol;

2-[3-(5-methoxybenzo[b]thiophen-7-yl)-5,6-dihydroimidazo[2,1-b]thiazol-2-yl]ethanol;

2-methyl-3-(2-methylbenzo[b]thiophen-7-yl)-5,6-dihydroimidazo[2,1-b]thiazole;

2-ethyl-3-(2-methylbenzo[b]thiophen-7-yl)-5,6-dihydroimidazo[2,1-b]thiazole;

3-(2-methylbenzo[b]thiophen-7-yl)-2-propyl-5,6-dihydroimidazo[2,1-b]thiazole;

3-(2-methylbenzo[b]thiophen-7-yl)-2-(1-methylethyl)-5,6-dihydroimidazo[2,1-b]thiazole;

2-cyclopropyl-3-(2-methylbenzo[b]thiophen-7-yl)-5,6-dihydroimidazo[2,1-b]thiazole;

3-(2-methylbenzo[b]thiophen-7-yl)-2-vinyl-5,6-dihydroimidazo[2,1-b]thiazole;

3-(2-methylbenzo[b]thiophen-7-yl)-2-(methylthio)-5,6-dihydroimidazo[2,1-b]thiazole;

[3-(2-methylbenzo[b]thiophen-7-yl)-5,6-dihydroimidazo[2,1-b]thiazol-2-yl]methanol;

1-[3-(2-methylbenzo[b]thiophen-7-yl)-5,6-dihydroimidazo[2,1-b]thiazol-2-yl]ethanol;

2-[3-(2-methylbenzo[b]thiophen-7-yl)-5,6-dihydroimidazo[2,1-b]thiazol-2-yl]ethanol;

2-methyl-3-(3-methylbenzo[b]thiophen-7-yl)-5,6-dihydroimidazo[2,1-b]thiazole;

2-ethyl-3-(3-methylbenzo[b]thiophen-7-yl)-5,6-dihydroimidazo[2,1-b]thiazole;

3-(3-methylbenzo[b]thiophen-7-yl)-2-propyl-5,6-dihydroimidazo[2,1-b]thiazole;

3-(3-methylbenzo[b]thiophen-7-yl)-2-(1-methylethyl)-5,6-dihydroimidazo[2,1-b]thiazole;

2-cyclopropyl-3-(3-methylbenzo[b]thiophen-7-yl)-5,6-dihydroimidazo[2,1-b]thiazole;

3-(3-methylbenzo[b]thiophen-7-yl)-2-vinyl-5,6-dihydroimidazo[2,1-b]thiazole;

3-(3-methylbenzo[b]thiophen-7-yl)-2-(methylthio)-5,6-dihydroimidazo[2,1-b]thiazole;

[3-(3-methylbenzo[b]thiophen-7-yl)-5,6-dihydroimidazo[2,1-b]thiazol-2-yl]methanol;

1-[3-(3-methylbenzo[b]thiophen-7-yl)-5,6-dihydroimidazo[2,1-b]thiazol-2-yl]ethanol;

2-[3-(3-methylbenzo[b]thiophen-7-yl)-5,6-dihydroimidazo[2,1-b]thiazol-2-yl]ethanol;

2-methyl-3-(4-methylbenzo[b]thiophen-7-yl)-5,6-dihydroimidazo[2,1-b]thiazole;

2-ethyl-3-(4-methylbenzo[b]thiophen-7-yl)-5,6-dihydroimidazo[2,1-b]thiazole;

3-(4-methylbenzo[b]thiophen-7-yl)-2-propyl-5,6-dihydroimidazo[2,1-b]thiazole;

3-(4-methylbenzo[b]thiophen-7-yl)-2-(1-methylethyl)-5,6-dihydroimidazo[2,1-b]thiazole;

2-cyclopropyl-3-(4-methylbenzo[b]thiophen-7-yl)-5,6-dihydroimidazo[2,1-b]thiazole;

3-(4-methylbenzo[b]thiophen-7-yl)-2-vinyl-5,6-dihydroimidazo[2,1-b]thiazole;

3-(4-methylbenzo[b]thiophen-7-yl)-2-(methylthio)-5,6-dihydroimidazo[2,1-b]thiazole;

[3-(4-methylbenzo[b]thiophen-7-yl)-5,6-dihydroimidazo[2,1-b]thiazol-2-yl]methanol;

1-[3-(4-methylbenzo[b]thiophen-7-yl)-5,6-dihydroimidazo[2,1-b]thiazol-2-yl]ethanol;

[3-(7-fluorobenzo[b]thiophen-2-yl)-5,6-dihydroimidazo[2,1-b]thiazol-2-yl]methanol;

1-[3-(7-fluorobenzo[b]thiophen-2-yl)-5,6-dihydroimidazo[2,1-b]thiazol-2-yl]ethanol;

2-[3-(7-fluorobenzo[b]thiophen-2-yl)-5,6-dihydroimidazo[2,1-b]thiazol-2-yl]ethanol;

3-(4-methoxybenzo[b]thiophen-2-yl)-2-methyl-5,6-dihydroimidazo[2,1-b]thiazole;

2-ethyl-3-(4-methoxybenzo[b]thiophen-2-yl)-5,6-dihydroimidazo[2,1-b]thiazole;

3-(4-methoxybenzo[b]thiophen-2-yl)-2-propyl-5,6-dihydroimidazo[2,1-b]thiazole;

3-(4-methoxybenzo[b]thiophen-2-yl)-2-(1-methylethyl)-5,6-dihydroimidazo[2,1-b]thiazole;

2-cyclopropyl-3-(4-methoxybenzo[b]thiophen-2-yl)-5,6-dihydroimidazo[2,1-b]thiazole;
3-(4-methoxybenzo[b]thiophen-2-yl)-2-vinyl-5,6-dihydroimidazo[2,1-b]thiazole;
3-(4-methoxybenzo[b]thiophen-2-yl)-2-(methylthio)-5,6-dihydroimidazo[2,1-b]thiazole;
[3-(4-methoxybenzo[b]thiophen-2-yl)-5,6-dihydroimidazo[2,1-b]thiazol-2-yl]methanol;
1-[3-(4-methoxybenzo[b]thiophen-2-yl)-5,6-dihydroimidazo[2,1-b]thiazol-2-yl]ethanol;
2-[3-(4-methoxybenzo[b]thiophen-2-yl)-5,6-dihydroimidazo[2,1-b]thiazol-2-yl]ethanol;
3-(5-methoxybenzo[b]thiophen-2-yl)-2-methyl-5,6-dihydroimidazo[2,1-b]thiazole;
2-ethyl-3-(5-methoxybenzo[b]thiophen-2-yl)-5,6-dihydroimidazo[2,1-b]thiazole;
3-(5-methoxybenzo[b]thiophen-2-yl)-2-propyl-5,6-dihydroimidazo[2,1-b]thiazole;
3-(5-methoxybenzo[b]thiophen-2-yl)-2-(1-methylethyl)-5,6-dihydroimidazo[2,1-b]thiazole;
2-cyclopropyl-3-(5-methoxybenzo[b]thiophen-2-yl)-5,6-dihydroimidazo[2,1-b]thiazole;
3-(5-methoxybenzo[b]thiophen-2-yl)-2-vinyl-5,6-dihydroimidazo[2,1-b]thiazole;
3-(5-methoxybenzo[b]thiophen-2-yl)-2-(methylthio)-5,6-dihydroimidazo[2,1-b]thiazole;
[3-(4-methoxybenzo[b]thiophen-2-yl)-5,6-dihydroimidazo[2,1-b]thiazol-2-yl]methanol;
1-[3-(5-methoxybenzo[b]thiophen-2-yl)-5,6-dihydroimidazo[2,1-b]thiazol-2-yl]ethanol;
2-[3-(4-methoxybenzo[b]thiophen-2-yl)-5,6-dihydroimidazo[2,1-b]thiazol-2-yl]ethanol;
3-(6-methoxybenzo[b]thiophen-2-yl)-2-methyl-5,6-dihydroimidazo[2,1-b]thiazole;
2-ethyl-3-(6-methoxybenzo[b]thiophen-2-yl)-5,6-dihydroimidazo[2,1-b]thiazole;
3-[4-(methylthio)benzo[b]thiophen-7-yl]-2-propyl-5,6-dihydroimidazo[2,1-b]thiazole;
2-(1-methylethyl)-3-[4-(methylthio)benzo[b]thiophen-7-yl]-5,6-dihydroimidazo[2,1-b]thiazole;
2-cyclopropyl-3-[4-(methylthio)benzo[b]thiophen-7-yl]-5,6-dihydroimidazo[2,1-b]thiazole;
3-[4-(methylthio)benzo[b]thiophen-7-yl]-2-vinyl-5,6-dihydroimidazo[2,1-b]thiazole;
2-(methylthio)-3-[4-(methylthio)benzo[b]thiophen-7-yl]-5,6-dihydroimidazo[2,1-b]thiazole;
[3-[4-(methylthio)benzo[b]thiophen-7-yl]-5,6-dihydroimidazo[2,1-b]thiazol-2-yl]methanol;
1-[3-[4-(methylthio)benzo[b]thiophen-7-yl]-5,6-dihydroimidazo[2,1-b]thiazol-2-yl]ethanol;
2-[3-[4-(methylthio)benzo[b]thiophen-7-yl]-5,6-dihydroimidazo[2,1-b]thiazol-2-yl]ethanol;
2-methyl-3-[5-(methylthio)benzo[b]thiophen-7-yl]-5,6-dihydroimidazo[2,1-b]thiazole;
2-ethyl-3-[5-(methylthio)benzo[b]thiophen-7-yl]-5,6-dihydroimidazo[2,1-b]thiazole;
3-[5-(methylthio)benzo[b]thiophen-7-yl]-2-propyl-5,6-dihydroimidazo[2,1-b]thiazole;
2-(1-methylethyl)-3-[5-(methylthio)benzo[b]thiophen-7-yl]-5,6-dihydroimidazo[2,1-b]thiazole;
2-cyclopropyl-3-[5-(methylthio)benzo[b]thiophen-7-yl]-5,6-dihydroimidazo[2,1-b]thiazole;
3-[5-(methylthio)benzo[b]thiophen-7-yl]-2-vinyl-5,6-dihydroimidazo[2,1-b]thiazole;
2-(methylthio)-3-[5-(methylthio)benzo[b]thiophen-7-yl]-5,6-dihydroimidazo[2,1-b]thiazole;
[3-[5-(methylthio)benzo[b]thiophen-7-yl]-5,6-dihydroimidazo[2,1-b]thiazol-2-yl]methanol;
1-[3-[5-(methylthio)benzo[b]thiophen-7-yl]-5,6-dihydroimidazo[2,1-b]thiazol-2-yl]ethanol; and
2-[3-[5-(methylthio)benzo[b]thiophen-7-yl]-5,6-dihydroimidazo[2,1-b]thiazol-2-yl]ethanol.

18. A compound according to claim 5 in which g is 0, 1 or 2;
   $R_1$ is halo, an alkyl group containing 1 to 3 carbon atoms, an alkoxy group containing 1 to 3 carbon atoms or hydroxy; and
   $R_2$ represents H, an alkyl group containing 1 to 3 carbon atoms, a hydroxyalkyl group containing 1 to 6 carbon atoms, a $C_{1-3}$alkylthio group, a cycloalkyl group containing 3 to 6 carbon atoms, or an alkenyl group containing 2 to 8 carbon atoms.

19. A compound according to claim 6 in which g is 0, 1 or 2;
   $R_1$ is halo, an alkyl group containing 1 to 3 carbon atoms, an alkoxy group containing 1 to 3 carbon atoms or hydroxy; and
   $R_2$ represents H, an alkyl group containing 1 to 3 carbon atoms, a hydroxyalkyl group containing 1 to 6 carbon atoms, a $C_{1-3}$alkylthio group, a cycloalkyl group containing 3 to 6 carbon atoms, or an alkenyl group containing 2 to 8 carbon atoms.

20. A compound according to claim 7 in which g is 0, 1 or 2;
   $R_1$ is halo, an alkyl group containing 1 to 3 carbon atoms, an alkoxy group containing 1 to 3 carbon atoms or hydroxy; and
   $R_2$ represents H, an alkyl group containing 1 to 3 carbon atoms, a hydroxyalkyl group containing 1 to 6 carbon atoms, a $C_{1-3}$alkylthio group, a cycloalkyl group containing 3 to 6 carbon atoms, or an alkenyl group containing 2 to 8 carbon atoms.

21. A compound according to claim 8 in which g is 0, 1 or 2;
   $R_1$ is halo, an alkyl group containing 1 to 3 carbon atoms, an alkoxy group containing 1 to 3 carbon atoms or hydroxy; and
   $R_2$ represents H, an alkyl group containing 1 to 3 carbon atoms, a hydroxyalkyl group containing 1 to 6 carbon atoms, a $C_{1-3}$alkylthio group, a cycloalkyl group containing 3 to 6 carbon atoms, or an alkenyl group containing 2 to 8 carbon atoms.

22. A pharmaceutical composition comprising a therapeutically effective amount of a compound of Formula I, as claimed in claim 1, together with a pharmaceutically acceptable diluent or carrier.

23. A process for preparing a pharmaceutical composition for oral administration comprising a compound of Formula I, as claimed in claim 1, the process comprising:
   mixing from about 1 mg to about 1000 mg of a compound of claim 1 with an inert diluent in the presence of any excipients, disintegrating agents, lubricating agents, aqueous suspension agents, oil suspension agents, binders, colouring agents, sweetening agents, flavouring agents, preservatives, effervescent couples or any other ingredient suitable for oral formulation; and
   formulating the composition as a tablet, gelatin capsule, enteric-coated capsule, aqueous suspension, oil suspension, or any other formulation for oral administration; and optionally formulating the composition as a sustained release formulation.

24. A method of treating depression, anxiety, psychoses, schizophrenia, cognitive disorders, obsessive-compulsive behaviour, panic attacks, social phobias, eating disorders, bulimia, anorexia, snacking and binge eating, stress, and/or aiding cessation of smoking, comprising administering a therapeutically effective amount of a compound of Formula I, as claimed in claim 1, to a patient in need thereof.

25. A method of reducing a craving to smoke in human beings which comprises the administration of a therapeutically effective amount of a compound of Formula I, as chimed in claim 1, to a patient in need thereof.

26. A method of treating depression, anxiety, psychoses, schizophrenia, cognitive disorders, obsessive-compulsive behaviour, panic attacks, and social phobias according to claim 24, comprising administering a therapeutically effective amount of a compound of Formula I, as claimed in claim 1, to a patient in need thereof.

27. A method of treating eating disorders, bulimia, anorexia, snacking and binge eating according to claim 24, comprising administering a therapeutically effective amount of a compound of Formula I, as claimed in claim 1, to a patient in need thereof.

28. A method of treating depression according to claim 24, comprising administering a therapeutically effective amount of a compound of Formula I, as claimed in claim 1, to a patient in need thereof.

29. A method of aiding cessation of smoking according to claim 24, comprising administering a therapeutically effective amount of a compound of Formula I, as claimed in claim 1, to a patient in need thereof.

* * * * *